(12) United States Patent
Johnson et al.

(10) Patent No.: US 6,667,161 B1
(45) Date of Patent: Dec. 23, 2003

(54) CHROMOGENIC SUBSTRATES OF SIALIDASE OF BACTERIAL, VIRAL, PROTOZOA, AND VERTEBRATE ORIGIN AND METHODS OF MAKING AND USING THE SAME

(75) Inventors: Stephen C. Johnson, Birmingham, AL (US); Ming Lou, Birmingham, AL (US); Shijia Yan, Birmingham, AL (US)

(73) Assignees: Ibbex, Inc., Birmingham, AL (US); UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/412,896

(22) Filed: Oct. 5, 1999

Related U.S. Application Data

(63) Continuation-in-part of application No. 08/958,356, filed on Oct. 27, 1997, now abandoned.

(51) Int. Cl.[7] ................................................. C12Q 1/34
(52) U.S. Cl. ......................................... 435/18; 536/4.1
(58) Field of Search ........................ 435/18, 5; 536/4.1

(56) References Cited

U.S. PATENT DOCUMENTS

| | | | |
|---|---|---|---|
| 4,351,823 A | | 9/1982 | Rubin |
| 5,663,055 A | | 9/1997 | Turner et al. |
| 5,714,509 A | * | 2/1998 | Luo et al. ............ 514/415 |
| 5,719,020 A | * | 2/1998 | Liav et al. |

FOREIGN PATENT DOCUMENTS

| | | |
|---|---|---|
| EP | 0413561 | 2/1991 |
| GB | 2008103 | 5/1979 |
| WO | 8902473 | 3/1989 |
| WO | 9109975 | 12/1990 |
| WO | 9212256 | 7/1992 |
| WO | 0024753 | 5/2000 |

OTHER PUBLICATIONS

WO 9109975. Turner et al (Jul. 1991) Chromogenic 7- or 8-position modified N-acetylneuraminic acid substrates and methods for diagnosing human influenza therewith.*
WO 9109972. Turner et al (Jul. 1991) Methods for diagnosing human influenza and 4-position modified chromogenic N-acetylneuraminic acid substrates and use therein.*
WO 9110744. Turner et al (Jul. 1991) Chromogenic 9-position modified N-acetylneuraminic acid substrates and methods for diagnosing human influenza therewith.*
Hirst, G.K. (1941) "The Agglutination of Red Blood Cells by Allontoic Fluid of Chick Embryos Infected with Influenza Virus" Science 94(2427):22–23.

Gornati, Rosalba, Subhash Basu, Giovanni Bernardini, Angela M. Rizzo, Federica Rossi, Bruno Berra (1997) "Activities of flycolipid glycosyltransferases and sialidases during the early development of *Xenopus laevis*" 166:117–124.
Cacalano, Grace, Maureen Kays, Lisa Salman, Alice Prince (1992) "Production of the *Pseudomonas aeruginosa* Neuraminidase Is Increased under Hyperosmolar Conditions and Is Regulated by Genes Involved in Alginate Expression" J. Clin. Invest. 891866–1874.
Bratosin et al. (1995) "Flow cytofluorimetric analysis of young and senescent human erythrocytes probed with lectins, Evidence that sialic acid control their life span" Glycoconjugate Journal 12:258–267.
Liu, Chongguang, Maryna C. Eichelberger, Richard W. Compans, Gillian M. Air (1995) "Influenza Type A Virus Neuraminidase Does Not Play A Role In Viral Entry, Replication, Assembly, or Budding" Journal of Virology 69(2):1099–1106.
Liljemark, William F., Cynthia G. Bloomquist, Laurie J. Fenner, Patrick J. Antonelli, M. Cecilia Coulter (1989) "Effect of Neuraminidase on the Adherence to Salivary Pellicle of *Streptococcus sanguis* and *Streptococcus mitis*" Caries Res. 23:141–145.
Briselden, Ann Marie, Bernard J. Moncla, Claire E. Stevens, Sharon L. Hillier (1992) "Sialidases (Neuraminidases) in Bacterial Vaginosis and Bacterial Vaginosis–Associated Microflora" J. Clinical Microbiology 30(3):663–666.
Bonten, Erik, Aarnoud van der Spoel, Maarten Fornerod, Gerard Grosveld, Alessandra d'Azzo (1996) "Characterization of human lysosomal neuraminidase defines the molecular basis of the metabolic storage disorder sialidosis" Genes & Development 10:3156–3169.
Cross, George A.M., Garry B. Takle (1993) "The Surface Trans–sialidase Family of *Trypanosoma Cruzi*" Ann. Rev. Microbiology 47:385–411.
Crennell, Susan, Elspeth Garman, Graeme Laver, Eric Vimr, Garry Taylor (1994) "Crystal structure of *Vibrio cholerae* neuraminidase reveals dual lectin–like domains in addition to the catalytic domain" Structure 2(6):535–44.
Crennell, Susan J., Elspeth F. Garman, W. Graeme Laver, Eric R. Vimr, Garry L. Taylor (1993) "Crystal structure of a bacterial sialidase (from *Salmonella typhimurium* LT2) shows the same fold as an influenza virus neuraminidase" Proc. Natl. Acad. Sci. USA 90:9852–9856.

(List continued on next page.)

Primary Examiner—Ralph Gitomer
(74) Attorney, Agent, or Firm—Saliwanchik, Lloyd & Saliwanchik

(57) ABSTRACT

The current invention relates to the design, synthesis, and biochemical evaluation of chromogenic substrate compounds for sialidases of bacterial, viral, protozoa, and vertebrate (including human) origin. In particular, this invention provides a novel class of effective compounds as chromogenic substrates of these sialidases which yield chromogenic products after reactions catalyzed by sialidase take place. Also provided are methods of making these substrate compounds, methods of diagnosis and prognosis of sialidase related diseases using these substrate compounds.

8 Claims, 16 Drawing Sheets

OTHER PUBLICATIONS

Lentz, Michael R., Robert G. Webster, Gillian M. Air (1987) "Site–Directed Mutation of the Active Site of Influenza Neuraminidase and Implications for the Catalytic Mechanism" Biochemistry 26:(17):5351–5358.

Aamlid, Kai H., Grantham Lee, Brian V. Smith, Anthony C. Richardson, Robert G. Price (1990) "New colorimetric substrates for the assay of glycosidases" Carbohydrate Research 205:c5–c9.

Baggett, Neil and Brian J. Marsden (1982) "Reinvestigation Of The Synthesis Of 4–Methylcoumarin–7–YL 5–Acetamido–3, 5–Dideoxy–α–D–glycero–D–galacto–2–Nonulopyranosi–donic Acid, A Fluorogenic Substrate For Neuraminidase" Carbohydrate Research 110:11–18.

Eschenfelder, Volker and Reinhard Brossmer (1987) "Synthesis of p–nitrophenyl 5–acetamido–3, 5–dideoxy–α–D–Glycero–D–galacto–2–nonulopyranosidonic acid, a chromogenic substrate for sialidases" Carbohydr. Res. 162: 294–297.

Eschenfelder, Volker and Reinhard Brossmir (1987) "5–Bromo–indol–3–yl 5–Acetamido–3, 5–dideoxy–α–D–glycero–D–galactononulopyranosidonic Acid, a Novel Chromogenic Substrate for the Staining of Sialidase Activity" Glycoconjugate J. 4:171–178.

Freudenberg, K., H. Resnik, H. Boesenberg, D. Rasenack (1952) "Das an der Verholzung Beteiligte Fermentsystem" Chem. Ber. 85:641–647.

Holmquist, L., R. Brossmer (1972) "Specificity of neuraminidase, synthesis and properties of the 2–aminoethyl α– and the 2–pyridyl α– and β–glycosides of N–acetyl–D–neuraminic acid" Hoppe–Seyler's Z. Physiol. Chem. 353:1346–1350.

Horwitz, J.P., J. Chua, R.J. Curby, A.J. Tomson, M.A. Darooge, B.E. Fisher, J. Mauricio, I. Klundt (1964) "Substrates for Cytochemical Demonstration of Enzyme Activity. I. Some Substituted 3–Indolyl–β–D–glycopyranosides" J. Med. Chem. 7:574–575.

de Kiewiet, T.E., H. Stephen (1931) "2–Hydroxy– 4–methoxy– and 4–Hydroxy–2–methoxybenzaldehydes" J. Chem. Soc. 133:84–85.

Kuhn, Richard, Peter Lutz and Donald L. MacDonald (1966) "Syntheses anomerer Sialinsäure–methylketoside" Chem. Ber. 99:611–617.

Ley, Arthur Newton, Raymond John Bowers, Saul Wolfe (1988) "Indoxyl–β–D–glucuronide, a novel chromogenic reagent for the specific detection and enumeration of *Escherichia coli* in environmental samples" Can. J. Microbiol. 34:690–693.

Myers, R. W., R. T. Lee, Y. C. Lee, G. H. Thomas, L.. W. Reynolds, Y. Uchida (1980) "The Synthesis of 4–Methylumbelliferyl α–Ketoside of N–Acetylneuraminic Acid and its Use in a Fluorometric Assay for Neuraminidase" Anal. Biochem. 101:166–174.

Ogura, Haruo and Kimio Furuhata (1986) "Syntheses Of 2–O–Glycosyl Derivatives of N–Acetyl–D–Neuraminic Acid" Carbohydrate Research 158:37–51.

Okamoto, Kaoru, and Toshio Goto (1990) "Glycosidation Of Sialic Acid" Tetrahedron 46(7):5835–5857.

Patel, Atula and Anthony C. Richardson (1986) "3–Methoxy–4–(2–Nitrovinyl)Phenyl Glycosides As Potential Chromogenic Substrates For The Assay Of Glycosidases" Carbohydrate Research 146:241–249.

Paulsen, Hans and Peter Matschulat (1991) "Synthese von C–Glycosiden der N–Acetylneuraminsäure und weiteren Derivaten" Liebigs Ann. Chem. 487–495.

Robertson, Alexander (1927) "Syntheses of Glucosides. Part I. The Synthesis of Indican" J. Chem. Soc. 1937–1943.

Tiemann, F., P. Koppe (1881) "Ueber die Darstellung von Protocatechualdehyd aus Brenzcatechin, sowie einige Derivate des Guajacols und Kreosols" Chem Ber. 14:2015–2028.

Warner, Thomas G. and John S. O'Brien (1979) "Synthesis of 2'–(4–Methylumbelliferyl)–α–D–N–acetylneuraminic Acid and Detection of Skin Fibroblast Neuraminidase in Normal Humans and in Sialidosis" Biochemistry 18(13):2783–2787.

Anderson, F.B. and D.H. Leaback (1961) "Substrates For The Histochemical Localization Of Some Glycosidases" Tetrahedron 12:236–239.

Palese, P., D. Bucher, E.D. Kilbourne (1973) "Applications of a Synthetic Neuraminidase Substrate" *Applied Microbiology* 25(2):195–201.

Derwent Abstract, AN 90–143137 PN JP 2088594 (Mar. 28, 1990).

Ashwell et al. (1992) "Pathways for the hydrolysis of glycosides of N–acetylneuraminic acid" *J. Am. Chem. Soc.* 114:10158–10166.

Cabezas et al. (1980) "Nueraminidase from influenza virus A (H3N2)" *Biochim. Et Biophys. Acta* 616:228–238.

Sinnott et al. (1993) "Leech Sialidase L cleaves the glycon–aglycon bond with the substrate in a normally disfavored conformation" *J. Am. Chem. Soc.* 115:3334–3335.

Lehninger, Biotechmistry $2^{nd}$ Edition, p. 594, Worth Publishers, Inc., New York (1975).

Baumberger, Franz and Andrea Vasella (1986) "4–Methylumbelliferyl 5–Acetamido–3,4,5–trideoxy–α–D–manno–2–nonulopyranosidionic Acid: Synthesis and Resistance to Bacterial Sialidases" Helvetica Chimica Acta 69: 1927–1935.

Zbiral, Erich, Erwin Schreimer, Mamikrao M. Salunkhe, Gerhard Schulz, Reinhard G. Kleineidam, Roland Schauer (1989) "Synthesis of the 4–Methylumbelliferyl 2α–Glycosides of 7–Epi–, 8–Epi–, and 7,8–Bis(epi)–N–acetylneuraminic Acids, as well as of 7–Deoxy–, 8–Deoxy–, 9–Deoxy–, and 4,7–Dideoxy–N–acetylneuraminic Acids and Their Behaviour Towards Sialidase from *Vibrio cholerae*" Liebigs Ann. Chem. pp. 519–526.

* cited by examiner

CHROMOGENIC SUBSTRATES OF SIALIDASE OF BACTERIAL, VIRAL, PROTOZOA, AND VERTEBRATE ORIGIN AND METHODS OF MAKING AND USING THE SAME

CROSS-REFERENCE TO A RELATED APPLICATION

This application is a continuation-in-part of U.S. patent application Ser. No. 08/958,356, filed on Oct. 27, 1997 now abandoned.

The subject invention was made with government support under a research project contract from the University of Alabama at Birmingham as a grant from the US Defense Advanced Research Projects Agency, grant number MDA 972-97-K-0002, and a Small Business Innovative Research (SBIR) Grant from the National Institutes of Health, grant number 1 R43 HD36964-01. The government has certain rights in this invention.

FIELD OF THE INVENTION

The current invention relates to the design, synthesis, and biochemical evaluation of chromogenic substrate compounds for sialidases of bacterial, viral, protozoa, and vertebrate (including human) origin. In particular, this invention provides a novel class of effective compounds as chromogenic substrates of these sialidases which yield chromogenic products after reactions catalyzed by sialidase take place. Also provided are methods of making these substrate compounds, methods of diagnosis and prognosis of sialidase related diseases using these substrate compounds.

BACKGROUND OF THE INVENTION

Sialidase (EC 3.2.1.18, also known as neuraminidase, acylneuraminyl hydrolase) is a protein enzyme produced by many organisms such as bacteria, viruses, protozoa, and vertebrates including humans (Hirst, 1941). This class of enzymes catalyzes the hydrolysis of a terminal sialic acids which are α-ketosidically linked to glycoproteins, glycolipids, and polysaccharides through an O-glycosidic bond (Drzeniek, 1972).

There are a large number of biological functions ascribed to sialidase enzyme, including cell-cell recognition phenomena and the pathogenicity of some infections by sialidase-bearing microorganisms (Schauer, 1985). In bacteria, sialidase helps bacterial adhesion to tissues, and provides additional nutritional sources (Crennell, et al., 1994). In the case of the influenza virus, sialidase is one of two surface glycoproteins and is considered to be important for both transporting the virus through mucin (Kienk and Rott, 1988) and for the elution of virus progeny from infected cells (Palese, et al., 1974). In a parasite, *Trypanosoma cruzi*, a sialidase (also known as trans-sialidase) removes sialic acids from infected cells and decorates its own surface with these sialic acids. In humans, silaidases are involved in protein digestion, immune responses, and cell proliferation. Abnormal production of sialidases may lead to serious human diseases such as sialidosis or increased *Pseudomonas aeruginosa* infection in cystic fibrosis patients.

Since sialidases are associated with many diseases, a color-producing substrate of sialidase would be an excellent diagnostic or prognostic reagent for sialidase-related diseases. For instance, sialidase level is elevated in bacterial vaginosis (Briselden, et al., 1992). Measurement of sialidase level in the vaginal samples could be used to diagnose bacterial vaginosis. In periodontal disease caused by bacterial infection, it has been shown that the presence of sialidase increases the colonization of harmful bacteria (Liljemark, et al., 1989). In influenza virus, viral sialidases are elevated in the mouth of patients. Measurement of sialidase level in the throat swab samples could be used to diagnose influenza virus. The cell invasion form of *T. cruzi*, Trypomastigote, expresses high levels of trans-sialidase activity; therefore, measurement of trans-sialidase level could be used for diagnosis of *T. cruzi* infection and for monitoring disease progress (Cross and Tackle, 1993). In cystic fibrosis patients, *Pseudomonas aeruginosa* infection is one of the leading causes of death. Sialidase was shown to be involved in the disease progress (Cacalano, et al., 1992). Sialidase is also related to the regulation of cell proliferation (Bratosin, et al., 1995), the clearance of plasma proteins (Bonten, et al., 1996), and the catabolism of gangliosides and glycoproteins (Gornati, et al., 1997).

The structure of sialidase has been extensively studied using numerous antigenic variants from several crystallographic studies (Colman, 1989, Varghese, et al., 1983; Colman, et al., 1983; Varghese, et al. 1992; Taylor and Itzstein, 1994). A key feature arising from these studies has been the fact that despite up to 50% variation in the primary sequence of the enzyme, the active site residues are highly conserved in both influenza A and B virus strains.

N-Acetylneuraminic acid, the product resulting from sialidase-mediated hydrolysis of polysaccharides, glycoproteins, and glycolipids, is shown below with the numbering system used to denote the carbon atoms:

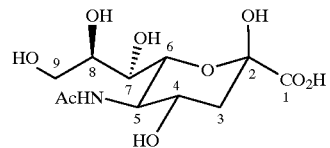

4-position modified N-acetylneuraminic acid analogs (Neu5Ac) have previously been described (Turner, et al., 1997):

2-O-(4-methylumbelliferyl)-4-deoxy-N-acetylneuraminic acid-alpha-ketoside,

2-O-(3-cyanoumbelliferyl)-4-deoxy-N-acetylneuraminic acid-alpha-ketoside,

2-O-(2-nitrophenyl)-4-deoxy-N-acetylneuraminic acid-alpha-ketoside,

2-O-(4-nitrophenyl)-4-deoxy-N-acetylneuraminic acid-alpha-ketoside,

2-O-(3-resorufin)-4-deoxy-N-acetylneuraminic acid-alpha-ketoside,

2-O-(5-bromo-4-chloro-3-indolyl)-4-deoxy-N-acetylneuraminic acid-alpha-ketoside, 2-O-(5-bromo-3-indolyl)-4-deoxy-N-acetylneuraminic acid-alpha-ketoside, 2-O-(3-indolyl)-4-deoxy-N-acetylneuraminic acid-alpha-ketoside, 2-O-[4-(4nitrophenylazo)phenyl]-4-deoxy-N-acetylneuraminic acid-alpha-ketoside, 2-O-([4-(4-nitrophenylazo)resocinyl]-4-deoxy-N-acetylneuraminic acid-alpha-ketoside, 2-O-(3-methoxyphenyl)-4-deoxy-N-acetylneuraminic acid-alpha-ketoside, 2-O-(3-dimethylaminophenyl)-4-deoxy-N-acetylneuraminic acid-alpha-ketoside, 2-O-(4-chloro-1-naphthyl)-4-deoxy-N-acetylneuraminic acid-alpha-ketoside,
2-O-(6-bromo-2-naphthyl)-4-deoxy-N-acetylneuraminic acid-alpha-ketoside,
2-O-(4-methylumbelliferyl)-4-methoxy-N-acetylneuraminic acid-alpha-ketoside,
2-O-(2-nitrophenyl)-4-methoxy-N-acetylneuraminic acid-alpha-ketoside,
2-O-(4-nitrophenyl)-4-methoxy-N-acetylneuraminic acid-alpha-ketoside,
2-O-(3-cyanoumbelliferyl)-4-methoxy-N-acetylneuraminic acid-alpha-ketoside,
2-O-(3-resorufin)-4-methoxy-N-acetylneuraminic acid-alpha-ketoside,
2-O-(5-bromo-4-chloro-3-indolyl)-4-methoxy-N-acetylneuraminic acid-alpha-ketoside,
2-O-(5-bromo-3-indolyl)-4-methoxy-N-acetylneuraminic acid-alpha-ketoside,
2-O-(3-indolyl)-4-methoxy-N-acetylneuraminic acid-alpha-ketoside,
2-O-[4-(4nitrophenylazo)phenyl]-4-methoxy-N-acetylneuraminic acid-alpha-ketoside,
2-O-[4-(4-nitrophenylazo)resocinyl]-4-methoxy-N-acetylneuraminic acid-alpha-ketoside,
2-O-(3-methoxyphenyl)-4-methoxy-N-acetylneuraminic acid-alpha-ketoside,
2-O-(3-dimethylaminophenyl)-4-methoxy-N-acetylneuraminic acid-alpha-ketoside,
2-O-(6-bromo-2-naphthyl)-4-methoxy-N-acetylneuraminic acid-alpha-ketoside,
2-O-(4-chloro-1-naphthyl)-4-deoxy-N-acetylneuraminic acid-alpha-ketoside,
2-O-(4-methylumbelliferyl)-4-methoxy-N-acetylneuraminic acid-alpha-ketoside,
2-O-(2-nitrophenyl)-4-methoxy-N-acetylneuraminic acid-alpha-ketoside,
2-O-(4-methylumbelliferyl)-4-ethoxy-N-acetylneuraminic acid-alpha-ketoside,
2-O-(2-nitrophenyl)-4-ethoxy-N-acetylneuraminic acid-alpha-ketoside,
2-O-(4-nitrophenyl)-4-ethoxy-N-acetylneuraminic acid-alpha-ketoside,
2-O-(3-cyanoumbelliferyl)-4-ethoxy-N-acetylneuraminic acid-alpha-ketoside,
2-O-(3-resorufin)-4-ethoxy-N-acetylneuraminic acid-alpha-ketoside,
2-O-(5-bromo-4-chloro-3-indolyl)-4-ethoxy-N-acetylneuraminic acid-alpha-ketoside,
2-O-(5-bromo-3-indolyl)-4-ethoxy-N-acetylneuraminic acid-alpha-ketoside,
2-O-(3-indolyl)-4-ethoxy-N-acetylneuraminic acid-alpha-ketoside,
2-O-[4-(4-nitrophenylazo)phenyl]-4-ethoxy-N-acetylneuraminic acid-alpha-ketoside,
2-O-[4-(4-nitropheynazo)resorcinyl]-4-ethoxy-N-acetylneuraminic acid-alpha-ketoside,
2-O-(3-methoxyphenyl)-4-ethoxy-N-acetylneuraminic acid-alpha-ketoside,
2-O-(3-dimethylaminophenyl)-4-ethoxy-N-acetylneuraminic acid-alpha-ketoside,
2-O-(4-chloro-1-naphthyl)-4-ethoxy-N-acetylneuraminic acid-alpha-ketoside,
2-O-(4-methylumbelliferyl)-4-fluoro-N-acetylneuraminic acid-alpha-ketoside,
2-O-(2-nitrophenyl)-4-fluoro-N-acetylneuraminic acid-alpha-ketoside,
2-O-(4-nitrophenyl)-4-fluoro-N-acetylneuraminic acid-alpha-ketoside,
2-O-(3-cyanoumbelliferyl)-4-fluoro-N-acetylneuraminic acid-alpha-ketoside,
2-O-(3-resorufin)-4-methoxy-N-acetylneuraminic acid-alpha-ketoside,
2-O-(5-bromo-4-chloro-3 indolyl)-4-fluoro-N-acetylneuraminic acid-alpha-ketoside,
2-O-(5-bromo-3-indolyl)-4-fluoro-N-acetylneuraminic acid-alpha-ketoside,
2-O-[4-(4-nitrophenylazo)phenyl]-4-fluoro-N-acetylneuraminic acid-alpha-ketoside,
2-O-[4-(4-nitropheynazo)resorcinyl]4-fluoro-N-acetylneuraminic acid-alpha-ketoside,
2-O-(3-methoxyphenyl)-4-fluoro-N-acetylneuraminic acid acid-alpha-ketoside,
2-O-[3-(dimethylamino)phenyl]-4-fluoro-N-acetylneuraminic acid acid-alpha-ketoside,
2-O-(4-chloro-1-naphthyl)-4-fluoro-N-acetylneuraminic acid acid-alpha-ketoside, and
2-O-(6-bromo-2-naphthyl)-4-fluoro-N-acetylneuraminic acid acid-alpha-ketoside.

Also, 4,7-alkoxy modified N-acetylneuraminic acid (Neu5Ac) analogs with viral sialidase have been reported (Liav, et al., 1998):

2-O-(4-methylumbelliferyl)-4,7-dimethoxy-N-acetylneuraminic acid-alpha-ketoside,
2-O-(2-nitrophenyl)-4,7-dimethoxy-N-acetylneuraminic acid-alpha-ketoside,
2-O-(4-nitrophenyl)-4,7-methoxy-N-acetylneuraminic acid-alpha-ketoside,
2-O-(3-cyanoumbelliferyl)-4,7-dimethoxy-N-acetylneuraminic acid-alpha-ketoside,
2-O-(3-resorufin)-4,7-dimethoxy-N-acetylneuraminic acid-alpha-ketoside,
2-O-(5-bromo-4-chloro-3-indolyl)-4,7-dimethoxy-N-acetylneuraminic acid-alpha-ketoside, 2-O-(5-bromo-3-indolyl)-4,7-dimethoxy-N-acetylneuraminic acid-alpha-ketoside, 2-O-(3-indolyl)-4,7-dimethoxy-N-acetylneuraminic acid-alpha-ketoside, 2-O-[4-(4-nitrophenylazo)phenyl]-4,7-dimethoxy-N-acetylneuraminic acid-alpha-ketoside,
2-O-[4-(4-nitrophenylazo)resorcinyl]-4,7-dimethoxy-N-acetylneuraminic acid-alpha-ketoside, 2-O-(3-methoxyphenyl)-4,7-dimethoxy-N-acetylneuraminic acid-alpha-ketoside, 2-O-(3-dimethylaminophenyl)-4,7-dimethoxy-N-acetylneuraminic acid-alpha-ketoside, 2-O-(6-bromo-2-naphthyl)-4,7-dimethoxy-N-acetylneuraminic acid-alpha-ketoside, 2-O-(4-chloro-1-naphthyl)-4,7-dimethoxy-N-acetylneuraminic acid-alpha-ketoside, as well as the corresponding 4,7-diethoxy, 4,7-dipropyl, and 4,7-dibutyl derivatives.

The applicant is unaware of any prior reports on the reactivity of 7-, 8-, 9-, 4,8-, 4,9-, 4,7,8,9-, 4,7,9-, 4,8,9-, 7,8-, 7,9-, 7,8,9-, or 8,9-position modified Neu5Ac analogues with viral sialidase.

The applicant is unaware of any prior reports on the reactivity of modified Neu5Ac analogs analogous to those presented herein with bacterial, vertebrate, or protozoal sialidase.

The substrate compounds of the current invention produce a visible color change upon hydrolysis, which is highly advantageous in medical diagnostic applications.

BRIEF SUMMARY OF THE INVENTION

In one embodiment, the current invention relates to the design and synthesis of novel chromogenic substrate compounds for sialidases. In another embodiment, the subject invention pertains to the use of the novel chromogenic substrates in assays for the detection of sialidases. The sialidases which are detected using the procedures and compounds of the subject invention are of bacterial, viral, protozoa, and vertebrate (including human) origin. In a specific embodiment, the subject invention provides a novel class of compounds which are useful as chromogenic substrates of sialidases.

In one embodiment, the present invention provides chromogenic sialidase substrate compounds, analogues, pharmaceutically acceptable salts, derivatives, and mixtures thereof having the following formula:

General Structure I

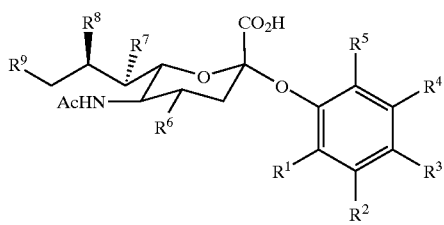

wherein, $R^1$, $R^2$, $R^4$, and $R^5$ can each, independently, be selected from the group consisting of H, $R^{11}$, $OC(O)R^{11}$, $NO_2$, $NHC(O)R^{11}$, Cl, Br, I, F, CHO, $C(O)R^{11}$, $C(N-OH)NH_2$, $OPO_3R^{10}$, $OPO_2(CH_2)_jCH_3$, $CH_2PO_3R^{10}$, $OSO_3R^{10}$, $OSO_2(CH_2)_jCH_3$, $CH_2SO_3R^{10}$, and CN, where j is an integer from 0 to 3; wherein $R^3=NO_2$, CHO, $(CR^{12}=CR^{12})_kCN$ or $(CR^{12}=CR^{12})_kNO_2$, where k is an integer from 1 to 3, or

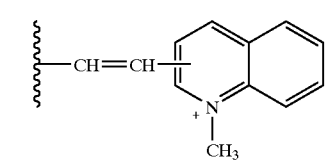

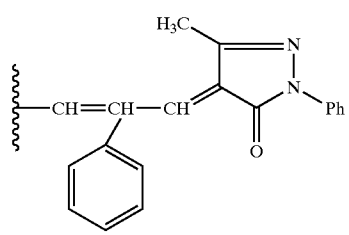

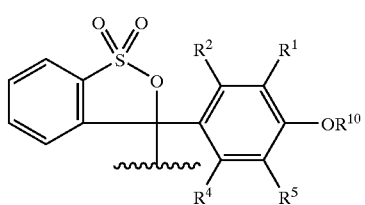

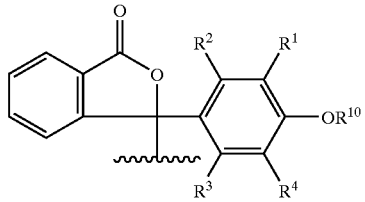

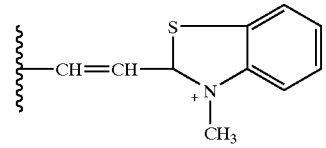

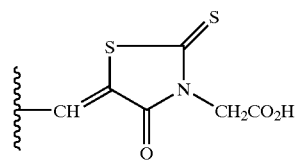

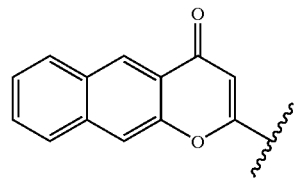

wherein, $R^6$, $R^7$, $R^8$, and $R^9$ can each, independently, be selected from the group consisting of H, $N_3$, $R^{11}$, $NO_2$, $NHC(=NH)N(R^{10})_2$, $NHC(O)R^{11}$, $C(O)R^{11}$, Cl, Br, I, F, $SR^{10}$, and $(CH_2)_xC(=NH)N(R^{10})_2$ where x is an integer from 0 to 3; wherein $R^{10}$=H, $C(CH_3)_3$, $CH(CH_3)_2$, $CH_2CH(CH_3)_2$, $CH(CH_3)(CH_2)_mCH_3$, or $(CH_2)_mCH_3$, where m is an integer from 0 to 3; wherein $R^{11}=R^{10}$, $OR^{10}$, or $N(R^{10})_2$; wherein, $R^{12}$=H or $(CH_2)_n$; where n is an integer from 0 to 3.

Also provided are chromogenic sialidase substrate compounds, analogues, pharmaceutically acceptable salts, derivatives, and mixtures thereof having the formula of General Structure I, wherein, $R^1$, $R^3$, and $R^5$ can each, independently, be selected from the group consisting of H, $R^{11}$, $OC(O)R^{11}$, $NO_2$, $NHC(O)R^{11}$, Cl, Br, I, F, CHO, $C(O)R^{11}$, $C(N-OH)NH_2$, $OPO_3R^{10}$, $OPO_2(CH_2)_jCH_3$, $CH_2PO_3R^{10}$, $OSO_3R^{10}$, $OSO(CH_2)_jCH_3$, $CH_2SO_3R^{10}$, or CN, where j is an integer from 0 to 3; wherein $R^2$ or $R^4$=H, $R^{11}$, $OC(O)R^{11}$, $NO_2$, $NHC(O)R^{11}$, Cl, Br, I, F, CHO, $C(O)R^{11}$, $C(N-OH)NH_2$, $OPO_3R^{10}$, $OPO_2(CH_2)_jCH_3$, $CH_2PO_3R^{10}$, $OSO_3R^{10}$, $OSO_2(CH_2)_jCH_3$, $CH_2SO_3R^{10}$, CN, $(CR^{12}=CR^{12})_kCN$, and $(CR^{12}=CR^{12})_kNO_2$, where j is an integer from 0 to 3, and where k is an integer from 1 to 3, or

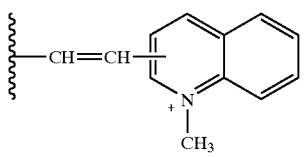

-continued

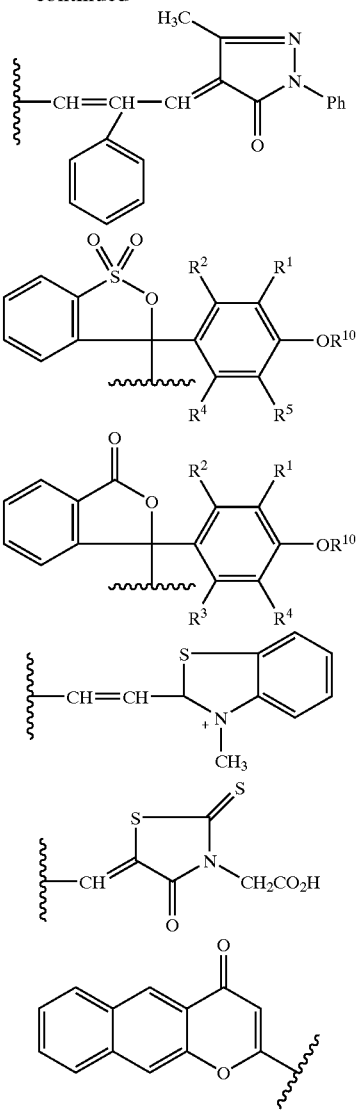

wherein, $R^6$, $R^7$, $R^8$, and $R^9$ can each, independently, be selected from the group consisting of H, $N_3$, $R^{11}$, $NO_2$, NHC(=NH)N($R^{10}$)$_2$, NHC(O)$R^{11}$, C(O)$R^{11}$, Cl, Br, I, F, $SR^{10}$, and $(CH_2)_xC(=NH)N(R^{10})_2$ where x is an integer from 0 to 3; wherein $R^{10}$=H, C($CH_3$)$_3$, CH($CH_3$)$_2$, $CH_2$CH($CH_3$)$_2$, CH($CH_3$)($CH_2$)$_m$$CH_3$, or $(CH_2)_m$$CH_3$, where m is an integer from 0 to 3; wherein $R^{11}$=$R^{10}$, $OR^{10}$, or N($R^{10}$)$_2$; wherein, $R^{12}$=H or $(CH_2)_n$; where n is an integer from 0 to 3.

Also provided are chromogenic sialidase substrate compounds, analogues, pharmaceutically acceptable salts, derivatives, and mixtures thereof having the formula of General Structure I, wherein, $R^1$ and $R^5$ are each, independently, selected from the group consisting of H, $R^{11}$, OC(O)$R^{11}$, $NO_2$, NHC(O)$R^{11}$, Cl, Br, I, F, CHO, C(O)$R^{11}$, C(N—OH)NH$_2$, $OPO_3R^{10}$, $OPO_2(CH_2)_jCH_3$, $CH_2PO_3R^{10}$, $OSO_3R^{10}$, $OSO_2(CH_2)_jCH_3$, $CH_2SO_3R^{10}$, CN, where j is an integer from 0 to 3, $(CR^{12}=CR^{12})_kCN$ and $(CR^{12}=CR^{12})_kNO_2$, where k is an integer from 1 to 3; wherein, $R^2$, $R^3$, and $R^4$ can each, independently, be selected from the group consisting of H, $R^{11}$, OC(O)$R^{11}$, $NO_2$, NHC(O)$R^{11}$, Cl, Br, I, F, CHO, C(O)$R^{11}$, C(N—OH)NH$_2$, $OPO_3R^{10}$, $OPO_2(CH_2)_jCH_3$, $CH_2PO_3R^{10}$, $OSO_3R^{10}$, $OSO_2(CH_2)_jCH_3$, $CH_2SO_3R^{10}$, and CN, where j is an integer from 0 to 3; wherein, $R^6$, $R^7$, $R^8$, and $R^9$ are each, independently, selected from the group consisting of H, $N_3$, $R^{11}$, $NO_2$, NHC(=NH)N($R^{10}$)$_2$, NHC(O)$R^{11}$, C(O)$R^{11}$, Cl, Br, I, F, $SR^{10}$, $(CH_2)_xC(=NH)N(R^{10})_2$, where x is an integer from 0 to 3; wherein $R^{10}$=H, C($CH_3$)$_3$, CH($CH_3$)$_2$, $CH_2$CH($CH_3$)$_2$, CH($CH_3$)($CH_2$)$_m$$CH_3$, or $(CH_2)_m$$CH_3$, where m is an integer from 0 to 3; wherein $R^{11}$=$R^{10}$, $OR^{10}$, or N($R^{10}$)$_2$; wherein $R^{12}$=H or $(CH_2)_n$; where n is an integer from 0 to 3.

Also provided are chromogenic sialidase substrate compounds, analogues, pharmaceutically acceptable salts, derivatives, and mixtures thereof having the following formula:

General Structure II

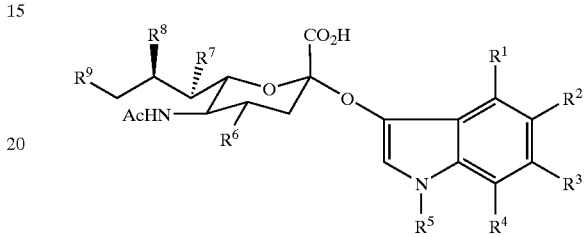

wherein, $R^1$, $R^2$, $R^3$, and $R^4$ are each, independently, selected from the group consisting of H, $R^{11}$, OC(O)$R^{11}$, $NO_2$, Cl, Br, I, F, CHO, C(O)$R^{11}$, C(N—OH)NH$_2$, $OPO_3R^{10}$, $OPO_2(CH_2)_jCH_3$, $CH_2PO_3R^{10}$, $OSO_3R^{10}$, $OSO_2(CH_2)_jCH_3$, $CH_2SO_3R^{10}$, and CN, where j is an integer from 0 to 3; wherein, $R^5$=H or $(CH_2)_kCH_3$, where k is an integer from 0 to 4; wherein, $R^6$, $R^7$, $R^8$, and $R^9$ are each, independently, selected from the group consisting of H, $N_3$, $R^{11}$, $NO_2$, NHC(=NH)N($R^{10}$)$_2$, NHC(O)$R^{11}$, C(O)$R^{11}$, Cl, Br, I, F, $SR^{10}$, and $(CH_2)_xC(=NH)N(R^{10})_2$, where x is an integer from 0 to 3; wherein, $R^{10}$=H, C($CH_3$)$_3$, CH($CH_3$)$_2$, $CH_2$CH($CH_3$)$_2$, CH($CH_3$)($CH_2$)$_m$$CH_3$, or $(CH_2)_m$$CH_3$, where m is an integer from 0 to 3; wherein, $R^{11}$=$R^{10}$, $OR^{10}$, or N($R^{10}$)$_2$.

Also provided are chromogenic sialidase substrate compounds, analogues, pharmaceutically acceptable salts, derivatives, and mixtures thereof having the following formula:

General Structure IIIa

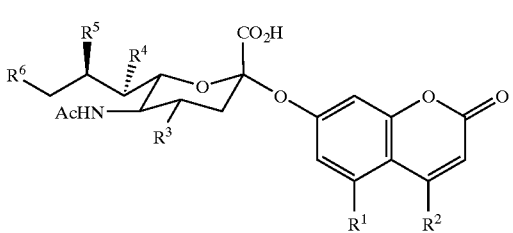

wherein, $R^1$=H, $R^8$, OC(O)$R^8$, $NO_2$, NHC(O)$R^8$, Cl, Br, I, F, CHO, C(O)$R^8$, C(N—OH)NH$_2$, $OPO_3R^7$, $OPO_2(CH_2)_jCH_3$, $CH_2PO_3R^7$, $OSO_3R^7$, $OSO_2SO_3R^7$, or CN, where j is an integer from 0 to 3; wherein, $R^2$=H, C($CH_3$)$_3$, CH($CH_3$)$_2$, $CH_2$CH($CH_3$)$_2$, CH($CH_3$)($CH_2$)$_m$$CH_3$, or $(CH_2)_m$$CH_3$, where m is an integer from 0 to 3; wherein $R^3$, $R^4$, $R^5$, and $R^6$ are each, independently, selected from the group consisting of H, $N_3$, $R^8$, $NO_2$, NHC(=NH)N($R^7$)$_2$, NHC(O)$R^8$, C(O)$R^8$, Cl, Br, I, F, $SR^7$, and $(CH_2)_xC(=NH)N(R^7)_2$, where x is an integer from 0 to 3; wherein $R^7$=H, C($CH_3$)$_3$, CH($CH_3$)$_2$, $CH_2$CH($CH_3$)$_2$, CH($CH_3$)($CH_2$)$_m$$CH_3$, or $(CH_2)_m$$CH_3$, where m is an in from 0 to 3; wherein, $R^8$=$R^7$, $OR^7$, or N($R^7$)$_2$.

Also provided are chromogenic sialidase substrate compounds, analogues, pharmaceutically acceptable salts, derivatives, and mixtures thereof having the following formula:

General Structure IIIb

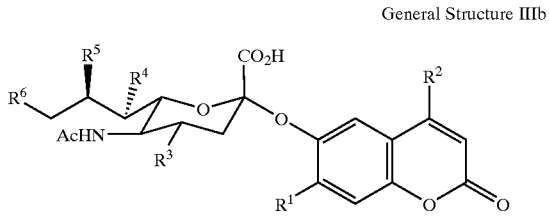

wherein, $R^1$=H, $R^8$, OC(O)$R^8$, $NO_2$, Cl, Br, I, F, CHO, C(O)$R^8$, C(N—OH)$NH_2$, $OPO_3R^7$, $OPO_2(CH_2)_jCH_3$, $CH_2PO_3R^7$, $OSO_3R^7$, $OSO_2(CH_2)_jCH_3$, $CH_2SO_3R^7$, or CN, where j is an integer from 0 to 3; wherein, $R^2$=H, $C(CH_3)_3$, $CH(CH_3)_2$, $CH_2CH(CH_3)_2$, $CH(CH_3)(CH_2)_mCH_3$, or $(CH_2)_mCH_3$, where m is an integer from 0 to 3; wherein, $R^3$, $R^4$, $R^5$, and $R^6$ are each, independently, selected from the group consisting of H, $N_3$, $R^8$, $NO_2$, NHC(=NH)N($R^7$)$_2$, NHC(O)$R^8$, C(O)$R^8$, Cl, Br, I, F, $SR^7$, and $(CH_2)_xC(=NH)N(R^7)_2$, where x is an integer from 0 to 3; wherein $R^7$=H, $C(CH_3)_3$, $CH(CH_3)_2$, $CH_2CH(CH_3)_2$, $CH(CH_3)(CH_2)_mCH_3$, or $(CH_2)_mCH_3$, where m is an integer from 0 to 3; wherein, $R^8$=$R^7$, $OR^7$, or N($R^7$)$_2$.

Also provided are chromogenic sialidase substrate compounds, analogues, pharmaceutically acceptable salts, derivatives, and mixtures thereof having the following formula:

General Structure IVa

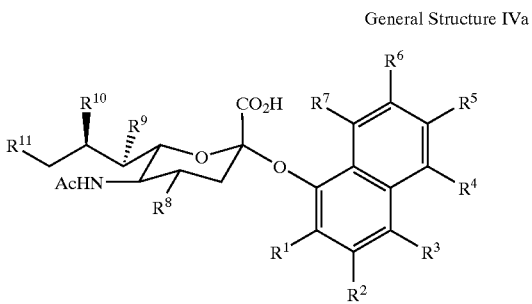

wherein, $R^1$, $R^2$, $R^3$, $R^4$, $R^5$, $R^6$, and $R^7$ are each, independently, selected from the group consisting of H, $R^{13}$, OC(O)$R^{13}$, $NO_2$, Cl, Br, I, F, CHO, C(O)$R^{13}$, C(N—OH)$NH_2$, $OPO_3R^{12}$, $OPO_2(CH_2)_jCH_3$, $CH_2PO_3R^{12}$, $OSO_3R^{12}$, $OSO_2(CH_2)_jCH_3$, $CH_2SO_3R^{12}$, and where j is an integer from 0 to 3; wherein, $R^8$, $R^9$, $R^{10}$, $R^{11}$ are each, independently, selected from the group consisting of H, $N_3$, $R^{13}$, $NO_2$, NHC(=NH)N($R^{12}$)$_2$, NHC(O)$R^{13}$, C(O)$R^{13}$, Cl, Br, I, F, $SR^{12}$, and $(CH_2)_xC(=NH)N(R^{12})_2$, where x is an integer from 0 to 3; wherein, $R^2$=H, $C(CH_3)_3$, $CH(CH_3)_2$, $CH_2CH(CH_3)_2$, $CH(CH_3)(CH_2)_mCH_3$, or $(CH_2)_mCH_3$, where m is an integer form 0 to 3; wherein, $R^{13}$=$R^{12}$, $OR^{12}$, or N($R^{12}$)$_2$.

Also provided are chromogenic sialidase substrate compounds, analogues, pharmaceutically acceptable salts, derivatives, and mixtures thereof having the following formula:

General Structure IVb

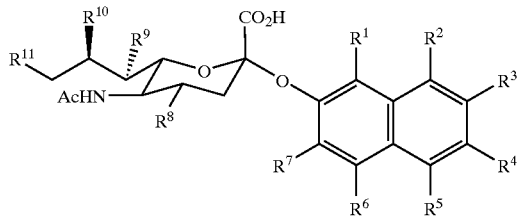

wherein, $R^1$, $R^2$, $R^3$, $R^4$, $R^5$, $R^6$, and $R^7$ are each, independently, selected from the group consisting of H, R$^3$, OC(O)$R^{13}$, $NO_2$, Cl, Br, I, F, CHO, C(O)$R^{13}$, C(N—OH)$NH_2$, $OPO_3R^{12}$, $OPO_2(CH_2)_jCH_3$, $CH_2PO_3R^{12}$, $OSO_3R^{12}$, $OSO_2(CH_2)_jCH_3$, $CH_2SO_3R^{12}$, and CN, where j is an integer from 0 to 3; wherein, $R^8$, $R^9$, $R^{10}$, and $R^{11}$ are each, independently, selected from the group consisting of H, $N_3$, $R^{13}$, $NO_2$, NHC(=NH)N($R^{12}$)$_2$, NHC(O)$R^{13}$, C(O)$R^{13}$, Cl, Br, I, F, $SR^{12}$, and $(CH_2)_xC(=NH)N(R^{12})_2$, where x is an integer from 0 to 3; wherein, $R^{12}$=H, $C(CH_3)_3$, $CH(CH_3)_2$, $CH_2CH(CH_3)_2$, $CH(CH_3)(CH_2)_mCH_3$, or $(CH_2)_mCH_3$, where m is an integer form 0 to 3; wherein, $R^{13}$=$R^{12}$, $OR^{12}$, or N($R^{12}$)$_2$.

The subject invention further pertains to analogues, salts, derivatives, and mixtures of the exemplified compounds.

DETAILED DESCRIPTION OF THE INVENTION

Figure 1:
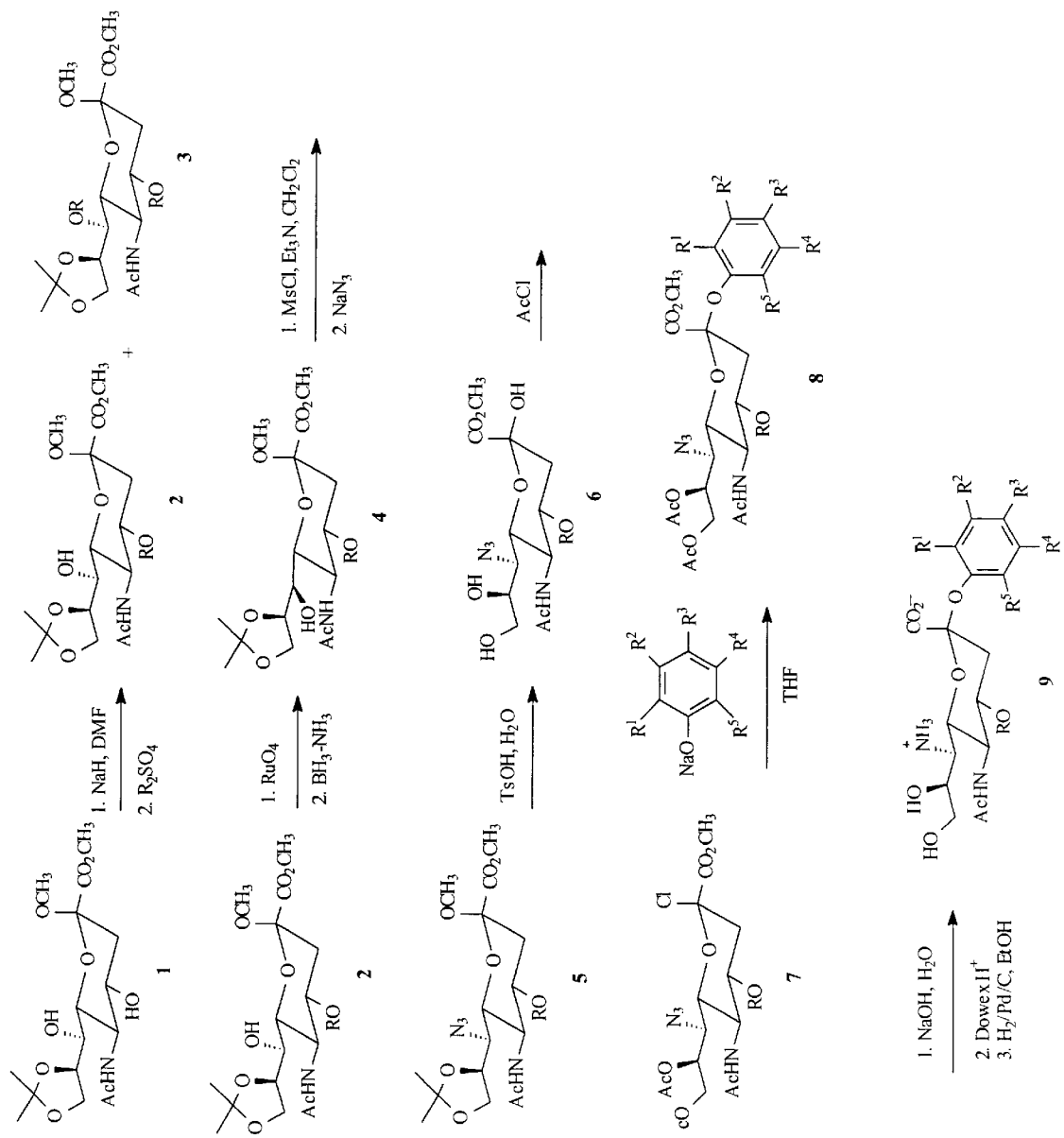
FIG. 1—synthetic approaches for selected 4-O-alkyl 7-substituted examples from General Structure I are summarized in this reaction scheme.

The subject invention pertains to materials and methods useful for detecting sialidase. Sialidase is an enzyme known to be associated with a variety of pathological conditions. Sialidases are produced by bacteria, viruses, and protozoa; therefore, detecting the presence of sialidase in a biological sample is indicative of the presence of these microbes. In specific embodiments, the detection of sialidases can be performed according to the subject invention in order to identify vaginal and periodontal infections, influenza virus, and to detect *Pseudomonas aeruginosa* in cystic fibrosis patients.

The presence of sialidase is detected according to the subject invention through the use of novel chromogenic substrate compounds. These compounds advantageously provide a visible color change when acted upon by sialidase. Thus, these substrates, when utilized according to the teachings of the subject invention, can be used to easily and accurately detect the presence of sialidase in a sample. In a preferred embodiment, the sample which is tested is a biological sample such as blood, mucous, saliva, and the like.

The subject invention provides compounds having structures as shown in General Structures I, II, IIIa, IIIb, IVa, and IVb. The invention further includes derivatives, analogues, and salts of the exemplified compounds. These derivatives, analogues, and salts, which can be readily prepared by one skilled in the art and having benefit of the instant disclosure, fall within the scope of the present invention so long as such compounds have the characteristic of producing a color, either directly or when treated with an additional chemical reagent, when acted upon by a sialidase enzyme.

The compounds of the subject invention can be employed in a wide variety of assay formats. Typically, the assay will involve contacting a sample to be tested for the presence of sialidase with a chromogenic enzyme substrate of the subject invention. A color change occurring after the sample is contacted with the substrate, either directly or when treated with an additional chemical reagent, is indicative of the presence of sialidase. The assay may optimally utilize positive and/or negative controls to aid in the interpretation and verification of the results. The results may also be quantitated using standard optical measuring instrumentation.

Materials and Methods

Biochemical evaluation for the chromogenic product of viral sialidase substrate compounds. Sialidase can be obtained from, for example, purified recombinant bacterial sialidase from Salmonella T., whole influenza virus, or culture medium containing secreted human sialidase from the 2CFSME cell line. The sialidase preparation is added to a buffer of sodium acetate (0.05 to 0.5 M; pH 5.0–6.0), and the substrate compound is provided at about 0.2–1.0 mM concentration. It should be noted that numerous other examples of buffer solution may be used, including organic acids such as citrate buffers, for example, as well as inorganic buffers, including potassium, sodium, calcium, and other such salts thereof. The reaction mixture is incubated at ambient temperature to physiological temperature (i.e., about 18–40° C.) for a period of time, generally 5–30 minutes in a total volume of approximately 100–500 μL. At the end of the reaction, and in the presence of sialidase activity, the reaction mixture exhibits a color change either directly or after the addition of another reagent, generally a buffer solution of pH between 7.5 and 14. The color change is readily visible. The color change can be quantitated spectrophotometrically by measuring the light absorption of the reaction mixture. It should be noted that, if necessary, numerous solutions could be used as the added reagent to exhibit a color change. These include sodium hydroxide, and numerous other inorganic acid salts, as well as nitroblue tetrazolium, diazonium salts, or metal cations including Mg++, among others.

General methodologies. The following general methods are applicable to the synthesis of compounds of the invention. Modifications or verifications of these methods can readily be utilized by those skilled in the art having the benefit of the instant disclosure.

Esterification and O-glycosylation. Treatment of the appropriate compound with an alcohol, generally methanol, at temperatures ranging from 0° C. to 45° C., for a period of time, generally 4 hours to 3 days, provides the crude esterified and/or O-glycosylated product.

Those skilled in the art would recognize that other standard procedures are available for esterification of the same material, including a two-step procedure which involves the use of a cation exchange resin, e.g., Amberlyst 15 or Dowex 50W-X8, among others, in the presence of an alcohol to provide esterification, followed by O-glycosylation of the resulting intermediate via various means.

Guanylation of amines with subsequent deprotection. Treatment of the appropriate compound containing a free amino group with N,N'-bis-(tert-benzyloxycarbonyl)-2-methyl-2-thiopseudourea in an organic solvent, usually dichloromethane, in the presence of an organic base, usually triethylamine, at temperatures ranging from 0° C. to 35° C. for a period of time, generally 1 hour to 4 days, provides the crude guanidino product (Tian, et al., 1992). Concentration of the crude material, followed by chromatography provides the purified bis-tert-benzyloxycarbonyl guanidino product. Treatment of the bis-tert-benzyloxycarbonyl protected guanidino intermediate with palladium-on-carbon catalyst in the presence of hydrogen readily provides the desired guanidino compound (Tian, et al., 1992).

Those skilled in the art would recognize that other standard methods are available for the guanylation of amines, including methods that employ the use of N,N'-bis-(tert-benzyloxycarbonyl)-N-trifluoromethansulfonylguaidine (Feichtinger, et al., 1998) or N,N'-bis-tert-benzyloxycarbonylthiourea (Iwanowicz, et al., 1993), among others.

O-silylation. Treatment of the appropriate compound containing a free hydroxyl group with tert-butyldimethylsilyl chloride in an organic solvent, generally N,N-dimethylformamide, in the presence of an organic base, generally imidazole, for a period of time, generally 4–48 hours, at room temperature provides the respective O-silylated product. Concentration of the reaction mixture, treatment of the residue with an organic solvent, generally ethyl acetate or diethylether, and water, followed by separation, drying, and concentration of the organic phase provides a crude product sufficient for purification on chromatography.

Those skilled in the art would recognize that numerous other silylating agents could be used for O-silylation of a free hydroxyl, including tert-butyldiphenylsilyl chloride (Hanessian and Lavallee, 1975), triphenylsilyl chloride (Barker, et al., 1963), among others. Additionally, those skilled in the art would recognize that other methods of hydroxyl group protection are available, including ethers and esters, among others.

De-silylation. Treatment of the appropriate compound containing a silyl ether with a solution of tetrabutylammonium fluoride in tetrahydrofuran (Corey and Snider, 1972) at room temperature for a period of time, generally, 1–12 hours, provides the de-silylation product. Concentration of the reaction mixture, treatment of the residue with an organic solvent, generally ethyl acetate, and water, followed by separation, drying, and concentration of the organic phase provides a crude product sufficient for purification on chromatography.

Those skilled in the art would recognize numerous other methods of de-silylating the same material, including the use of potassium fluoride with a crown ether (Stork and Hudrlik, 1968) or triethylamine-buffered hydrofluoric acid (Nystrom, et al., 1985), among others.

Hydolysis of O-glycosides and/or acetal protecting groups. Treatment of the appropriate product with an aqueous solution of p-toluenesulfonic acid (TsOH) at room temperature, for a period of time, generally 30 minutes to 24 hours, followed by neutralization of the reaction medium provides the crude product. Lyophilization of the crude product gives the purified hydroxylated compound.

Those skilled in the art would recognize numerous other methods of hydrolysis of similar compounds, including the use of numerous other organic or inorganic acids, as well as the use of ion exchange resins, particularly Dowex, Amberlyst, or Amberlyte resins, among others.

O-alkylation. Treatment of the appropriate hydroxylated product with a suspension of sodium hydride in anhydrous tetrahydrofuran with stirring at temperatures ranging from 0° C. to about 30° C. for a period of time, generally 10 minutes to about 48 hours, followed by the addition of an alkylating agent, generally 1.0 to 1.5 molar equivalents, provides the O-alkylation product. This procedure has been reported (Liav, et al., 1998) for the preparation of numerous 4-O-alkyl products of Neu5Ac. In this procedure, the use of dialkyl sulfate compounds as the alkylating agent provides an effective means to providing the O-alkylation products. Traditionally, dimethyl sulfate, diethyl sulfate, dipropyl sulfate, and dibutyl sulfate serve as alkylating agents; however, other dialkyl sulfates may be employed. The more sterically hindered hydroxyls (i.e., C-7 hydroxyl relative to C-4 hydroxyl in the case presented herein) can be alkylated using these conditions when 1.5 equivalents of alkylating agent are used at temperatures of 22–30° C., as has been reported (Liav, et al., 1998).

Those skilled in the art would recognize numerous other methods of O-alkylation analogous to those presented herein. These include the use of sodium hydride, or an alternate salt thereof, followed by the addition of methyl iodide (Lodge and Heathcock, 1987), or an alternate alkyl salt, among others.

Oxidation of hydroxyls to ketones. Treatment of the appropriate hydroxylated product with a preparation of ruthenium tetroxide will readily provide the appropriate ketone intermediate. This method has been employed in the selective oxidation of the 4-hydoxyl group in methyl 8,9-di-O-isopropylidine-2-O-methyl-Neu5Ac (compound 1, FIG. 1), a procedure reported herein (Zbiral, et al., 1989), and in the oxidation of the 7-hydroxyl group in a compound analogous to one that is reported herein (Salunkhe, et al., 1988).

The ruthenium tetroxide preparation is generated according to known procedures (Johnson, 1993), and involves the use of commercially available ruthenium dioxide in an aqueous solution of sodium periodate to which potassium carbonate is added at room temperature. When the resulting mixture generates a yellow color that is consistent and does not fade with stirring, the ruthenium tetroxide preparation is generated. At that time, a solution of the appropriate alcohol in dichloromethane is added dropwise with stirring over a period of time, generally 10 minutes to 4 hours. The resulting two-phase suspension is stirred at room temperature for a period of time, generally 12 to 36 hours, during which time, the pH of the suspension is maintained at ca. 9 by the periodic addition of aqueous potassium carbonate. After completion, the reaction is quenched by the addition of 2-propanol, and the product is isolated by extraction, followed by concentration under reduced pressure.

Those skilled in the art would recognize that other standard procedures are available for the oxidation of appropriate hydroxyls to ketones, including pyridinium chlorochromate (Kang and Hong, 1987), pyridinium dichromate (Czernecki, et al., 1985),and manganese dioxide (Barakat, et al., 1956), among others.

Diastereoselective reduction of ketones to provide hydroxyls. The appropriate ketone analogue is treated with dry methanol and the resulting solution is cooled to 0° C. Borane-ammonia complex is then added, and the stirring is continued for a period of time, generally 30 minutes to 4 hours. The solvent is removed under reduced pressure, and the crude material is purified via chromatography over silica gel. This method has been employed in the diastereoselective reduction of the 4-keto function of an analogue derived from the regioselective oxidation of the 4-hydroxyl group in methyl 8,9-di-O-isopropylidine-2-O-methyl-Neu5Ac (compound 1, FIG. 1), to provide the 4-epi sialic acid analogue, compound 24 (FIG. 4) (Zbiral, et al., 1989). Additionally, this method has been employed in the diastereoselective reduction of the 7-keto function of a compound analogous to one reported herein (Salunkhe, et al., 1988).

Those skilled in the art would recognize other methods of effecting the diastereoselective reduction of the appropriate ketone (Brown, et al. 1987), including those methods employing diisopinocamphenylchloroborane or B-isopinocamphenyl-9-borabicyclo[3.3.1]nonane, among others.

O-acetylation and glycosyl chloride preparation. Treatment of the appropriate esterified NeuSAc modified product with acetyl chloride with stirring at room temperature under anhydrous conditions for a period of time, generally 20–24 hours, results in formation of the per-O-acetylated glycosyl chloride. Note that in some instances the bubbling of dry hydrogen chloride (gas) into the reaction vessel is necessary to effect glycosyl chloride formation. Concentration of the reaction mixture with the water bath temperature not exceeding 35° C., and drying the residue in vacuo provides the product as a foam sufficiently pure for subsequent reactions.

Those skilled in the art would recognize that other standard procedures are available for O-acetylation and glycosyl chloride preparation of the same materials, including a previously reported two-step procedure on an analogous compound (Kuhn, et, al., 1966) which involves per-O-acetylation with acetic anhydride in perchloric acid, followed by formation of the glycosyl chloride by treatment with acetyl chloride.

O-glycosylation. Treatment of the appropriate hydroxy aromatic derivative with sodium hydride in anhydrous tetrahydrofuran with stirring at room temperature for a period of time, generally 1 to 3 hours, results in formation of the sodium salt. Subsequent treatment of the sodium salt with the glycosyl chloride (compound 7, for example) with stirring, for a period of time, generally 12–60 hours, at room temperature results in O-glycosylation. Concentration of the reaction mixture, treatment of the residue with an organic solvent, generally ethyl acetate, and water, followed by separation, drying, and concentration of the organic phase provides a crude product sufficient for purification on chromatography.

Those skilled in the art would recognize that other standard procedures are available for O-glycosylation of the same materials, such as traditional Lewis Acid-mediated O-glycosylation methodologies (Okamoto and Goto, 1990), as well as the use of alternate salts of the substituted aromatic hydroxyl derivative, including tetrabutylammonium (Baggett and Marsden, 1982) or silver (Holmquist and Brossmer, 1972) salts, among others.

Hydrogenation of azides to amines. Treatment of the appropriate azido compound with palladium-on-carbon catalyst (generally 5–20 mol %) in an organic solvent, generally ethyl acetate or ethanol, at room temperature followed by exposure to hydrogen gas under a pressure ranging from atmospheric to ca. 55 psi for a period of time, generally 2 to 36 hours, readily provides the appropriate amino compound. The reaction mixture is filtered through celite to remove all catalyst, and the filtrate is concentrated under reduced pressure to provide the crude amino compound. Subsequent purification by chromatography provides the purified amino compound.

Those skilled in the art would recognize that there are numerous other methods of reducing an azido group to an amino group, including the use of other catalysts such as Raney nickel, among others.

Activation of free hydroxyl for displacement and displacement of activated hydroxyl with appropriate nucleophiles. Treatment of the appropriate compound with a free hydroxyl group with methanesulfonyl chloride and triethylamine in an organic solvent, generally dichloromethane, at temperatures ranging from −10° C. to 25° C., for a period of time, generally 1–24 hours, provides the activated hydroxyl intermediate. Subsequent treatment of the activated hydroxyl intermediate with an appropriate nucleophile (lithium azide, for example) in an anhydrous organic solvent, generally dimethylformamide or acetonitrile, for a period of time, generally 1–48 hours, provides the crude substituted product. Concentration of the reaction mixture, treatment of the residue with an organic solvent, generally ethyl acetate, and water, followed by separation, drying, and concentration of the organic phase provides a crude product sufficient for purification on chromatography. This method of activation followed by displacement has been applied to the synthesis of numerous carbohydrate analogues.

Those skilled in the art would recognize that other standard procedures are available for the activation of a free hydroxyl for displacement, including procedures employing trifluoromethanesulfonic anhydride in pyridine and dichloromethane (Ambrose, et al, 1983; Johnson, et al., 1993), 1,1-thiocarbonyldiimidazole in dimethylformamide (Johnson, et al., 1993), p-toluenesulfonyl chloride in pyridine (Johnson, et al., 1993), or Mitsunobu methodologies (Mitsunobu et al., 1972) employing triphenylphosphine and diethylazodicarboxylate, among others.

Those skilled in the art would also recognize that other standard reagents (nucleophiles) are available for the displacement of activated hydroxyls, such as thioacetate (Hojo, et al., 1977), phthalimide (Mitsunobu, et al., 1972), lithium chloride (Clarke and Owen, 1949), as well as the use of other salts of the nucleophiles, including lithium or sodium salts, among others. The use of these alternate nucleophiles, among others, would provide access to numerous analogues of the General Structures.

De-O-acetylation and de-esterification. The O-acetylated O-glycoside ester is taken up in aqueous sodium hydroxide and stirred at room temperature for a period of time, generally 1–4 hours. The mixture is then adjusted to pH 3–5 with Dowex 50W-X4 (H+) resin. Filtration, followed by lyophilization of the filtrate affords the desired de-O-acetylated and de-esterified material. The material is usually sufficiently pure for subsequent synthetic procedures; however, it may be purified by chromatography.

Those skilled in the art would recognize that other standard procedures are available for the complete de-O-acetylation and de-esterification of the same material, including a two-step procedure which involves complete de-O-acetylation of the same material with sodium methoxide in methanol or with an appropriate ion exchange resin, e.g., Amberlite IRA-400 (OH—), followed by de-esterification using conditions of acid hydrolysis or base hydrolysis.

Synthesis of Chromogenic Substrates of Sialidases

A. Compounds with General Structure I and their salts and derivatives, may be prepared using any of several methods known in the art for the synthesis of substituted sialic acid analogues containing analogous structures.

To illustrate, synthetic approaches for selected examples of 4-, 4,7-, and 4,7,9-position modified analogues of General Structure I are summarized in FIGS. 1–4. These synthetic approaches are representative of the types of procedures that can be employed. Table 1 lists specific compounds that are prepared using the synthetic approaches presented herein.

TABLE 1

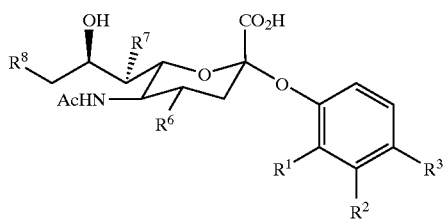

| Cpd. | R₁ | R₂ | R₃ | R₆ | R₇ | R₈ |
|---|---|---|---|---|---|---|
| 9a | H | H | CHO | OCH₃ | NH₂ | OH |
| 9b | H | H | CH=CHNO₂ | OCH₃ | NH₂ | OH |
| 15a | —H | —OCH₃ | —CHO | —OCH₃ | NH₂ | —NH₂ |
| 15b | —H | —OCH₃ | —CH=CHNO₂ | —OCH₃ | NH₂ | —NH₂ |
| 21a | —OCH₃ | —H | —CHO | —OCH₃ | OCH₃ | —NH₂ |
| 21b | —OCH₃ | —H | —CH=CHNO₂ | —OCH₃ | OCH₃ | —NH₂ |
| 22a | —H | —OCH₃ | —CHO | —OCH₃ | —OCH₃ | NHC(=NH)NH₂ |
| 22b | —H | —OCH₃ | —CH=CHNO₂ | —OCH₃ | OCH₃ | —NHC(=NH)NH₂ |
| 29a | —H | —OCH₃ | —CHO | —NHC(=NH)NH₂ | —OH | —OH |
| 29b | —H | —OCH₃ | —CH=CHNO₂ | —NHC(=NH)NH₂ | —OH | —OH |

In another specific embodiment, the subject invention includes compounds having the following structures:

TABLE 2

| Cpd. | R₆ | R₇ | R₈ | R⁹ |
|---|---|---|---|---|
| 9c | OCH₃ | NH₂ | OH | H |
| 15c | OCH₃ | NH₂ | NH₂ | H |
| 21c | OCH₃ | OCH₃ | NH₂ | H |
| 22c | OCH₃ | OCH₃ | NHC(=NH)NH₂ | H |
| 29c | NHC(=NH)NH₂ | OH | OH | H |

Advantageously, these compounds presented in Table 2 produce a blue color change when acted upon by viral sialidase.

It should be noted that the present invention relates to chromogenic substrate compounds that are useful in the detection of sialidase. As such, the present invention relates to chromogenic substrate compounds in addition to those presented in Tables 1 and 2. Likewise, numerous other analogues with varying $R^1$, $R^2$, $R^3$, $R^6$, $R^7$, and/or $R^8$, as defined in the Summary of the Invention, can be prepared using analogous or altogether different methods.

4-O-Alkyl 7-Substituted Analogues From General Structure I

FIG. 1 illustrates constructing a basic skeleton of General Structure I via O-alkylation of methyl 8,9-O-isopropylidene-2-O-methyl-Neu5Ac (1) using conditions previously reported (Liav, 1998) for the same compound. Compound 1 is generally prepared according to known procedures (Kim, 1988; Liav, 1996; Hartman and Zbiral, 1989). O-Alkylation of 1 using any of a series of dialkyl sulfate analogues including dimethyl sulfate, diethyl sulfate, diisopropyl sulfate, among others, provides the 4-O-alkyl compound 2 and the 4,7-di-O-alkyl compound 3 as a separable mixture on chromatography. Treatment of compound 2 with ruthenium tetroxide provides the intermediate 7-keto analogue, followed by subsequent diastereoselective reduction with borane-ammonia gives the 7-epi-sialic acid analogue 4. Compound 4, with a free 7-hydroxyl group, is then activated for displacement via the methanesulfonate intermediate by reaction of 4 with methanesulfonyl chloride (MsCl) in the presence of organic base. Nucleophilic displacement of the methanesulfonate group with sodium azide readily provides the 7-azido analogue compound 5. Acid-mediated hydrolysis of the methyl glycoside and acetal moieties in compound 5 using aqueous p-toluenesulfonic acid (TsOH) provides compound 6. Treatment of compound 6 with acetyl chloride provides the per-O-acetylated glycosyl chloride product compound 7. Treatment of compound 7 with the sodium salt of numerous substituted hydroxy aromatic compounds will provide the key intermediates to the desired targets, compounds 8. Generation of the sodium salt is accomplished with sodium hydride in tetrahydrofuran. Subsequent de-O-acetylation and de-esterification of the resulting intermediates is accomplished with an aqueous sodium hydroxide solution and workup involving acidification of the reaction medium. Subsequent hydrogenation of the azido moiety in the presence of palladium-on-carbon catalyst, in the usual manner, gives the 7-amino compounds 9. This provides access to the 4-O-alkyl 7-substituted analogues from General Structure I.

It should be noted that compound 9a, wherein $R^3$=CHO, can readily be converted to provide compound 9b, wherein $R^3$=CH=CHNO₂, (for structures, see Table 1) according to a standard procedure employing nitromethane, ammonium acetate, and acetic acid in ethanol under reflux. This procedure has been utilized in the preparation of nitrovinyl analogues of other monosaccharides (Patel and Richardson, 1986; Aamlid, et al., 1990) as chromogenic substrates for the assay of glycosidases; however, none of the products or intermediates described herein are contained in the aforementioned references.

It should also be noted that compound 9c (for structure, see Table 2) can readily be prepared using the procedure outline in FIG. 1, by employing the di-sodium salt of commercially available thymolphthalein in the conversion of compound 7 to compound 8. The di-sodium salt of thymolphthalein is generated using sodium hydride in tetrahydrofuran as described for numerous hydroxy aromatic compounds.

4-O-Alkyl 7,9-Di-substituted Analogues From General Structure I

Figure 2:
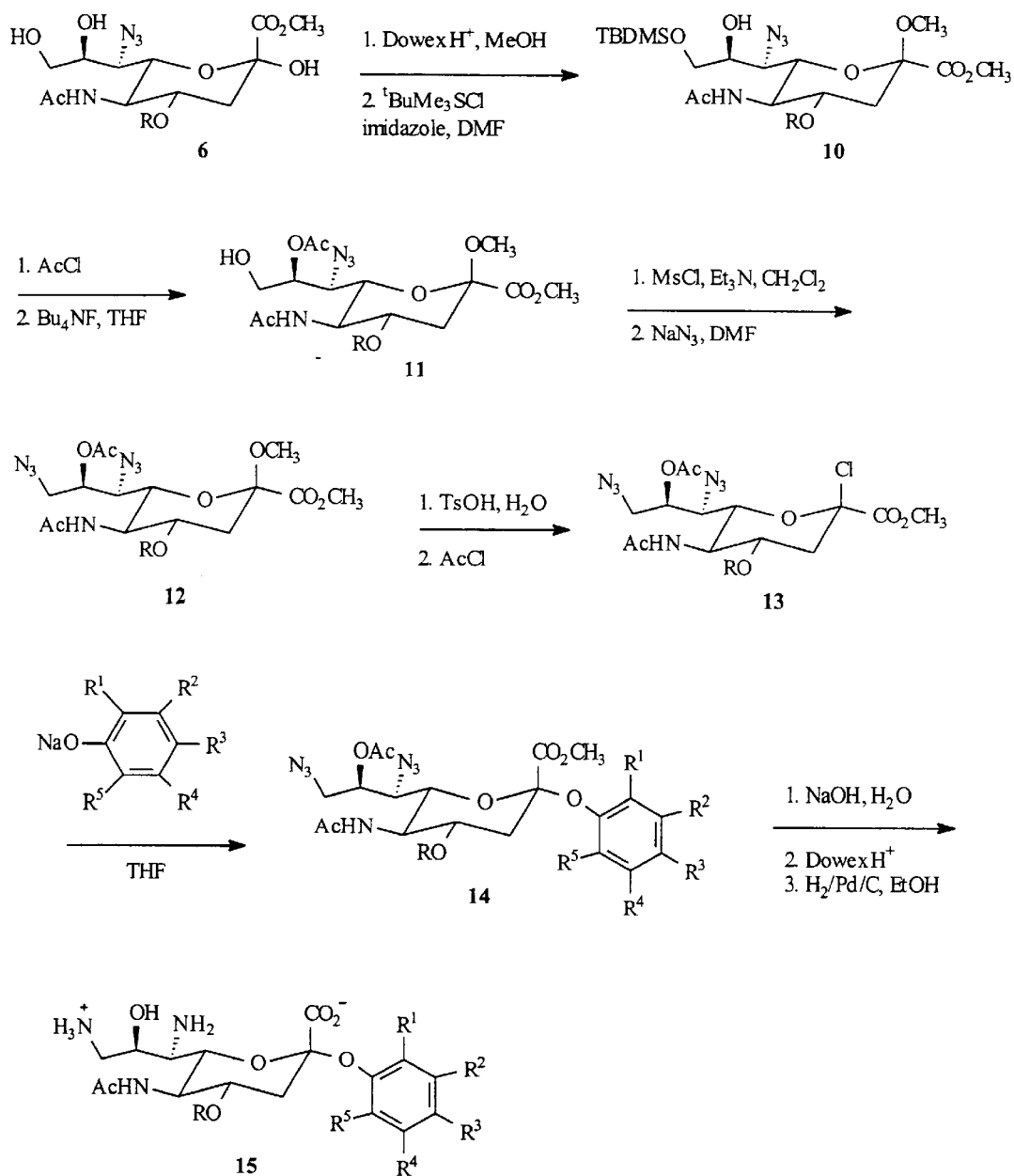
FIG. 2—synthetic approaches for selected 4-O-alkyl 7,9-disubstituted examples from General Structure I are summarized in this reaction scheme.

FIG. 2 illustrates constructing a basic skeleton of General Structure I via the conversion of compound 6 to compound 10 via acid-mediated methyl glycoside formation, followed by 9-O-silylation using tert-butyldimethylsilyl chloride ($^t$BuMe$_2$SiCl). Compound 6 is prepared according to the procedure outlined in FIG. 1. Acetylation of the 8-hydroxyl group with acetyl chloride under standard conditions, followed by de-silylation with tetra-butyl ammonium fluoride (Bu$_4$NF) readily provides the 9-hydroxy analogue 11. Compound 11, with a free 9-hydroxyl group, is then activated for displacement via the methanesulfonate intermediate by reaction of 11 with methanesulfonyl chloride (MsCl) in the presence of base. Nucleophilic displacement of the methanesulfonate group with sodium azide readily provides the 9-azido analogue compound 12. Acid-mediated hydrolysis of the methyl glycoside in compound 12 using aqueous p-toluenesulfonic acid (TsOH), followed by acetylation and glycosyl chloride generation using acetyl chloride provides compound 13. Treatment of compound 13 with the sodium salt of numerous substituted hydroxy aromatic compounds gives the key intermediates to the desired targets, compounds 14. Generation of the sodium salt is accomplished with sodium hydride in tetrahydrofuran. Subsequent de-O-acetylation and de-esterification of the resulting intermediates is accomplished with an aqueous sodium hydroxide solution and workup involving acidification of the reaction medium. Subsequent hydrogenation of the azido moieties in the presence of palladium-on-carbon catalyst, in the usual manner, gives the 7,9-di-amino compounds 15. This provides access to the 4-O-alkyl 7,9-di-substituted analogues from General Structure I.

It should be noted that compound 15a, wherein R$^3$=CHO, can readily be converted to provide a compound 15b, wherein R$^3$=CH=CHNO$_2$, (for structures, see Table 1) according to a standard procedure employing nitromethane, ammonium acetate, and acetic acid in ethanol under reflux. This procedure has been utilized in the preparation of nitrovinyl analogues of other monosaccharides (Patel and Richardson, 1986; Aamlid, et al., 1990) as chromogenic substrates for the assay of glycosidases; however, none of the products or intermediates described herein are contained in the aforementioned references.

It should also be noted that compound 15c (for structure, see Table 2) can readily be prepared using the procedure outline in FIG. 2, by employing the di-sodium salt of commercially available thymolphthalein in the conversion of compound 13 to compound 14. The di-sodium salt of thymolphthalein is generated using sodium hydride in tetrahydrofuran as described for numerous hydroxy aromatic compounds.

4,7-Di-O-alkyl 9-Substituted Analogues From General Structure I

Figure 3:
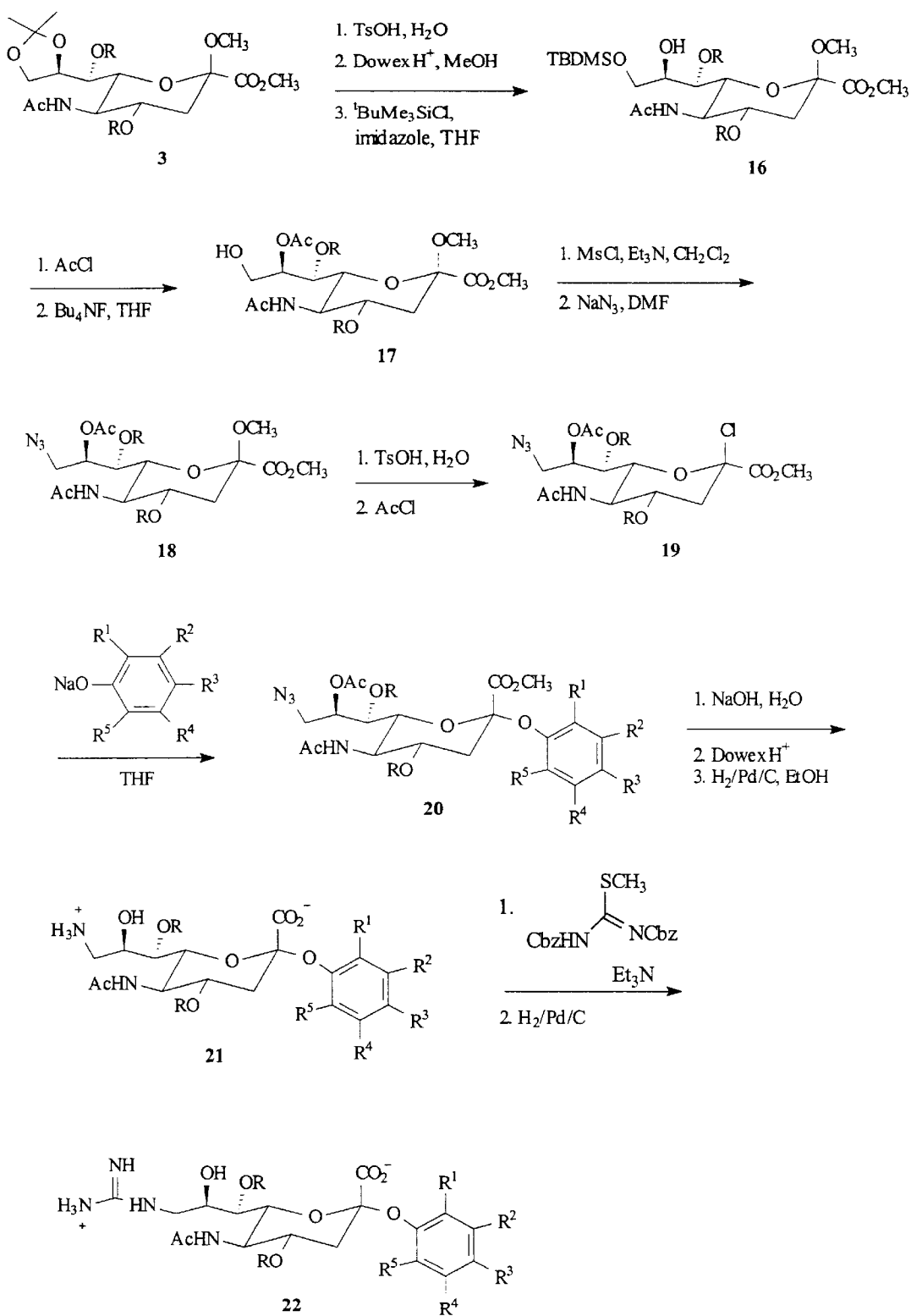
FIG. 3—synthetic approaches for selected 4,7-di-O-alkyl 9-substituted examples from General Structure I are summarized in this reaction scheme.

FIG. 3 illustrates constructing a basic skeleton of General Structure I via the conversion of compound 3 to compound 16 via acid-mediated methyl glycoside formation, followed by re-generation of the methyl glycoside moiety using acid-mediated means in methanol and 9-O-silylation using tert-butyldimethylsilyl chloride ($^t$BuMe$_2$SiCl). Compound 3 is prepared according to the procedure outlined in FIG. 1. Subsequent acetylation of the 8-hydroxyl group in 16 with acetyl chloride, followed by de-silylation with tetra-butylammonium fluoride (Bu$_4$NF) gives compound 17. Compound 17, with a free 9-hydroxyl group, is then activated for displacement via the methanesulfonate intermediate by reaction of 17 with methanesulfonyl chloride (MsCl) in the presence of base. Nucleophilic displacement of the methanesulfonate group with sodium azide readily provides the 9-azido analogue compound 18. Acid-mediated hydrolysis of the methyl glycoside in compound 18 using aqueous p-toluenesulfonic acid (TsOH), followed by acetylation and glycosyl chloride generation using acetyl chloride provides compound 19. Treatment of compound 19 with the sodium salt of numerous substituted hydroxy aromatic compounds provides the key intermediates to the desired targets. Generation of the sodium salt is accomplished with sodium hydride in tetrahydrofuran. Subsequent de-O-acetylation and de-esterification of the resulting intermediates is accomplished with an aqueous sodium hydroxide solution and workup involving acidification of the reaction medium. Subsequent hydrogenation of the azido moiety in the presence of palladium-on-carbon catalyst, in the usual manner, gives the 9-amino compounds 21. Treatment of 21 with N,N'-bis-tert-benzyloxycarbonyl-2-methyl-2-thiopseudourea in dichloromethane under standard conditions, followed by subsequent hydrogenation using palladium-on-carbon catalyst gives the 9-guanidino compounds 22. This provides access to the 4,7-Di-O-alkyl 9-substituted analogues from General Structure I.

It should be noted that compounds 21a and 22a, wherein R$^3$=CHO, can readily be converted to the respective compounds 21b and 22b, wherein R$^3$=CH=CHNO$_2$, (for structures, see Table 1) according to a standard procedure employing nitromethane, ammonium acetate, and acetic acid: in ethanol under reflux. This procedure has been utilized in the preparation of nitrovinyl analogues of other monosaccharides (Patel and Richardson, 1986; Aamlid, et al., 1990) as chromogenic substrates for the assay of glycosidases; however, none of the products or intermediates described herein are contained in the aforementioned references.

It should also be noted that compounds 21c and 22c (for structure, see Table 2) can readily be prepared using the procedure outline in FIG. 3, by employing the di-sodium salt of commercially available thymolphthalein in the conversion of compound 19 to compound 20. The di-sodium salt of thymolphthalein is generated using sodium hydride in tetrahydrofuran as described for numerous hydroxy aromatic compounds.

4-Substituted Analogues From General Structure I

Figure 4:
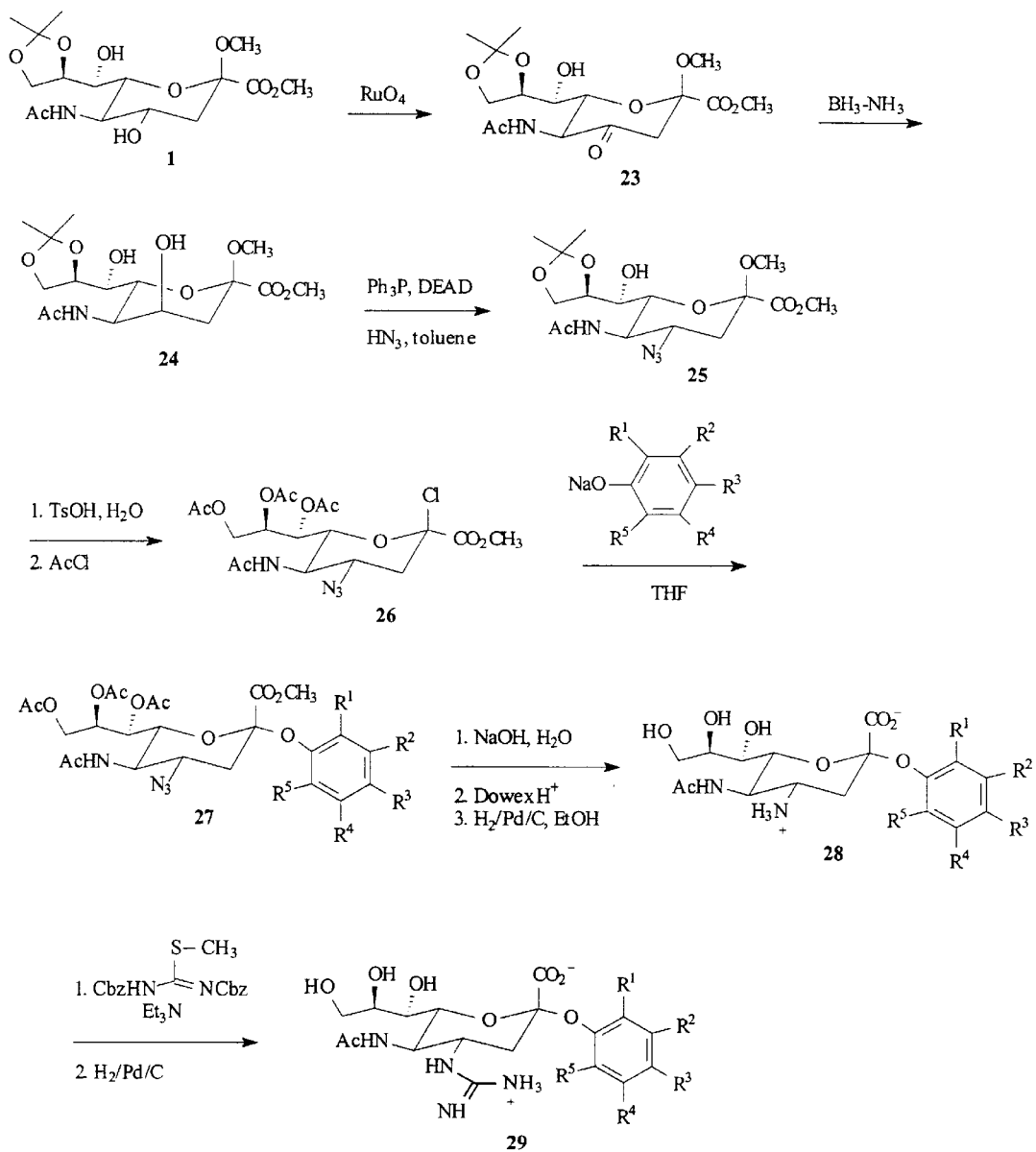
FIG. 4—synthetic approaches for selected 4-substituted examples from General Structure I are summarized in this reaction scheme.

FIG. 4 illustrates constructing a basic skeleton of General Structure I via the regioselective oxidation of the 4-hydroxyl group in compound 1 using ruthenium tetroxide under conditions reported previously (Zbiral, et al., 1989) for the same compound. Compound 1 is generally prepared according to known procedures (Kim, 1988; Liav, 1996; Hartman and Zbiral, 1989). Diastereoselective reduction of the 4-ketone group in compound 23 with borane-ammonia gives the 4-epi-sialic acid analogue 24. Compound 24, with free 4- and 7-hydroxyl groups, is then regioselectively activated for displacement at C-4 via treatment with triphenylphosphine (Ph$_3$P) and diethylazodicarboxylate (DEAD) in toluene, followed by the subsequent treatment with HN$_3$ in toluene to give the 4-azido compound 25. This two-step transformation of compound 24 to compound 25 has been reported for the preparation of the same compound (Zbiral, et al., 1989). Acid-mediated hydrolysis of the methyl glycoside and acetal moieties in compound 25 using aqueous p-toluenesulfonic acid (TsOH), followed by per-O-acetylation and glycosyl chloride generation using acetyl chloride gives compound 26. Treatment of compound 26 with the sodium salt of numerous substituted hydroxy aromatic compounds provides the key intermediates to the desired targets, compounds 27. Generation of the sodium salt is accomplished with sodium hydride in tetrahydrofuran. Subsequent de-O-acetylation and de-esterification of the resulting intermediates is accomplished with an aqueous sodium hydroxide solution and workup involving acidification of the reaction medium. Hydrogenation of the azido moiety in the presence of palladium-on-carbon catalyst, in the usual manner, gives the 4-amino compounds 28. Treatment of 28 with N,N'-bis-tert-benzyloxycarbonyl-2-methyl-2-thiopseudourea in dichloromethane under standard conditions, followed by subsequent hydrogenation using palladium-on-carbon catalyst gives the 4-guanidino compounds 29. This provides access to the 4-substituted analogues from General Structure I.

It should be noted that compound 28a and 29a, wherein $R^3$=CHO, can readily be converted to the respective compounds 28b and 29b, wherein $R^3$=CH=CHNO$_2$, (for structures, see Table 1) according to a standard procedure employing nitromethane, ammonium acetate, and acetic acid in ethanol under reflux. This procedure has been utilized in the preparation of nitrovinyl analogues of other monosaccharides (Patel and Richardson, 1986; Aamlid, et al., 1990) as chromogenic substrates for the assay of glycosidases; however, none of the products or intermediates described herein are contained in the aforementioned references.

It should also be noted that compounds 28c and 29c (for structure, see Table 2) can readily be prepared using the procedure outline in FIG. 4, by employing the di-sodium salt of commercially available thymolphthalein in the conversion of compound 26 to compound 27. The di-sodium salt of thymolphthalein is generated using sodium hydride in tetrahydrofuran as described for numerous hydroxy aromatic compounds.

B. Compounds with General Structure II and their salts and derivatives, may be prepared using any of several methods known in the art for the synthesis of substituted sialic acid analogs containing analogous structures.

To illustrate, synthetic approaches for selected examples of 4-, 4,7-, and 4,7,9-position modified analogues of General Structure II are summarized in FIGS. 5–8. These synthetic approaches are representative of the types of procedures that can be employed.

It should be noted that the present invention relates to chromogenic substrate compounds that are useful in the detection of sialidase. As such, the present invention relates to chromogenic substrate compounds in addition to those presented in FIGS. 5–8. Likewise, numerous other analogues with varying $R^1$, $R^2$, $R^3$, $R^6$, $R^7$, and/or $R^8$, as defined in the Summary of the Invention, can be prepared using analogous or altogether different methods.

4-O-Alkyl 7-Substituted Analogues From General Structure II

Figure 5:
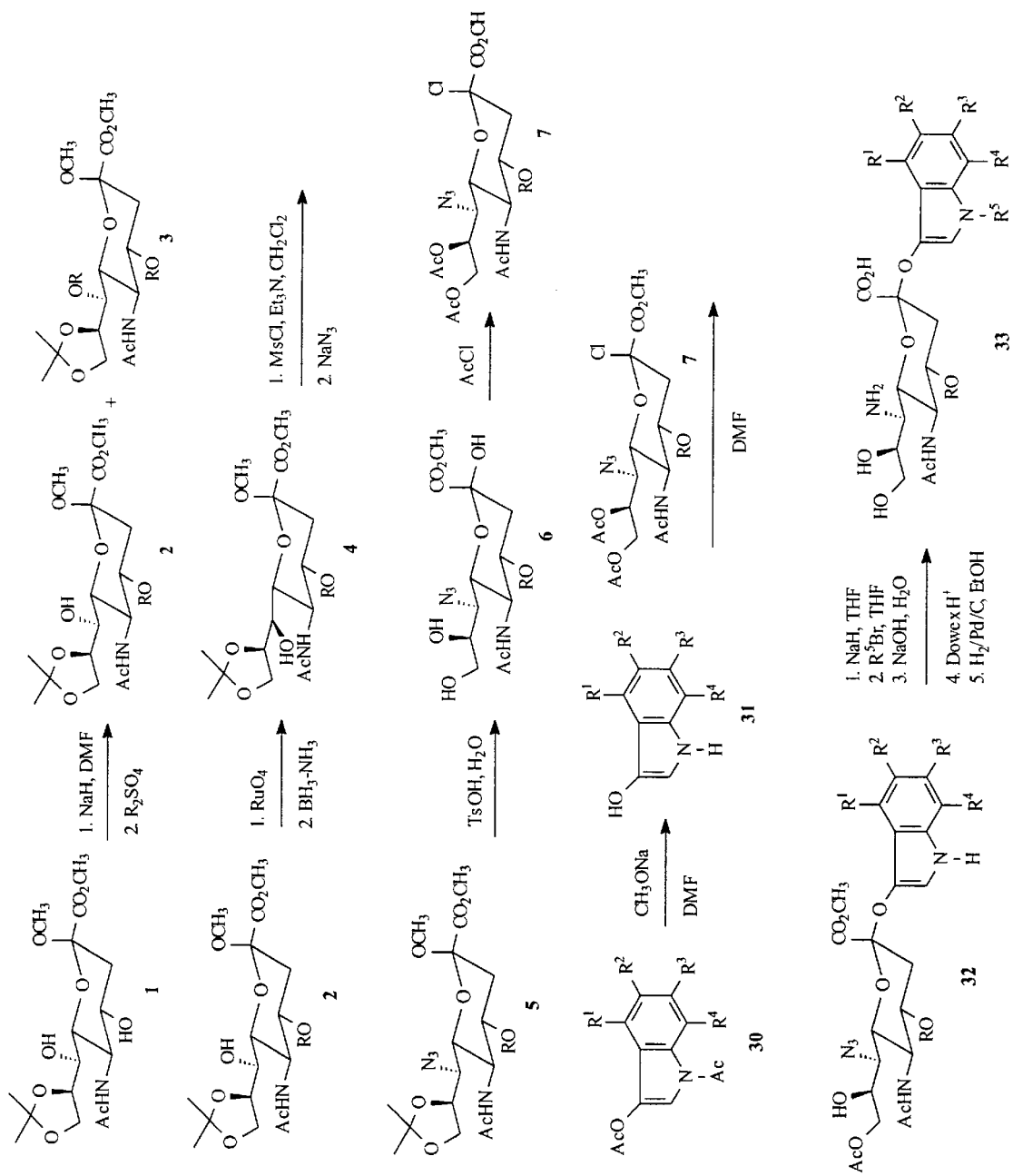
FIG. 5—synthetic approaches for selected 4-O-alkyl 7-substituted examples from General Structure II are summarized in this reaction scheme.

FIG. 5 illustrates constructing a basic skeleton of General Structure II via O-alkylation of methyl 8,9-O-isopropylidene-2-O-methyl-Neu5Ac (1) using conditions previously reported (Liav, 1998) for the same compound. Compound 1 is generally prepared according to known procedures (Kim, 1988; Liav, 1996; Hartman and Zbiral, 1989). O-Alkylation of 1 using any of a series of dialkyl sulfate analogues including dimethyl sulfate, diethyl sulfate, diisopropyl sulfate, among others, provides the 4-O-alkyl compound 2 and the 4,7-di-O-alkyl compound 3 as a separable mixture on chromatography. Treatment of compound 2 with ruthenium tetroxide provides the intermediate 7-keto analogue, followed by subsequent diastereoselective reduction with borane-ammonia gives the 7-epi-sialic acid analogue 4. Compound 4, with a free 7-hydroxyl group, is then activated for displacement via the methanesulfonate intermediate by reaction of 4 with methanesulfonyl chloride (MsCl) in the presence of organic base. Nucleophilic displacement of the methanesulfonate group with sodium azide readily provides the 7-azido analogue compound 5. Acid-mediated hydrolysis of the methyl glycoside and acetal moieties in compound 5 using aqueous p-toluenesulfonic acid (TsOH) provides compound 6. Treatment of compound 6 with acetyl chloride provides the per-O-acetylated glycosyl chloride product compound 7.

Treatment of any of numerous substituted indoxyl 1,3-diacetate compounds (compounds 30) with sodium methoxide in anhydrous N,N-dimethylformamide readily provides the modified 3-hydroxy indole compounds 31. This procedure has been utilized in the preparation of 5-bromo-3-hydroxy indole (compound 31, wherein, $R^1$=$R^3$=$R^4$=H and $R^2$=Br)(Eschenfelder and Brossmer, *Glycoconjugate J.*, 1987). Subsequent treatment of compound 31 with compound 7 in anhydrous N,N-dimethylformamide provides the desired modified indole O-glycoside compounds 32, according to a known procedure for the preparation of methyl N-acetyl-4,7,8,9-tetra-O-acetyl-2-O-(5-bromoindol-3-yl)-(-D-neuriminate (Eschenfelder and Brossmer, *Glycoconjugate J.*, 1987). Analogously, 3-indolyl O-glycosides of other monosaccharides have been prepared using these and alternate conditions (Robertson, 1927; Freudenberg, et al., 1952; Horwitz, et al., 1964; Ley, et al., 1987); however, none of the products or intermediates described herein are contained in the aforementioned references. Treatment of compound 32 with sodium hydride in tetrahydrofuiran, followed with an alkyl halide ($R^5$Br) provides the N-alkylated intermediates. Subsequent de-O-acetylation and de-esterification of the resulting intermediates is accomplished with an aqueous sodium hydroxide solution and workup involving acidification of the reaction medium. Hydrogenation of the azido moiety in the presence of palladium-on-carbon catalyst, in the usual manner, gives the 7-amino compounds 33. This provides access to the 4-O-alkyl 7-substituted analogues from General Structure II.

4-O-Alkyl 7,9-di-Substituted Analogues From General Structure II

Figure 6:
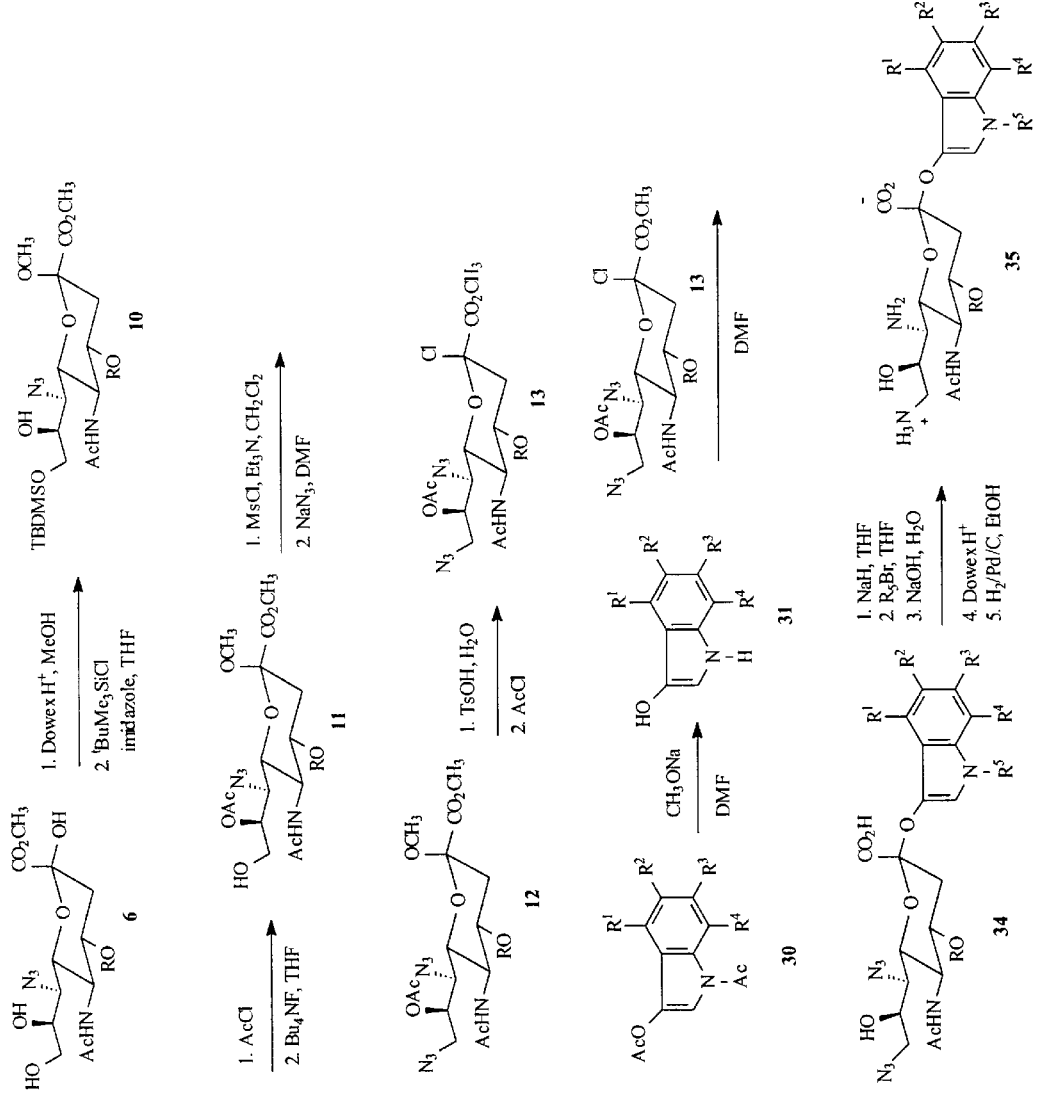
FIG. 6—synthetic approaches for selected 4-O-alkyl 7,9-disubstituted examples from General Structure II are summarized in this reaction scheme.

FIG. 6 illustrates constructing a basic skeleton of General Structure II via the conversion of compound 6 to compound 10 via acid-mediated methyl glycoside formation, followed by 9-O-silylation using tert-butyldimethylsilyl chloride ('BuMe$_2$SiCl). Compound 6 is prepared according to the procedure outlined in FIG. 1. Acetylation of the 8-hydroxyl group with acetyl chloride under standard conditions, followed by de-silylation with tetra-butyl ammonium fluoride (Bu$_4$NF) readily provides the 9-hydroxy analogue 11. Compound 11, with a free 9-hydroxyl group, is then activated for displacement via the methanesulfonate intermediate by reaction of 11 with methanesulfonyl chloride (MsCl) in the presence of base. Nucleophilic displacement of the methanesulfonate group with sodium azide readily provides the 9-azido analogue compound 12. Acid-mediated hydrolysis of the methyl glycoside in compound 12 using aqueous p-toluenesulfonic acid (TsOH), followed by acetylation and glycdsyl chloride generation using acetyl chloride provides compound 13.

Treatment of any of numerous substituted indoxyl 1,3-diacetate compounds (compound 30) with sodium methoxide in anhydrous N,N-dimethylformamide readily provides the modified 3-hydroxy indole compound 31. This procedure has been utilized in the preparation of 5-bromo-3-hydroxy indole (compound 31, wherein, $R^1=R^3=R^4=H$ and $R^2=Br$) (Eschenfelder and Brossmer, *Glycoconjugate J.*, 1987). Subsequent treatment of compound 34 with compound 13 in anhydrous N,N-dimethylformamide provides the desired modified indole O-glycoside compounds 34, according to a known procedure for the preparation of methyl N-acetyl-4,7,8,9-tetra-O-acetyl-2-O-(5-bromoindol-3-yl)-(-D-neuriminate (Eschenfelder and Brossmer, *Glycoconjugate J.*, 1987). Analogously, 3-indolyl O-glycosides of other monosaccharides have been prepared using these and alternate conditions (Robertson, 1927; Freudenberg, et al., 1952; Horwitz, et al., 1964; Ley, et al., 1987); however, none of the products or intermediates described herein are contained in the aforementioned references. Treatment of compound 34 with sodium hydride in tetrahydrofuran, followed with an alkyl halide ($R^5Br$) provides the N-alkylated intermediates. Subsequent de-O-acetylation and de-esterification of the resulting intermediates is accomplished with an aqueous sodium hydroxide solution and workup involving acidification of the reaction medium. Hydrogenation of the azido moiety in the presence of palladium-on-carbon catalyst, in the usual manner, gives the 7,9-di-amino compounds 35. This provides access to the 4-O-alkyl 7,9-di-substituted analogues from General Structure II.

4,7-di-O-Alkyl 9-Substituted Analogues From General Structure II

Figure 7:
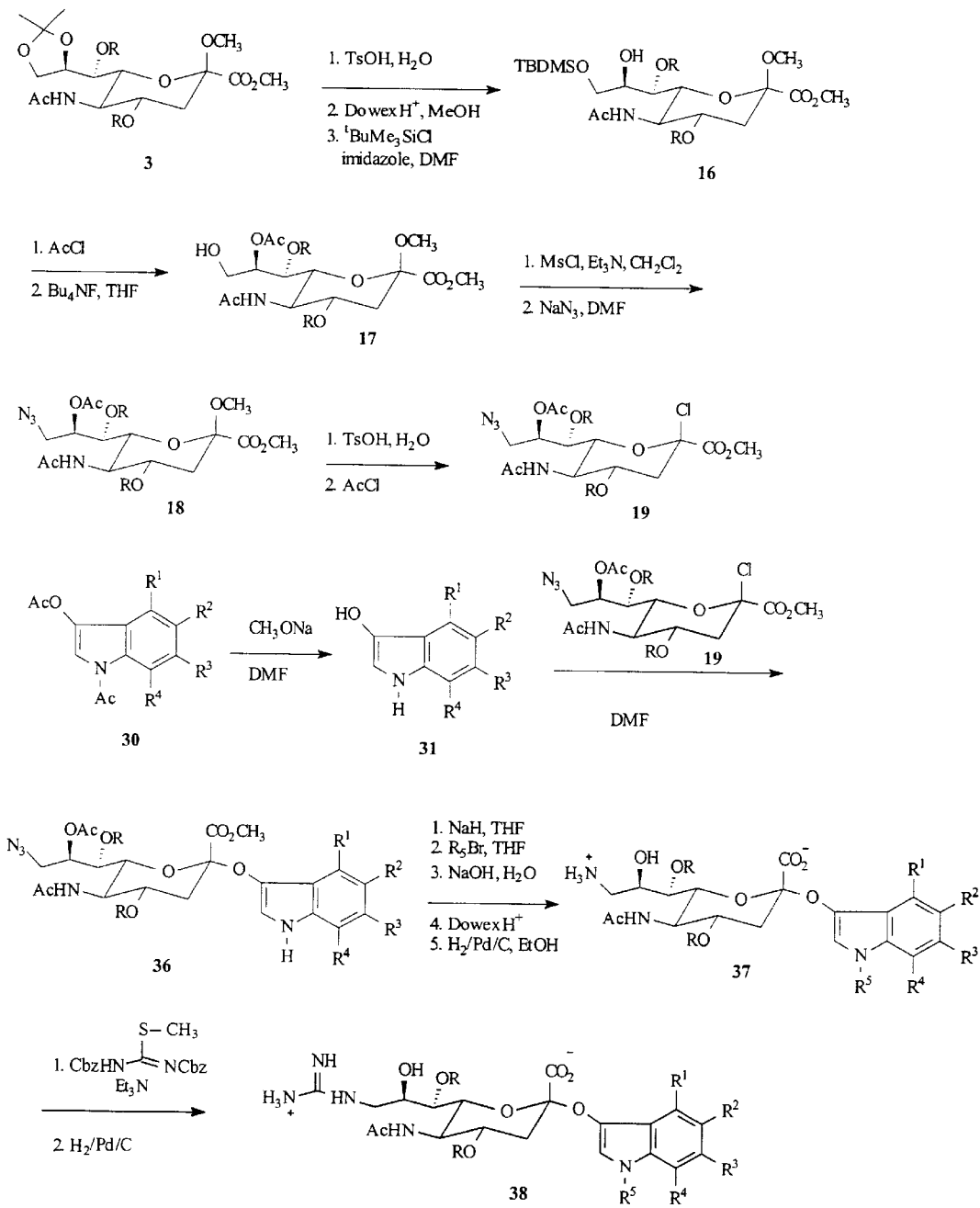
FIG. 7—synthetic approaches for selected 4,7-di-O-alkyl 9-substituted examples from General Structure II are summarized in this reaction scheme.

FIG. 7 illustrates constructing a basic skeleton of General Structure II via the conversion of compound 3 to compound 16 via acid-mediated methyl glycoside formation, followed by re-generation of the methyl glycoside moiety using acid-mediated means in methanol and 9-O-silylation using tert-butyldimethylsilyl chloride ($^t$BuMe$_2$SiCl). Compound 3 is prepared according to the procedure outlined in FIG. 1. Subsequent acetylation of the 8-hydroxyl group in 16 with acetyl chloride, followed by de-silylation with tetrabutylammonium fluoride (Bu$_4$NF) gives compound 17. Compound 17, with a free 9-hydroxyl group, is then activated for displacement via the methanesulfonate intermediate by reaction of 17 with methanesulfonyl chloride (MsCl) in the presence of base. Nucleophilic displacement of the methanesulfonate group with sodium azide readily provides the 9-azido analogue compound 18. Acid-mediated hydrolysis of the methyl glycoside in compound 18 using aqueous p-toluenesulfonic acid (TsOH), followed by acetylation and glycosyl chloride generation using acetyl chloride provides compound 19.

Treatment of any of numerous substituted indoxyl 1,3-diacetate compounds (compounds 30) with sodium methoxide in anhydrous N,N-dimethylformamide readily provides the modified 3-hydroxy indole compounds 31. This procedure has been utilized in the preparation of 5-bromo-3-hydroxy indole (compound 31, wherein, $R^1=R^3=R^4=H$ and $R^2=Br$) (Eschenfelder and Brossmer, *Glycoconjugate J.*, 1987). Subsequent treatment of compound 31 with compound 19 in anhydrous N,N-dimethylformamide provides the desired modified indole O-glycoside compounds 36, according to a known procedure for the preparation of methyl N-acetyl-4,7,8,9-tetra-O-acetyl-2-O-(5-bromoindol-3-yl)-(-D-neuriminate (Eschenfelder and Brossmer, *Glycoconjugate J.*, 1987). Analogously, 3-indolyl O-glycosides of other monosaccharides have been prepared using these arid alternate conditions (Robertson, 1927; Freudenberg, et al., 1952; Horwitz, et al., 1964; Ley, et al., 1987); however, none of the products or intermediates described herein are contained in the aforementioned references. Treatment of compound 36 with sodium hydride in tetrahydrofuran, followed with an alkyl halide ($R^5Br$) provides the N-alkylated intermediates. Subsequent de-O-acetylation and de-esterification of the resulting intermediates is accomplished with an aqueous sodium hydroxide solution and workup involving acidification of the reaction medium. Finally, hydrogenation of the azido moiety in the presence of palladium-on-carbon catalyst, in the usual manner, gives the 9-amino compounds 37. Treatment of 37 with N,N'-bis-tert-benzyloxycarbonyl-2-methyl-2-thiopseudourea in dichloromethane under standard conditions, followed by subsequent hydrogenation using palladium-on-carbon catalyst gives the 4-guanidino compounds 38. This provides access to the 4,7-O-alkyl 9-substituted analogues from General Structure II.

4-Substituted Analogues From General Structure II

Figure 8:
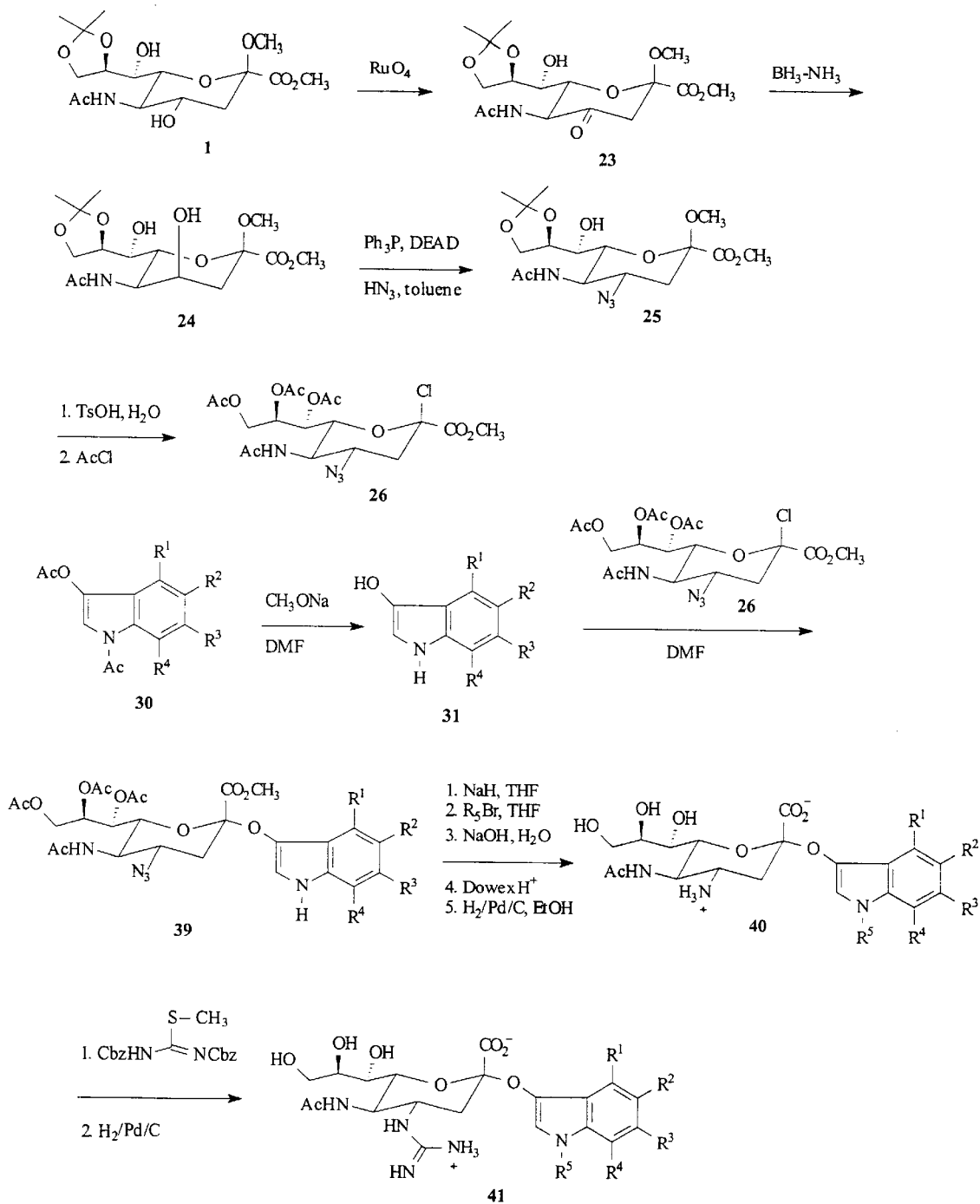
FIG. 8—synthetic approaches for selected 4-substituted examples from General Structure II are summarized in this reaction scheme.

FIG. 8 illustrates constructing a basic skeleton of General Structure II via the regioselective oxidation of the 4-hydroxyl group in compound 1 using ruthenium tetroxide under conditions reported previously (Zbiral, et al., 1989) for the same compound. Compound 1 is generally prepared according to known procedures (Kim, 1988; Liav, 1996; Hartman and Zbiral, 1989). Diastereoselective reduction of the 4-ketone group in compound 23 with borane-ammonia gives the 4-epi-sialic acid analogue 24. Compound 24, with free 4- and 7-hydroxyl groups, is then regioselectively activated for displacement at C-4 via treatment with triphenylphosphine (Ph$_3$P) and diethylazodicarboxylate (DEAD) in toluene, followed by the subsequent treatment with HN$_3$ in toluene to give the 4-azido compound 25. This two-step transformation of compound 24 to compound 25 has been reported for the preparation of the same compound (Zbiral, et al., 1989). Acid-mediated hydrolysis of the methyl glycoside and acetal moieties in compound 25 using aqueous p-toluenesulfonic acid (TsOH), followed by per-O-acetylation and glycosyl chloride generation using acetyl chloride gives compound 26.

Treatment of any of numerous substituted indoxyl 1,3-diacetate compounds (compound 30) with sodium methoxide in anhydrous. N, N-dimethylformamide readily provides the modified 3-hydroxy indole compound 31. This procedure has been utilized in the preparation of 5-bromo-3-hydroxy indole (compound 31, wherein, $R^1=R^3=R^4=H$ and $R^2=Br$) (Eschenfelder and Brossmer, *Glycoconjugate J.*, 1987). Subsequent treatment of compound 31 with compound 26 in anhydrous N,N-dimethylformamide provides the desired modified indole O-glycoside compounds 36, according to a known procedure for the preparation of methyl N-acetyl-4,7,8,9-tetra-O-acetyl-2-O-(5-bromoindol-3-yl)-(-D-neuriminate (Eschenfelder and Brossmer, *Glycoconjugate J.*, 1987). Analogously, 3-indolyl O-glycosides of other monosaccharides have been prepared using these and alternate conditions (Robertson, 1927; Freudenberg, et al., 1952; Horwitz, et al., 1964; Ley, et al., 1987); however, none of the products or intermediates described herein are contained in the aforementioned references. Treatment of compound 39 with sodium hydride in tetrahydrofuran, followed with an alkyl halide ($R^5Br$) provides the N-alkylated intermediates. Subsequent de-O-acetylation and de-esterification of the resulting intermediates is accomplished with an aqueous sodium hydroxide solution and workup involving acidification of the reaction medium. Finally, hydrogenation of the azido moiety in the presence of palladium-on-carbon catalyst, in the usual manner, gives the 4-amino compounds 40. Treatment of 40 with N,N'-bis-tert-benzyloxycarbonyl-2-methyl-2-thiopseudourea in dichloromethane under standard conditions, followed by subsequent hydrogenation using palladium-on-carbon catalyst gives the 4-guanidino compounds 41. This provides access to the 4-substituted analogues from General Structure II.

C. Compounds with General Structures IIIa and IIIb and their salts and derivatives, may be prepared using any of several methods known in the art for the synthesis of substituted sialic acid analogs containing analogous structures.

To illustrate, synthetic approaches for selected examples of 4-, 4,7-, and 4,7,9-position modified analogues of General Structures IIIa and IIIb are summarized in FIGS. 9–12. These synthetic approaches are representative of the types of procedures that can be employed.

It should be noted that the present invention relates to chromogenic substrate compounds that are useful in the detection of sialidase. As such, the present invention relates to chromogenic substrate compounds in addition to those presented in FIGS. 9–12. Likewise, numerous other analogues with varying $R^1$, $R^2$, $R^3$, $R^6$, $R^7$, and/or $R^8$, as defined in the Summary of the Invention, can be prepared using analogous or altogether different methods.

4-O-Alkyl 7-Substituted Analogues From General Structures IIIa and IIIb

Figure 9:
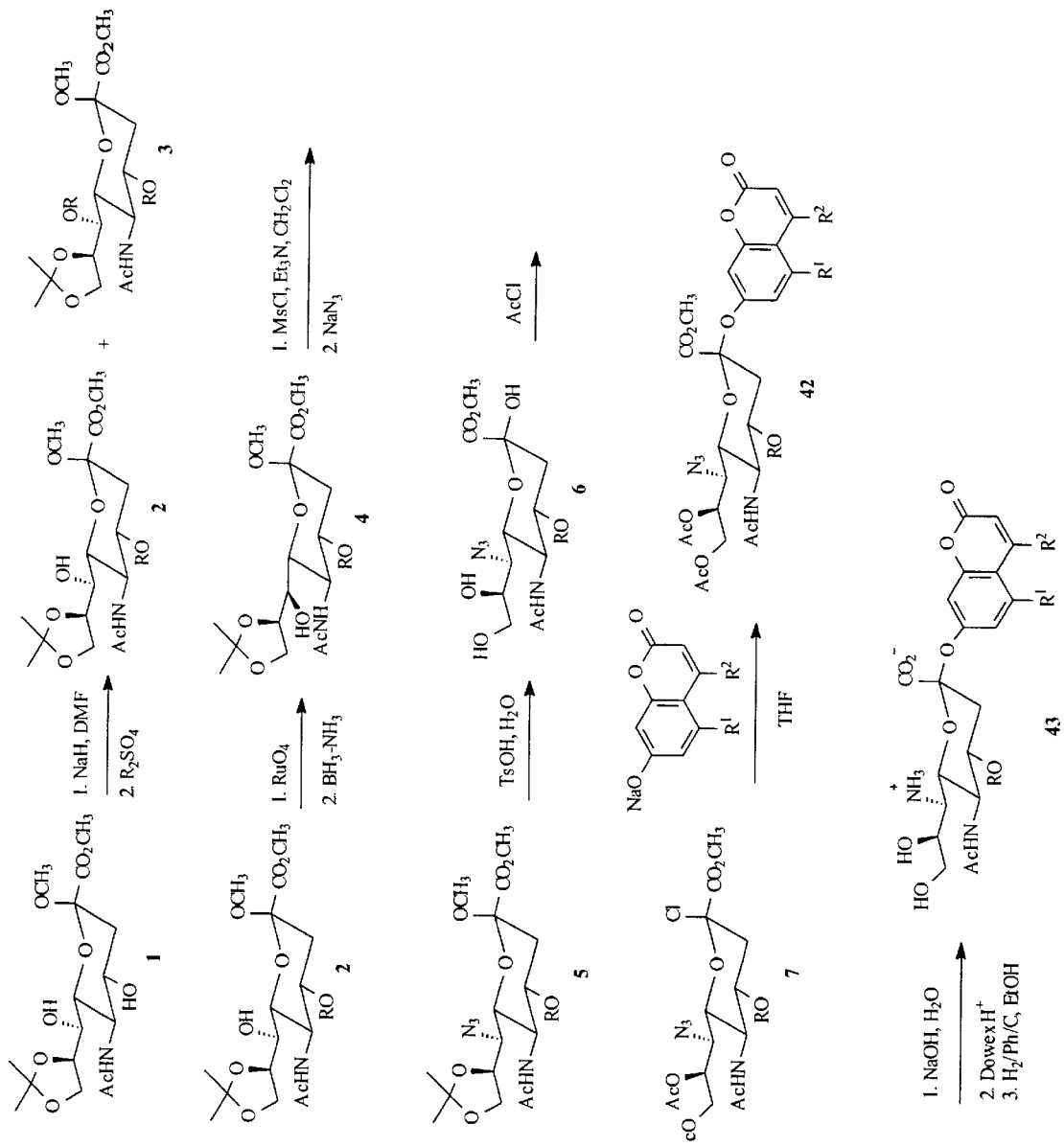
FIG. 9—synthetic approaches for selected 4-O-alkyl 7-substituted examples from General Structures IIIa and IIIb are summarized in this reaction scheme.

FIG. 9 illustrates constructing a basic skeleton of General Structures IIIa and IIIb via O-alkylation of methyl 8,9-O-isopropylidene-2-O-methyl-Neu5Ac (1) using conditions previously reported (Liav, 1998) for the same compound. Compound 1 is generally prepared according to known procedures (Kim, 1988; Liav, 1996; Hartman and Zbiral, 1989). O-Alkylation of 1 using any of a series of dialkyl sulfate analogues including dimethyl sulfate, diethyl sulfate, diisopropyl sulfate, among others, would provide the 4-O-alkyl compound 2 and the 4,7-di-O-alkyl compound 3 as a separable mixture on chromatography. Treatment of compound 2 with ruthenium tetroxide provides the intermediate 7-keto analogue, followed by subsequent diastereoselective reduction with borane-ammonia gives the 7-epi-sialic acid analogue 4. Compound 4, with a free 7-hydroxyl group, is then activated for displacement via the methanesulfonate intermediate by reaction of 4 with methanesulfonyl chloride (MsCl) in the presence of organic base. Nucleophilic displacement of the methanesulfonate group with sodium azide readily provides the 7-azido analogue compound 5. Acid-mediated hydrolysis of the methyl glycoside and acetal moieties in compound 5 using aqueous p-toluenesulfonic acid (TsOH) will provide compound 6. Treatment of compound 6 with acetyl chloride provides the per-O-acetylated glycosyl chloride product compound 7.

Treatment of compound 7 with the sodium salt of numerous substituted coumarin derivatives provides the key intermediates to the desired targets (compounds 42). Generation of the sodium salt is accomplished with sodium hydride in tetrahydrofuran. This method of O-glycosylation has already been applied in the stereoselective preparation of numerous O-glycosides of N-acetyl-D-neuraminic acid (Myers, et al., 1980; Eschenfelder and Brossmer, Carbohydr. Res., 1987; Eschenfelder and Brossmer, Glycoconjugate J., 1987; Okamoto and Goto, 1990; Warner and O'Brien, 1979) derived from aromatic hydroxyls. However, none of the products described herein are contained in the aforementioned references. Subsequent de-O-acetylation and de-esterification of compounds 42 is accomplished with an aqueous sodium hydroxide solution and workup involving acidification of the reaction medium. Finally, hydrogenation of the azido moiety in the presence of palladium-on-carbon catalyst, in the usual manner, gives the 7-amino compounds 43. This provides access to the 4-O-alkyl 7-substituted analogues from General Structure IIIa and IIIb.

Figure 10:
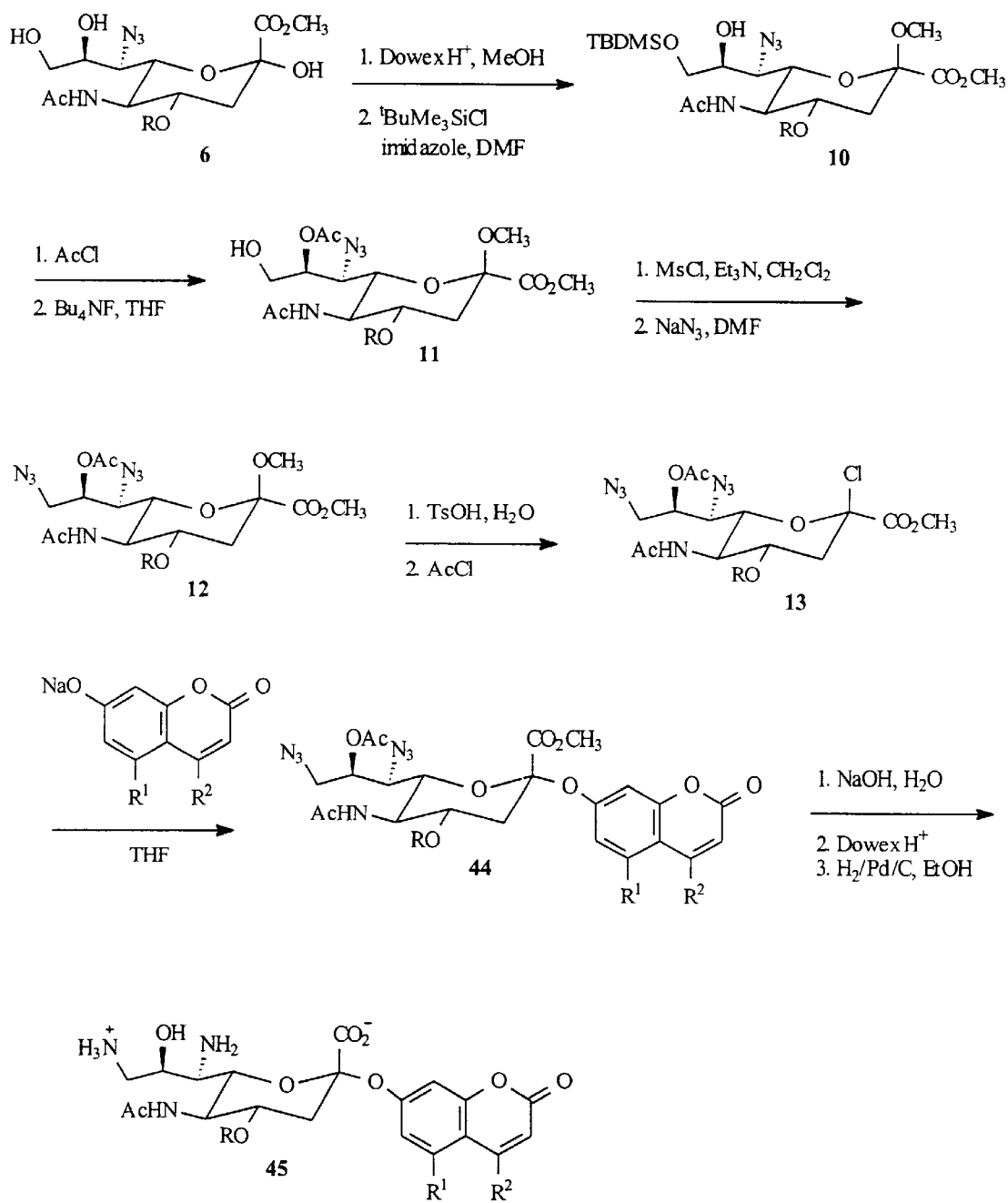
FIG. 10—synthetic approaches for selected 4-O-alkyl 7,9-disubstituted examples from General Structures IIIa and IIIb are summarized in this reaction scheme.

4-O-Alkyl 7,9-di-Substituted Analogues From General Structures IIIa and IIIb FIG. 10 illustrates constructing a basic skeleton of General Structures IIIa and IIIb via the conversion of compound 6 to compound 10 via acid-mediated methyl glycoside formation, followed by 9-O-silylation using tert-butyldimethylsilyl chloride ($^tBuMe_2SiCl$). Compound 6 is prepared according to the procedure outlined in FIG. 1. Acetylation of the 8-hydroxyl group with acetyl chloride under standard conditions, followed by De-silylation with tetra-butyl ammonium fluoride ($Bu_4NF$) readily provides the 9-hydroxy analogue 11. Compound 11, with a free 9-hydroxyl group, is then activated for displacement via the methanesulfonate intermediate by reaction of 11 with methanesulfonyl chloride (MsCl) in the presence of base. Nucleophilic displacement of the methanesulfonate group with sodium azide will readily provide the 9-azido analogue compound 12. Acid-mediated hydrolysis of the methyl glycoside in compound 12 using aqueous p-toluenesulfonic acid (TsOH), followed by acetylation and glycosyl chloride generation using acetyl chloride provides compound 13.

Treatment of compound 13 with the sodium salt of numerous substituted coumarin derivatives provides the key intermediates to the desired targets (compounds 44). Generation of the sodium salt is accomplished with sodium hydride in tetrahydrofuran. This method of O-glycosylation has already been applied in the stereoselective preparation of numerous O-glycosides of N-acetyl-D-neuraminic acid (Myers, et al., 1980; Eschenfelder and Brossmer, Carbohydr. Res., 1987; Eschenfelder and Brossmer, Glycoconjugate J., 1987; Okamoto and Goto, 1990; Warner and O'Brien, 1979) derived from aromatic hydroxyls. However, none of the products described herein are contained in the aforementioned references. Subsequent de-O-acetylation and de-esterification of compounds 44 is accomplished with an aqueous sodium hydroxide solution and workup involving acidification of the reaction medium. Finally, hydrogenation of the azido moiety in the presence of palladium-on-carbon catalyst, in the usual manner, gives the 7,9-di-amino compounds 45. This provides access to the 4-O-alkyl 7,9-di-substituted analogues from General Structure IIIa and IIIb.

Figure 11:
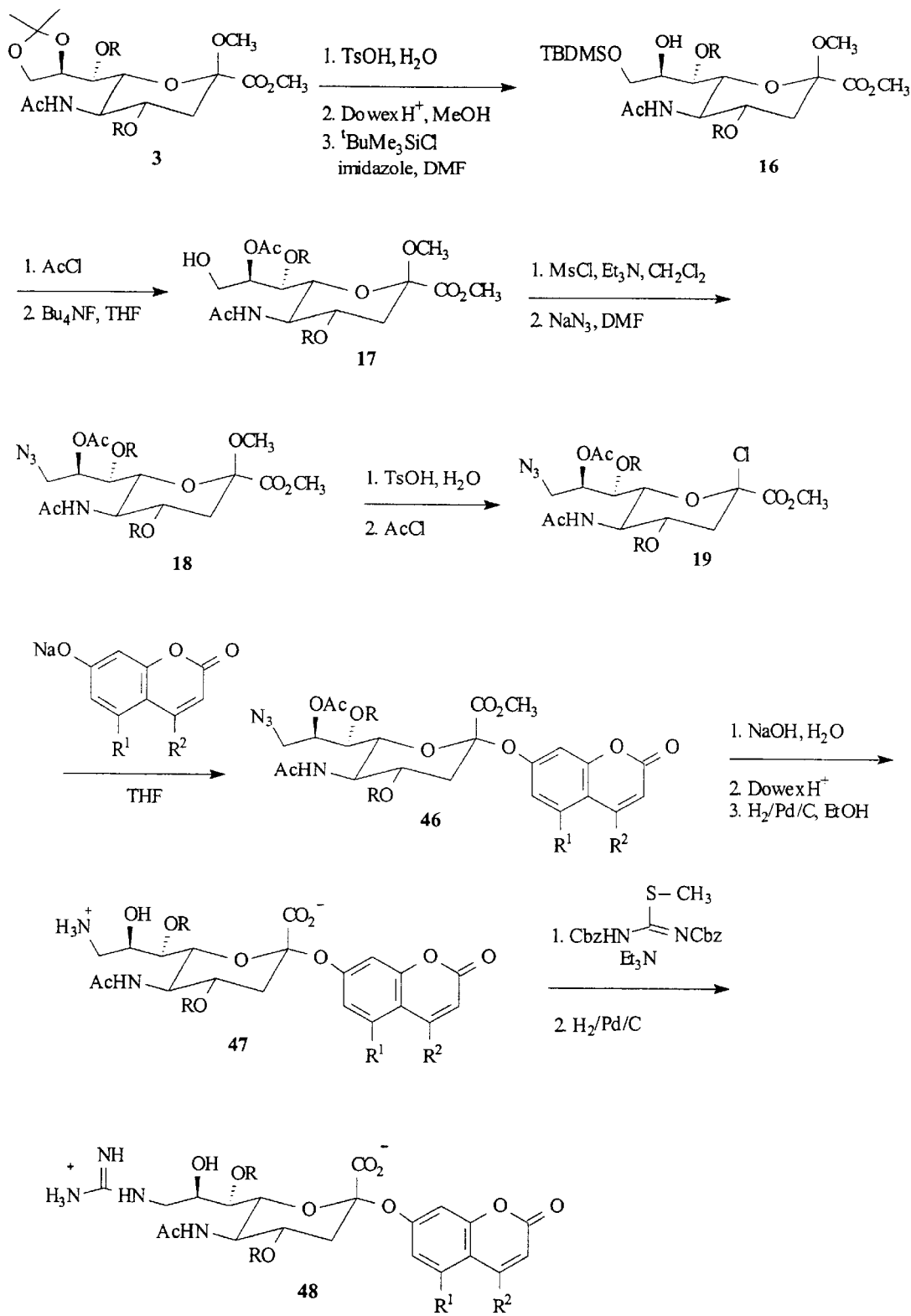
FIG. 11—synthetic approaches for selected 4,7-di-O-alkyl 9-substituted examples from General Structures IIIa and IIIb are summarized in this reaction scheme.

4,7-di-O-Alkyl 9-Substituted Analogues From General Structures IIIa and IIIb FIG. 11 illustrates constructing a basic skeleton of General Structures IIIa and IIIb via the conversion of compound 3 to compound 16 via acid-mediated methyl glycoside formation, followed by re-generation of the methyl glycoside moiety using acid-mediated means in methanol and 9-O-silylation using tert-butyldimethylsilyl chloride ($^tBuMe_2SiCl$). Compound 3 is prepared according to the procedure outlined in FIG. 1. Subsequent acetylation of the 8-hydroxyl group in 16 with acetyl chloride, followed by de-silylation with tetra-butylammonium fluoride ($Bu_4NF$) gives compound 17. Compound 17, with a free 9-hydroxyl group, is then activated for displacement via the methanesulfonate intermediate by reaction of 17 with methanesulfonyl chloride (MsCl) in the presence of base. Nucleophilic displacement of the methanesulfonate group with sodium azide readily provides the 9-azido analogue compound 18. Acid-mediated hydrolysis of the methyl glycoside in compound 18 using aqueous p-toluenesulfonic acid (TsOH), followed by acetylation and glycosyl chloride generation using acetyl chloride provides compound 19.

Treatment of compound 19 with the sodium salt of numerous substituted coumarin derivatives provides the key intermediates to the desired targets (compounds 46). Generation of the sodium salt is accomplished with sodium hydride in tetrahydrofuran. This method of O-glycosylation has already been applied in the stereoselective preparation of numerous O-glycosides of N-acetyl-D-neuraminic acid (Myers, et al., 1980; Eschenfelder and Brossmer, *Carbohydr. Res.*, 1987; Eschenfelder and Brossmer, *Glycoconjugate J.*, 1987; Okamoto and Goto, 1990; Warner and O'Brien, 1979) derived from aromatic hydroxyls. However, none of the products described herein are contained in the aforementioned references. Subsequent de-O-acetylation and de-esterification of compounds 46 is accomplished with an aqueous sodium hydroxide solution and workup involving acidification of the reaction medium. Finally, hydrogenation of the azido moiety in the presence of palladium-on-carbon catalyst, in the usual manner, gives the 9-amino compounds 47. Treatment of 47 with N,N'-bis-tert-benzyloxycarbonyl-2-methyl-2-thiopsetidourea in dichloromethane under standard conditions, followed by subsequent hydrogenation using palladium-on-carbon catalyst gives the 9-guanidino compounds 48. This provides access to the 4,7-di-O-alkyl 9-substituted analogues from General Structure IIIa and IIIb.

4-Substituted Analogues From General Structures IIIa and IIIb

Figure 12:
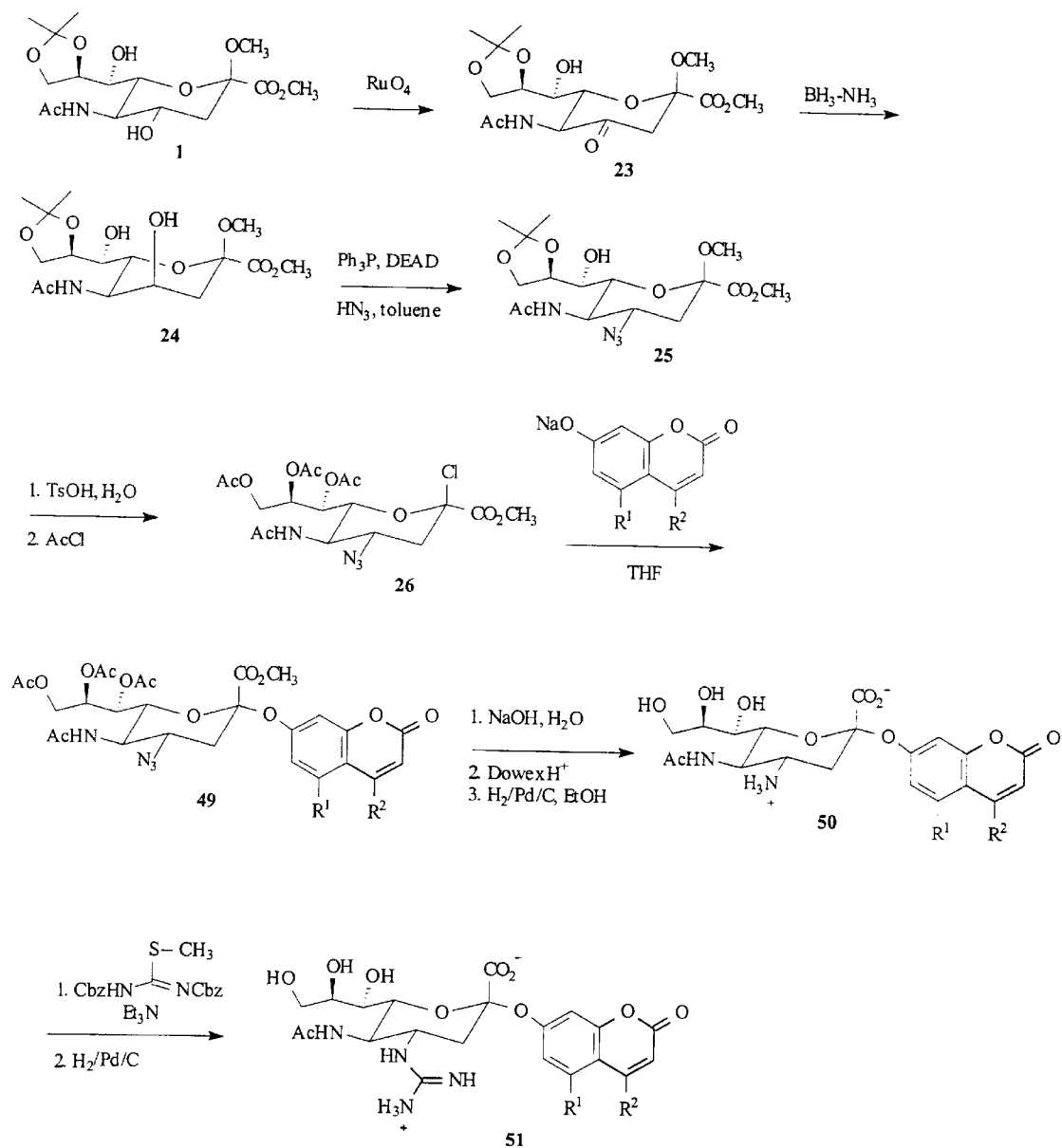
FIG. 12—synthetic approaches for selected 4-substituted examples from General Structures IIIa and IIIb are summarized in this reaction scheme.

FIG. 12 illustrates constructing a basic skeleton of General Structures IIIa and IIIb via the regioselective oxidation of the 4-hydroxyl group in compound 1 using ruthenium tetroxide under conditions reported previously (Zbiral, et al., 1989) for the same compound. Compound 1 is generally prepared according to known procedures (Kim, 1988; Liav, 1996; Hartman and Zbiral, 1989). Diastereoselective reduction of the 4-ketone group in compound 23 with borane-ammonia gives the 4-epi-sialic acid analogue 24. Compound 24, with free 4- and 7-hydroxyl groups, is then regioselectively activated for displacement at C-4 via treatment with triphenylphosphine ($Ph_3P$) and diethylazodicarboxylate (DEAD) in toluene, followed by the subsequent treatment with $HN_3$ in toluene to give the 4-azido compound 25. This two-step transformation of compound 24 to compound 25 has been reported for the preparation of the same compound (Zbiral, et al., 1989). Acid-mediated hydrolysis of the methyl glycoside and acetal moieties in compound 25 using aqueous p-toluenesulfonic acid (TsOH), followed by per-O-acetylation and glycosyl chloride generation using acetyl chloride gives compound 26.

Treatment of compound 26 with the sodium salt of numerous substituted coumarin derivatives provides the key intermediates to the desired targets (compounds 49). Generation of the sodium salt is accomplished with sodium hydride in tetrahydrofuran. This method of O-glycosylation has already been applied in the stereoselective preparation of numerous O-glycosides of N-acetyl-D-neuraminic acid (Myers, et al., 1980; Eschenfelder and Brossmer, *Carbohydr. Res.*, 1987; Eschenfelder and Brossmer, *Glycoconjugate J.*, 1987; Okamoto and Goto, 1990; Warner and O'Brien, 1979) derived from aromatic hydroxyls. However, none of the products described herein are contained in the aforementioned references. Subsequent de-O-acetylation and de-esterification of compounds 49 is accomplished with an aqueous sodium hydroxide solution and workup involving acidification of the reaction medium. Finally, hydrogenation of the azido moiety in the presence of palladium-on-carbon catalyst, in the usual manner, gives the 4-amino compounds 50. Treatment of 50 with N,N'-bis-tert-benzyloxycarbonyl-2-methyl-2-thiopseudourea in dichloromethane under standard conditions, followed by subsequent hydrogenation using palladium-on-carbon catalyst gives the 4-guanidino compounds 51. This provides access to the 4-O-substituted analogues from General Structure IIIa and IIIb.

D. Compounds with General Structures IVa and IVb and their salts and derivatives, may be prepared using any of several methods known in the art for the synthesis of substituted sialic acid analogs containing analogous structures.

To illustrate, synthetic approaches for selected examples of 4-, 4,7-, and 4,7,9-position modified analogues of General Structures IVa and IVb are summarized in FIGS. 13–16. These synthetic approaches are representative of the types of procedures that can be employed.

It should be noted that the present invention relates to chromogenic substrate compounds that are useful in the detection of sialidase. As such, the present invention relates to chromogenic substrate compounds in addition to those presented in FIGS. 13–16. Likewise, numerous other analogues with varying $R^1$, $R^2$, $R^3$, $R^6$, $R^7$, and/or $R^8$, as defined in the Summary of the Invention, can be prepared using analogous or altogether different methods.

4-O-Alkyl 7-Substituted Analogues From General Structures IVa and IVb

Figure 13:
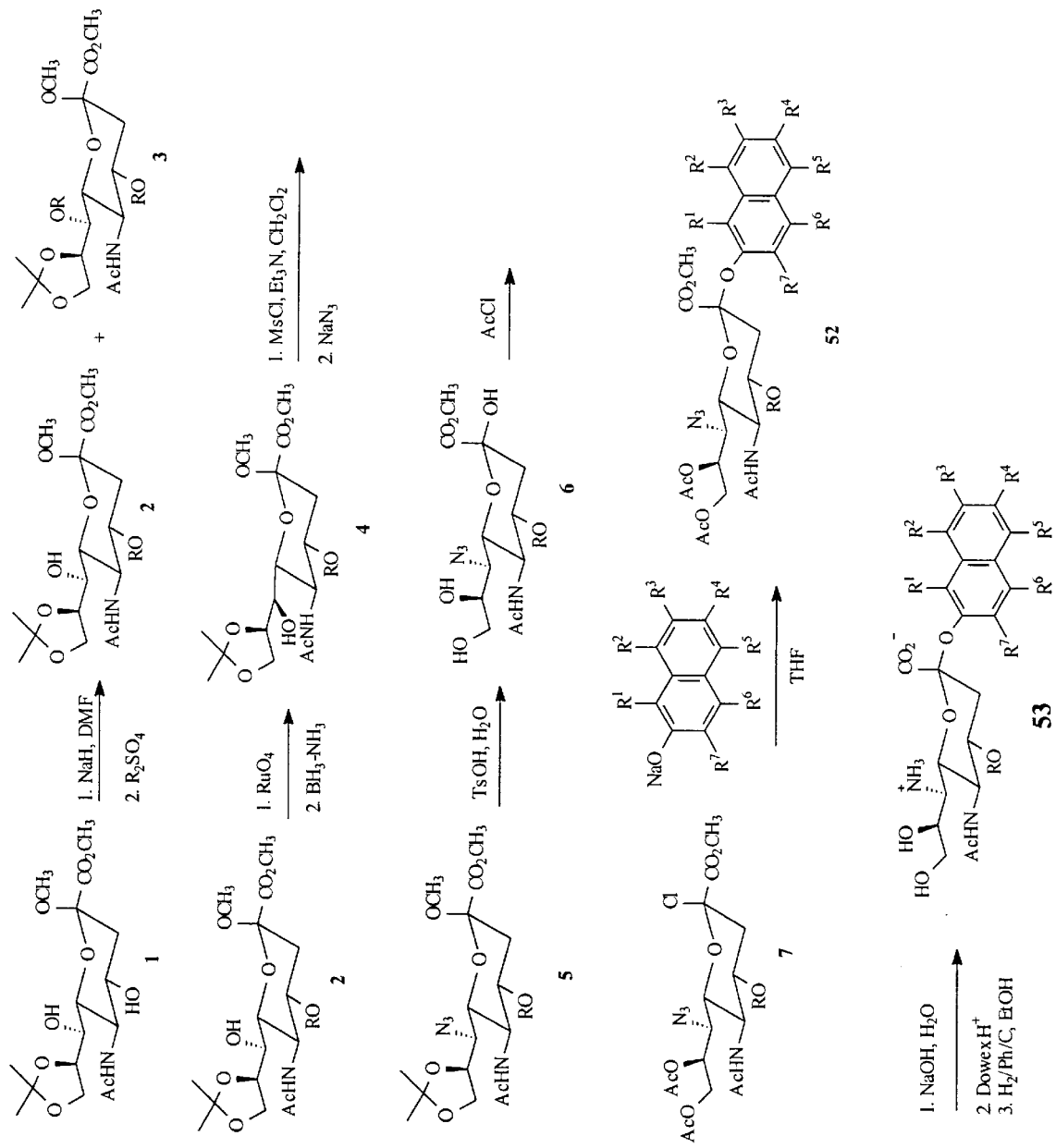
FIG. 13—synthetic approaches for selected 4-O-alkyl 7-substituted examples from General Structures IVa and IVb are summarized in this reaction scheme.

FIG. 13 illustrates constructing a basic skeleton of General Structures IVa and IVb via O-alkylation of methyl 8,9-O-isopropylidene-2-O-methyl-Neu5Ac (1) using conditions previously reported (Liav, 1998) for the same compound. Compound 1 is generally prepared according to known procedures (Kim, 1988; Liav, 1996; Hartman and Zbiral, 1989). O-Alkylation of 1 using any of a series of dialkyl sulfate analogues including dimethyl sulfate, diethyl sulfate, diisopropyl sulfate, among others, would provides the 4-O-alkyl compound 2 and the 4,7-di-O-alkyl compound 3 as a separable mixture on chromatography. Treatment of compound 2 with ruthenium tetroxide would provides the intermediate 7-keto analogue, followed by subsequent diastereoselective reduction with borane-ammonia gives the 7-epi-sialic acid analogue 4. Compound 4, with a free 7-hydroxyl group, is then activated for displacement via the methanesulfonate intermediate by reaction of 4 with methanesulfonyl chloride (MsCl) in the presence of organic base. Nucleophilic displacement of the methanesulfonate group with sodium azide readily provides the 7-azido analogue compound 5. Acid-mediated hydrolysis of the methyl glycoside and acetal moieties in compound 5 using aqueous p-toluenesulfonic acid (TsOH) will provide compound 6. Treatment of compound 6 with acetyl chloride provides the per-O-acetylated glycosyl chloride product compound 7.

Treatment of compound 7 with the sodium salt of numerous substituted naphthol derivatives provides the key intermediates to the desired targets (compounds 52). Generation of the sodium salt is accomplished with sodium hydride in tetrahydrofuran. This method of O-glycosylation has already been applied in the stereoselective preparation of numerous O-glycosides of N-acetyl-D-neuraminic acid (Myers, et al., 1980; Eschenfelder and Brossmer, *Carbohydr. Res.*, 1987; Eschenfelder and Brossmer, *Glycoconjugate J.*, 1987; Okamoto and Goto, 1990; Warner and O'Brien, 1979) derived from aromatic hydroxyls. However, none of the products described herein are contained in the aforementioned references. Subsequent de-O-acetylation and de-esterification of compounds 52 is accomplished with an aqueous sodium hydroxide solution and workup involving acidification of the reaction medium. Finally, hydrogenation of the azido moiety in the presence of palladium-on-carbon catalyst, in the usual manner, gives the 7-amino compounds 53. This provides access to the 4-O-alkyl 7-substituted analogues from General Structure IVa and IVb.

4-O-Alkyl 7,9-di-Substituted Analogues From General Structures IVa and IVb

Figure 14:
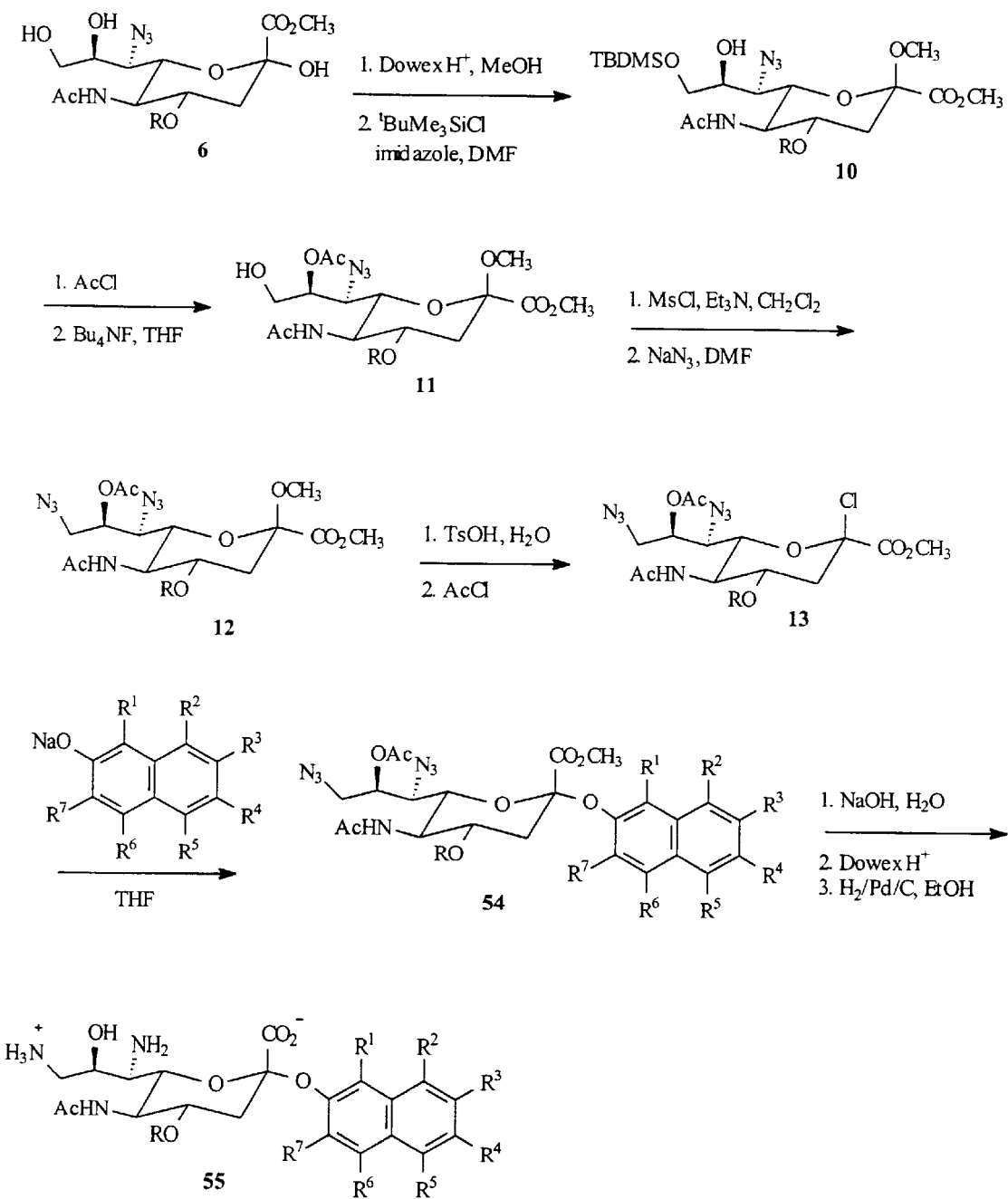
FIG. 14—synthetic approaches for selected 4-O-alkyl 7,9-disubstituted examples from General Structures IVa and IVb are summarized in this reaction scheme.

FIG. 14 illustrates constructing a basic skeleton of General Structures IVa and IVb via the conversion of compound 6 to compound 10 via acid-mediated methyl glycoside formation, followed by 9-O-silylation using tert-butyldimethylsilyl chloride ($^t$BuMe$_2$SiCl). Compound 6 is prepared according to the procedure outlined in FIG. 1. Acetylation of the 8-hydroxyl group with acetyl chloride under standard conditions, followed by de-silylation with tetra-butyl ammonium fluoride (Bu$_4$NF) readily provides the 9-hydroxy analogue 11. Compound 11, with a free 9-hydroxyl group, is then activated for displacement via the methanesulfonate intermediate by reaction of 11 with methanesulfonyl chloride (MsCl) in the presence of base. Nucleophilic displacement of the methanesulfonate group with sodium azide readily provides the 9-azido analogue compound 12. Acid-mediated hydrolysis of the methyl glycoside in compound 12 using aqueous p-toluenesulfonic acid (TsOH), followed by acetylation and glycosyl chloride generation using acetyl chloride provides compound 13.

Treatment of compound 13 with the sodium salt of numerous substituted naphthol derivatives provides the key intermediates to the desired targets (compounds 54). Generation of the sodium salt is accomplished with sodium hydride in tetrahydrofuran. This method of O-glycosylation has already been applied in the stereoselective preparation of numerous O-glycosides of N-acetyl-D-neuraminic acid (Myers, et al., 1980; Eschenfelder and Brossmer, *Carbohydr. Res.*, 1987; Eschenfelder and Brossmer, *Glycoconjugate J.*, 1987; Okamoto and Goto, 1990; Warner and O'Brien, 1979) derived from aromatic hydroxyls. However, none of the products described herein are contained in the aforementioned references. Subsequent de-O-acetylation and de-esterification of compounds 54 is accomplished with an aqueous sodium hydroxide solution and workup involving acidification of the reaction medium. Finally, hydrogenation of the azido moiety in the presence of palladium-on-carbon catalyst, in the usual manner, gives the 7-amino compounds 55. This provides access to the 4-O-alkyl 7,9-di-substituted analogues from General Structure IVa and IVb.

4,7-di-O-Alkyl 9-Substituted Analogues From General Structures IVa and IVb

Figure 15:
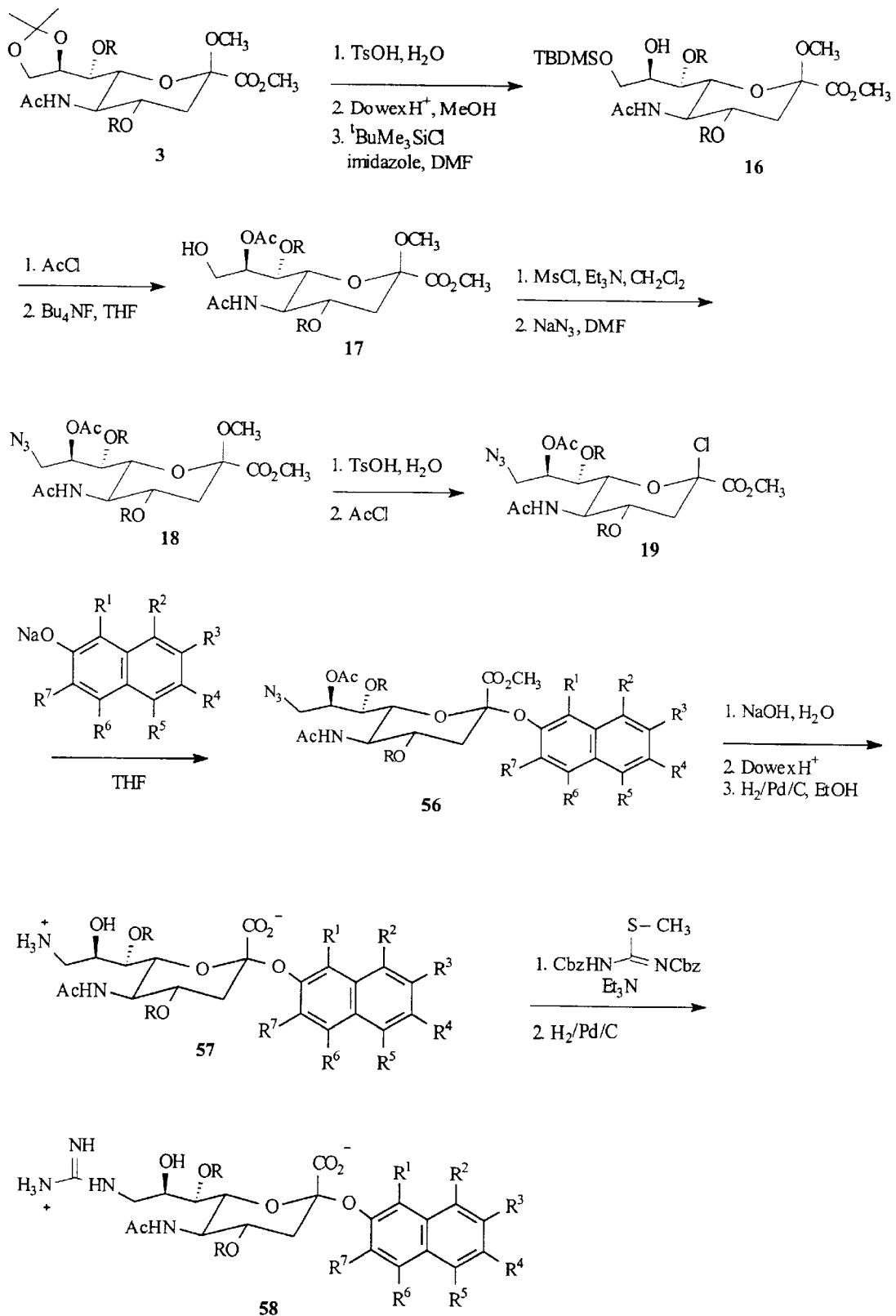
FIG. 15—synthetic approaches for selected 4,7-di-O-alkyl 9-substituted; examples from General Structures IVa and IVb are summarized in this reaction scheme.

FIG. 15 illustrates constructing a basic skeleton of General Structures IVa and IVb via the conversion of compound 3 to compound 16 via acid-mediated methyl glycoside formation, followed by re-generation of the methyl glycoside moiety using acid-mediated means in methanol and 9-O-silylation using tert-butyldimethylsilyl chloride ($^t$BuMe$_2$SiCl). Compound 3 is prepared according to the procedure outlined in FIG. 1. Subsequent acetylation of the 8-hydroxyl group in 16 with acetyl chloride, followed by de-silylation with tetra-butylammonium fluoride (Bu$_4$NF) gives compound 17. Compound 17, with a free 9-hydroxyl group, is then activated for displacement via the methanesulfonate intermediate by reaction of 17 with methanesulfonyl chloride (MsCl) in the presence of base. Nucleophilic displacement of the methanesulfonate group with sodium azide readily provides the 9-azido analogue compound 18. Acid-mediated hydrolysis of the methyl glycoside in compound 18 using aqueous p-toluenesulfonic acid (TsOH), followed by acetylation and glycosyl chloride generation using acetyl chloride provides compound 19.

Treatment of compound 19 with the sodium salt of numerous substituted naphthol derivatives provides the key intermediates to the desired targets (compounds 56). Generation of the sodium salt is accomplished with sodium hydride in tetrahydrofuran. This method of O-glycosylation has already been applied in the stereoselective preparation of numerous O-glycosides of N-acetyl-D-neuraminic acid (Myers, et al., 1980; Eschenfelder and Brossmer, *Carbohydr. Res.*, 1987; Eschenfelder and Brossmer, *Glycoconjugate J.*, 1987; Okamoto and Goto, 1990; Warner and O'Brien, 1979) derived from aromatic hydroxyls. However, none of the products described herein are contained in the aforementioned references. Subsequent de-O-acetylation and de-esterification of compounds 56 is accomplished with an aqueous sodium hydroxide solution and workup involving acidification of the reaction medium. Finally, hydrogenation of the azido moiety in the presence of palladium-on-carbon catalyst, in the usual manner, gives the 7-amino compounds 57. Treatment of 57 with N,N'-bis-tert-benzyloxycarbonyl-2-methyl-2-thiopseudourea in dichloromethane under standard conditions, followed by subsequent hydrogenation using palladium-on-carbon catalyst gives the 9-guanidino compounds 58. This provides access to the 4-O-alkyl 7-substituted analogues from General Structure IVa and IVb.

4-Substituted Analogues From General Structures IVa and IVb

Figure 16:
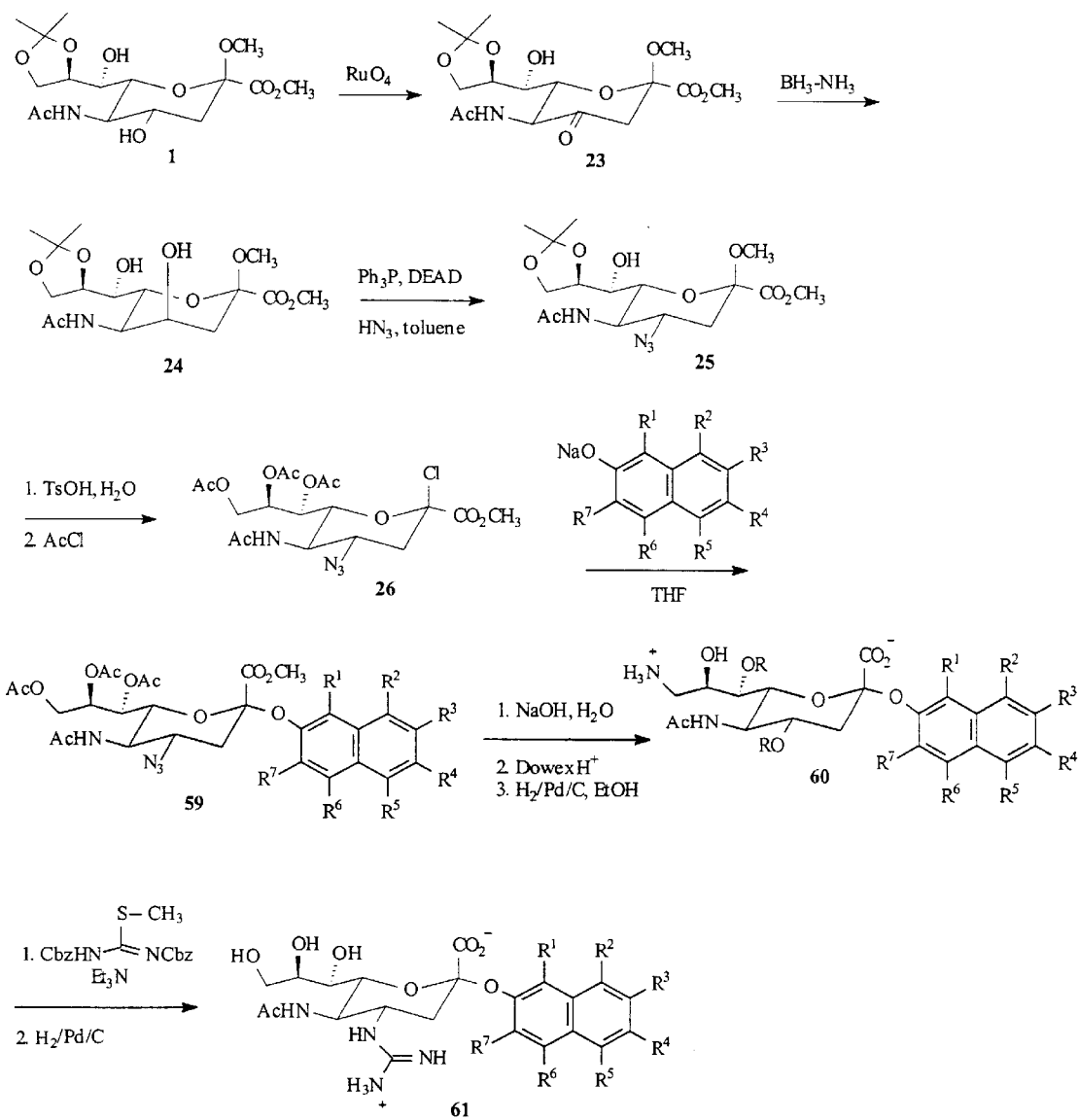
FIG. 16—synthetic approaches for selected 4-substituted examples from General Structures IVa and IVb are summarized in this reaction scheme.

FIG. 16 illustrates constructing a basic skeleton of General Structures IVa and IVb via the regioselective oxidation of the 4-hydroxyl group in compound 1 using ruthenium tetroxide under conditions reported previously (Zbiral, et al., 1989) for the same compound. Compound 1 is generally prepared according to known procedures (Kim, 1988; Liav, 1996; Hartman and. Zbiral, 1989). Diastereoselective reduction of the 4-ketone group in compound 23 with borane-ammonia gives the 4-epi-sialic acid analogue 24. Compound 24, with free 4-and 7-hydroxyl groups, is then regioselectively activated for displacement at C-4 via treatment with triphenylphosphine (Ph$_3$P) and diethylazodicarboxylate (DEAD) in toluene, followed by the subsequent treatment with HN$_3$ in toluene to give the 4-azido compound 25. This two-step transformation of compound 24 to compound 25 has been reported for the preparation of the same compound (Zbiral, et al., 1989). Acid-mediated hydrolysis of the methyl glycoside and acetal moieties in compound 25 using aqueous p-toluenesulfonic acid (TsOH), followed by per-O-acetylation and glycosyl chloride generation using acetyl chloride gives compound 26.

Treatment of compound 26 with the sodium salt of numerous substituted naphthol derivatives provides the key intermediates to the desired targets (compounds 59). Generation of the sodium salt is accomplished with sodium hydride in tetrahydrofuran. This method of O-glycosylation has already been applied in the stereoselective preparation of numerous O-glycosides of N-acetyl-D-neuraminic acid (Myers, et al., 1980; Eschenfelder and Brossmer, *Carbohydr. Res.*, 1987; Eschenfelder and Brossmer, *Glycoconjugate J.*, 1987; Okamoto and Goto, 1990; Warner and O'Brien, 1979) derived from aromatic hydroxyls. However, none of the products described herein are contained in the aforementioned references. Subsequent de-O-acetylation and de-esterification of compounds 59 is accomplished with an aqueous sodium hydroxide solution and workup involving acidification of the reaction medium. Finally, hydrogenation of the azido moiety in the presence of palladium-on-carbon catalyst, in the usual manner, gives the 4-amino compounds 60. Treatment of 60 with N,N'-bis-tert-benzyloxycarbonyl-2-methyl-2-thiopseudourea in dichloromethane under standard conditions, followed by subsequent hydrogenation using palladium-on-carbon catalyst gives the 4-guanidino compounds 61. This provides access to the 4-O-substituted analogues from General Structure IVa and IVb.

E. Biochemical Evaluation of a Chromogenic Substrate Product with Bacterial Sialidase and with Viral Sialidase. The source of bacterial sialidase was from purified recombinant bacterial sialidase from Salmonella T. The source of viral sialidase was from whole influenza virus A1PR/8/34. The bacterial sialidase preparation (40 μL of a solution containing 10 μg/mL in distilled water) or the viral sialidase preparation (40 μL of a solution containing 107 PFU/mL) was added to 60 μL of a buffer solution containing the substrate compound (compound 9c, wherein $R^6=R^7=R^8=R^9=H$; Table 2) at ca. 0.7 mM concentration in potassium acetate (0.5 M; pH 6.0). The reaction proceeded at 37° C. for 30 minutes, at which time the pH was adjusted by the addition of 20 μL of a solution of sodium hydroxide (1.0 M, pH>11.0). A color change to blue was readily visible. The reaction progress was quantitated by measuring the light absorption of the reaction mixture. The light absorption was measured with a spectrophotometer at 517 nm with a 1 cm path cell. In the experiment conducted with bacterial sialidase, the absorbance was measured as 2.448. In the experiment conducted with viral sialidase, the absorbance was measured as 1.168. It should be noted that the reaction using sialidase derived from influenza virus was not allowed to proceed to completion.

F. Classes of Chromogenic Substrate Compounds of Sialidases. As used herein, the "effective amount" of a compound of the invention required for the use in the method presented herein will differ not only with the particular compound to be selected but also with the mode of application, and the nature of the sample specimen. The exact amount will be evaluated by testing with a sufficient number of clinical samples in each application as conducted by persons skilled in the art. However, a generally suitable concentration will range from about 0.1 to about 10 mM/mL of testing solutions. Furthermore, the compounds may be used as pure chemical applied to a test solution, or a pure chemically acceptable salt or derivative. However, it is preferable to provide the active chemical or its chemically acceptable salt or derivative, as a medicinal formulation, either as a dry material (reaction solution provided separately), or as a solution or suspension (an aqueous solution or other chemically acceptable solvent solutions), or as a dip stick. The subject specimen can be applied to the test for measuring the activity levels of sialidases. Those skilled in the art having the benefit of the instant disclosure will appreciate that amounts and modes of application are readily determinable without undue experimentation.

References

Aamlid, K. H., G. Lee, B. V. Smith, A. C. Richardson, R. G. Price (1990) "New colorimetric substrates for the assay of glycosidases," *Carbohydr. Res.* 205:c5–c9.

Ambrose, M. G., R. W. Binkley (1983) "Synthesis of Deoxyhalogeno Sugars. Reactions of Halide Ions with 1,2,3,4-Tetra-O-acetyl-6-O-[(trifluoromethyl)sulfonyl]-(-D-glucopyranose," *J. Org. Chem.* 48:674–677.

Baggett, N., B. J. Marsden (1982) "Reinvestigation of the Synthesis of 4-Methylcoumarin-7-yl 5-Acetamido-3,5-dideoxy-(-D-glycero-D-galacto-2-nonulopyranosidonic Acid, A Fluorimetric Substrate for Neuram inidase," *Carbohydr. Res.* 110:11–18.

Barakat, M. Z., M. F. Abdel-Wahab, M. M. El-Sadr (1956) "Oxidation of organic compounds by solid manganese dioxide," *J. Chem. Soc.* 4685–4687.

Barker, S. A., J. S. Brimacombe, M. R. Harnden, J. A. Jarvis (1963) "Sucrose derivatives. Part II. Some silyl and cyanoethyl ethers and a hepta-acetal," *J. Chem. Soc.* 3403–3406.

Bonten, E., et al. (1996) "Characterization of human lysosomal neuraminidase defines the molecular basis of the metabolic storage disorder sialidosis," *Genes & Devel.* 10:3156–3169.

Briselden, A. M., et al. (1992) "Sialidases (Neuraminidases) in bacterial vaginosis and bacterial vaginosis-associated microflora," *J. Clin. Microbiol.* 30:663–666.

Brown, H. C., W. S. Park, B. T. Cho, P. V. Ramachandran (1987) "Selective Reductions. 40. A critical examination of the relative effectiveness of various reducing agents for the asymmetric reduction of different classes of ketones," *J. Org. Chem.* 52:5406–5412.

Cacalano, G. et al. (1992) "Production of the *Pseudomonas aeruginosa* neuraminidase is increased under hyperosmolar conditions and is regulated by genes involved in alginate expression," *J. Clin. Invest.* 89:1866–1874.

Chong, A. K. J., M. S. Pegg, M. von Itzstein (1991) "Characterization of an Ionisable Group Involved in Binding and Catalysis by Sialidase from Influenza Virus," *Biochem. Int.* 24:165–171.

Clarke, M. F., L. N. Owen (1949) "Alicyclic Glycols. Part I. Toluene-p-sulphonyl and methanesulphonyl derivatives of cycloHexane-1:2-diol," *J. Chem. Soc.* 315–320.

Colman, P. M., J. N. Varghese, W. G. Laver (1983) "Structure of the Catalytic and Antigenic Sites in Influenza Virus Neuraminidase," *Nature* 303:41–44.

Colman, P. M. (1989) "Neuraminidase: Enzyme and Antigen." In The Influenza Virus; Krug, R. M. Ed.; Plenum: New York, pp 175–218.

Corey, E. J., B. B. Snider (1972) "A total synthesis of ( )-Fumagillin," *J. Am. Chem. Soc.* 94:2549–2550.

Crennell, S., et al. (1994) "Crystal Structure of Vibrio cholerea neuraminidase reveals dual lectin-like domains in addition to the catalytic domain," *Structure* 2:535–544.

Cross G. A., and G. B. Takle (1993) "The surface transsialidase family of *Trypanosoma cruzi*," *Annu. Rev. Microbiol.* 47:385–411.

Czernecki, S., C. Georgoulis, C. L. Stevens, K. Vijayakumaran (1985) "Pyridinium dichromate oxidation, modifications enhancing its synthetic utility," *Tetrahedron Lett.* 26:1699–1702.

Drzeniek, R. (1972) "Viral and Bacterial Neuraminidases," *Curr. Top. Microbiol. Immunol.* 59:35–74.

Eschenfelder, V., R. Brossmer (1987) "Synthesis of p-Nitrophenyl 5-Acetamido-3,5-dideoxy-(-D-glycero-D- galacto-2-nonulopyranosidonic Acid, A Chromogenic Substrate for Sialidases," *Carbohydr. Res.* 162:294–297.

Eschenfelder, V., R. Brossmer (1987) "5-Bromo-indol-3-yl 5-acetamido-3,5-dideoxy-(-D-glycero-d-galactononulopyranosidonic Acid, a Novel Chromogenic Substrate for the Staining of Sialidase Activity," *Glycoconjugate J.* 4171–4178.

Feichtinger, K., C. Zapf, H. L. Sings, M. Goodman (1998) "Diprotected Triflylguanidines: A New Class of Guanidinylation Reagents," *J. Org. Chem.* 63:3804–3805.

Freundenberg, K., H. Resnik, H. Boesenberg, D. Rasenack (1952) "Das an der Verholtzung Beteiligte Fermentsystem," *Chem. Ber.* 85:641–647.

Gornati, R., et al. (1997) "Activities of glycolipid glycosyltransferases and silaidases during the early development of *Xenpus laevis*," *Mol. Cell Biochem.* 166:117–124.

Hanessian, S, P. Lavalle (1975) "The preparation and synthetic utility of tert-butyldiphenylsilyl ethers," *Can. J. Chem.* 53:2975–2977.

Hartmann, M., E. Zbiral (1989) *Monatsh. Chem.* 120:899.

Hartmann, M., R. Christian, E. Zbiral (1990) "Synthesis of (-Methyl Ketosides of 4-oxo-, and 8-oxo-N-Acetylneurminic Acid and the Corresponding 7,7-and 8,8-Dimethoxy Derivatives: Their Behavior Towards CMP-Sialate Synthase," *Liebigs Ann. Chem.* 89–91.

Hirst, G. K. (1941) "The Agglutination of Red Blood Cells by Allontoic Fluid of Chick Embryos Infected with Influenza Virus," *Science* 94:22–23.

HoJo, K., H. Yoshno, T. Mukaiyama (1977) *Chem. Lett.* 133–136.

Holmquist, L., R. Brossmer (1972) "Specificity of nieuraminidase, synthesis and properties of the 2-aminoethyl (- and the 2-pyridyl (- and (-glycosides of N-acetyl-D-neuraminic acid," *Hoppe-Seyler's Z. Physiol. Chem.* 353:1346–1350.

Horwitz, J. P., J. Chua, R. J. Curby, A. J. Tomson, M. A. Darooge, B. E. Fisher, J. Mauricio, I. Klundt (1964) "Substrates for Cytochemical Demonstration of Enzyme Activity. I. Some Substituted 3-Indolyl-(-D-glycopyranosides," *J. Med. Chem.* 7:574–575.

Iwanowicz, E. J., M. A. Poss, J. Lin (1993) "Preparation of N,N'-Bis-tert-Butoxycarbonylthiourea," *Synthetic Commun.* 23:1443–1445.

Johnson, S. C., J. Dahl, T. Shih, D. J. A. Schedler, L. Anderson, T. L. Benjamin, D. C. Baker (1993) "Synthesis and Evaluation of 3-Modified 1D-myo-Inositols as Inhibitors and Substrates of Phosphatidylinositol Synthase and Inhibitors of myo-Inositol Uptake by Cells," *J. Med. Chem.* 36:3628–3635.

Kang, S. H., C. Y. Hong (1987) "Simple synthetic routes to Geiparvarin," *Tetrahedron Lett.* 28:675–678.

Kim, et al. (1988) "Enzymes in Carbohydrate Synthesis: N-Acetylneuraminic Acid Aldolase Catalyzed Reactions and Preparation of N-Acetyl-2-deoxy-D-neuraminic Acid Derivatives," *J. Am. Chem. Soc.* 110:6481–6486.

Klenk, H. D.; R. Rott (1988) "Molecular Biology of Influenza Virus Pathogenicity," *Adv. Virus Res.* 34:247–280.

Kuhn, R., P. Lutz, D. L. MacDonald (1966) "Synthese anomerer Sialinsaure-methylketoside," *Chem. Ber.* 99:611–617.

Liav, A., J. A. Hausjergen, C. D. Shimasaki (1998) "4,7-Dialkoxy N-Acetylneuraminic Acid Derivatives and Methods for Detection of Influenza Type A and B Viruses in Clinical Specimens," U.S. Pat. No. 5,719,020.

Ley, A. N., R. J. Bowers, S. Wolfe (1987) "Indoxyl-(-D-glucuronide, a Novel Chromogenic Reagent for the Specific Detection arid Enumeration of *Escherichia coli* in Environmental Samples," *Can. J. Microbiol.* 34:690–693.

Liljemark, W. F., et al. (1989) "Effects of neuraminidase on the adherence to salivary pellicle of *Streptococcus sangius* and *Streptococcus mitis*," *Caries. Res.* 23:141–145.

Lodge, E. P., C. H. Heathcock (1987) "Steric effects, as well as σ-orbital energies, are important in diastereoface differentiation in additions to chiral aidehydes," *J. Am. Chem. Soc.* 109:3353–3361.

Meyer, E. (1992) "Internal Water Molecules and Hydrogen Binding in Biological Macromolecules: A Review of Structural Features with Functional Implications," *Prot. Sci.* 1:1543–1562.

Mitsunobu, O., M. Wada, T. Sano (1972) "Stereospecific and Stereoselective Reactions. I. Preparation of Amines from Alcohols," *J. Am. Chem. Soc.* 94:679–680.

Myers, R. W., R. T. Lee, Y. C. Lee, G. H. Thomas, L. W. Reynolds, Y. Uchida (1980) "The Synthesis of 4-Methylumbelliferyl α-Ketoside of N-Acetyl-Neuraminic Acid and Its Use in a Fluoromatic Assay for Neuraminidases," *Anal. Biochem.* 101:166–174.

Nystrom, J.-E., T. D. McCanna, P. Helmquist, R. S. Iyer (1985) "Short intramolecular Diels-Alder approach to functionalized spiro[4,5]decanes," *Tetrahedron Lett.* 26:5393–5396.

Okamoto, K., T. Goto (1990) "Glycosidation of Sialic Acids," *Tetrahedron* 46:5835–5837.

Palese, P., K. Jobita, M. Ueda, R. W. Compans (1974) "Characterization of Temperature Sensitive Influenza Virus Mutants Defective in Neuraminidase," *Virology* 61:397–410.

Patel, A. A. C.Richardson(1986) "3-Methoxy-4-(2-nitrovinyl)phenyl Glycosides as Potential Chromogenic Substrates for the Assay of Glycosidases," *Carbohydr. Res.* 146:241–249.

Robertson, A. (1927) "Syntheses of Glucosides. Part I. The Synthesis of Indican," *J/ Chem. Soc.* 1937–1943.

Salunkhe, M., M. Hartmann, M., W. Schmidt, E. Zbiral (1988) "A New Useful Approach to the Epimers at C-7 and C-7,8 of N-Acetylneuraminic Acid," *Liebigs Ann. Chem.* 187–189.

Schauer, R. (1985) "Sialic Acids and Their Roles as Biological Masks," *Trends Biochem. Sci.* 10:357–360.

Stork, G., P.F. Hudrlik (1968) "Isolation of ketone enolates as trialkylsilyl ethers," *J. Am. Chem. Soc.* 60:4462–4464.

Taylor, N. R., M. von Itzstein (1994) "Molecular Modeling Studies on Ligand Binding to Sialidase from Influenza Virus and the Mechanism of Catalysis," *J. Med. Chem.* 37:616–624.

Tian, Z., P. Edwards, R. W. Roeske (1992) "Synthesis of optically pure $C^α$-methyl-arginine," *Int. J. Peptide Protein Res.* 40:119–126.

Turner, G. A., J. F. Maher, C. W. Clinkscales; M. D. Roark (1997) "Methods for Diagnosing Human Influenza and 4-Position Modified Chromogenic N-Acetylneuraminic Acid Substrated for Use Therein," U.S. Pat. No. 5,663,055.

Varghese, J. N., W. G. Laver, P. M. Colman (1983) "Structure of the Influenza Virus Glycoprotein Antigen Neuraminidase at 2.9 A° Resolution," *Nature* 303:35–40 (1983).

Varghese, J. N., P. M. Colman (1991) "The Three-dimensional Structure of the Neuraminidase of Influenza Virus A/Tokyo/3/67 at 2.2 A° Resolution," *J. Mol. Biol.* 221:473–486.

Varghese, J. N., J. McKimm-Breschkin, J. B. Caldwell, A. A. Kortt, P. M. Colman (1992) "The Structure of the Complex Between Influenza Virus Neuraminidase and Sialic Acid, The Viral Receptor," *Proteins* 14:327–332.

Warner, T. G., J. S. O'Brien (1979) "Synthesis of 2'-(4-Methylumbelliferyl)-(-D-N-acetylneuraminic Acid and Detection of Skin Fibroblast Neuraminidase in Normal Humans and in Sialidosis," *Biochemistry* 18:2783–2787.

Zbiral, E., H. H. Brandstetter, E. P. Schreiner (1988) "Strukturelle Abwandlungen an N-Acetylneruaminsauren, 8[1] Synthese von 7-, 8-, 9-Desoxy- und 4,7-Didesoxy-neuraminäure," *Monatsh. Chem.* 119:127–141.

Zbiral, E., E. Schreiner, R. Christian (1989) "Synthesis of the 4-Acetamido-4-deoxy Analogue of N-Acetylneuraminic Acid and its Behavior towards CMP-Sialate Synthase," *Carbohydr. Res.* 194:c15–c18.

What is claimed is:

1. A method of measuring sialidase activity in a sample comprising the step of contacting said sample with a chromogenic sialidase substrate compound or a chromogenic sialidase substrate composition comprising a formula of General Structure I and salts of General Structure I, wherein General Structure I is defined as follows:

General Structure I

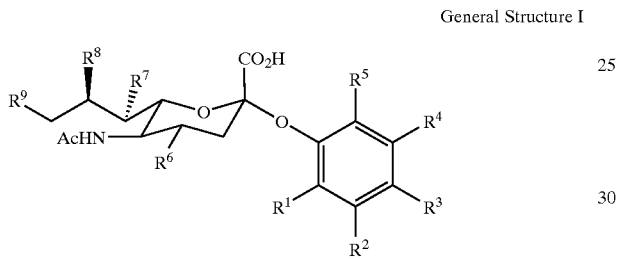

wherein, for General Structure I, $R^1$, $R^2$, $R^4$, and $R^5$ can each, independently, be selected from the group consisting of H, $R^{11}$, $OC(O)R^{11}$, $NO_2$, $NHC(O)R^{11}$, Cl, Br, I, F, CHO, $C(O)R^{11}$, $C(N\text{—}OH)NH_2$, $OPO_3R^{10}$, $OPO_2(CH_2)_jCH_3$, $CH_2PO_3R^{10}$, $OSO_3R^{10}$, $OSO_2(CH_2)_jCH_3$, $CH_2SO_3R^{10}$, and CN, where j is an integer from 0 to 3; wherein $R^3$=CHO, $(CR^{12}{=}CR^{12})_kCN$ or $(CR^{12}{=}CR^{12})_kNO_2$, where k is an integer from 1 to 3, or

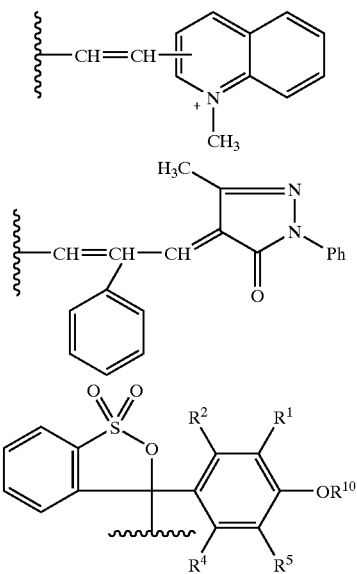

wherein, wherein, $R^6$, $R^7$, and $R^8$ can each, independently, be selected from the group consisting of H, $N_3$, $R^{11}$, $NO_2$, $NHC({=}NH)N(R^{10})_2$, $NHC(O)R^{11}$, $C(O)R^{11}$, Cl, Br, I, F, $SR^{10}$, and $(CH_2)_xC({=}NH)N(R^{10})_2$ where x is an integer from 0 to 3; wherein $R^9$ is: 1) $OR^{10}$ and $R^{10}$ is $C(CH_3)_3$, $CH(CH_3)_2$, $CH_2CH(CH_3)_2$, $CH(CH_3)(CH_2)_mCH_3$ where m is an integer from 0 to 3, or $(CH_2)_mCH_3$, where m is an integer from 0 to 3, or 2) $R^9$ is selected from the group consisting of $C(CH_3)_3$, $CH(CH_3)_2$, $CH_2CH(CH_3)_2$, $CH(CH_3)(CH_2)_mCH_3$ where m is an integer from 0 to 3, $CH_2CH_3$, $(CH_2)_2CH_3$, $(CH_2)_3CH_3$, $N(R^{10})_2$, $NO_2$, $NHC({=}NH)N(R^{10})_2$, $NHC(O)R^{11}$, $C(O)R^{11}$, Cl, Br, I, F, $SR^{10}$, and $(CH_2)_xC({=}NH)N(R^{10})_2$ where x is an integer from 0 to 3; wherein $R^{10}$=H, $C(CH_3)_3$, $CH(CH_3)_2$, $CH_2CH(CH_3)_2$, $CH(CH_3)(CH_2)_mCH_3$ where m is an integer from 0 to 3; or $(CH_2)_mCH_3$, where m is an integer from 0 to 3; wherein $R^{11}$=$R^{10}$, $OR^{10}$, or $N(R^{10})_2$; wherein, $R^{12}$=H or $(CH_2)_n$; where n is an integer from 0 to 3;

or, also for General Structure I, wherein, $R^3$ can be selected from the group consisting of H, $R^{11}$, $OC(O)R^{11}$, $NHC(O)R^{11}$, Cl, Br, I, F, CHO, $C(O)R^{11}$, $C(N\text{—}OH)NH_2$, $OPO_3R^{10}$, $OPO_2(CH_2)_jCH_3$, $CH_2PO_3R^{10}$, $OSO_3R^{10}$, $OSO_2(CH_2)_jCH_3$, $CH_2SO_3R^{10}$, or CN, where j is an integer from 0 to 3; $R^1$ and $R^5$ can each, independently, be selected from the group consisting of H, $R^{11}$, $OC(O)R^{11}$, $NO_2$, $NHC(O)R^{11}$, Cl, Br, I, F, CHO, $C(O)R^{11}$, $C(N\text{—}OH)NH_2$, $OPO_3R^{10}$, $OPO_2(CH_2)_jCH_3$, $CH_2PO_3R^{10}$, $OSO_3R^{10}$, $OSO_2(CH_2)_jCH_3$, $CH_2SO_3R^{10}$, or CN, where j is an integer from 0 to 3; wherein $R^2$ or $R^4$=H, $R^{11}$, $OC(O)R^{11}$, $NO_2$, $NHC(O)R^{11}$, Cl, Br, I, F, CHO $C(O)R^{11}$, $C(N\text{—}OH)NH_2$, $OPO_3R^{10}$, $OPO_2(CH_2)_jCH_3$, $CH_2PO_3R^{10}$, $OSO_3R^{10}$, $OSO_2(CH_2)_jCH_3$, $CH_2SO_3R^{10}$, CN, where j is an integer from 0 to 3, $(CR^{12}{=}CR^{12})_kCN$, and $(CR^{12}{=}CR^{12})NO_2$, where k is an integer from 1 to 3 or

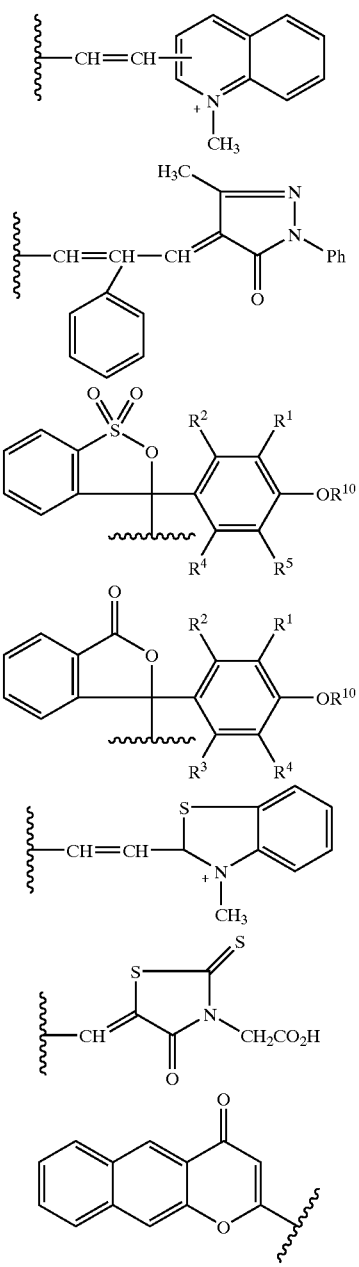

wherein, $R^6$, $R^7$, and $R^8$ can each, independently, be selected from the group consisting of H, $N_3$, $R^{11}$, $NO_2$, $NHC(=NH)N(R^{10})_2$, $NHC(O)R^{11}$, $C(O)R^{11}$, Cl, Br, I, F, $SR^{10}$, and $(CH_2)_xC(=NH)N(R^{10})_2$ where x is an integer from 0 to 3; wherein $R^9$ is: 1) $OR^{10}$ and $R^{10}$ is $C(CH_3)_3$, $CH(CH_3)_2$, $CH_2CH(CH_3)_2$, $CH(CH_3)(CH_2)_mCH_3$ where m is an integer from 0 to 3, or $(CH_2)_mCH_3$, where m is an integer from 0 to 3 or, 2) $R^9$ is selected from the group consisting of $C(CH_3)_3$, $CH(CH_3)_2$, $CH_2CH(CH_3)_2$, $CH(CH_3)(CH_2)_mCH_3$ where m is an integer from 0 to 3, $CH_2CH_3$, $(CH_2)_2CH_3$, $(CH_2)_3CH_3$, $N(R^{10})_2$, $NO_2$, $NHC(=N)N(R^{10})_2$, $NHC(O)R^{11}$, $C(O)R^{11}$, Cl, Br, I, F, $SR^{10}$, and $(CH_2)_xC(=NH)N(R^{10})_2$ where x is an integer from 0 to 3; wherein $R^{10}$=H, $C(CH_3)_3$, $CH(CH_3)_2$, $CH_2CH(CH_3)_2$, $CH(CH_3)(CH_2)_mCH_3$ where m is an integer from 0 to 3, or $(CH_2)_mCH_3$, where m is an integer from 0 to 3; wherein $R^{11}=R^{10}$, $OR^{10}$, or $N(R^{10})_2$; wherein, $R^{12}$=H or $(CH_2)_n$; where n is an integer from 0 to 3;

or, also for General Structure I, wherein, $R^1$ or $R^5$=H, $R^{11}$, $OC(O)R^{11}$, $NO_2$, $NH(C(O)R^{11}$, Cl, Br, L, F, CHO, $C(O)R^{11}$, $C(N-OH)NH_2$, $OPO_3R^{10}$, $OPO_2(CH_2)_jCH_3$, $CH_2PO_3R^{10}$, $OSO_3R^{10}$, $OSO_2(CH_2)_jCH_3$, $CH_2SO_3R^{10}$, CN, where j is an integer from 0 to 3, $(CR^{12}=CR^{12})_kCN$ and $(CR^{12}=CR^{12})_kNO_2$, where k is an integer from 1 to 3; wherein, $R^2$ and $R^4$ can each, independently be selected from the group consisting of H, $R^{11}$, $OC(O)R^{11}$, $NO_2$, $NHC(O)R^{11}$, Cl, Br, I, F, CHO, $C(O)R^{11}$, $C(N-OH)NH_2$, $OPO_3R^{10}$, $OPO^2(CH_2)_jCH_3$, $CH_2PO_3R^{10}$, $OSO_3R^{10}$, $OSO_2(CH_2)_jCH_3$, $CH_2SO_3R^{10}$, and CN, where j is an integer from 0 to 3; wherein $R^3$ can be selected from the group consisting of H, $R^{11}$, $OC(O)R^{11}$, $NHC(O)R^{11}$, Cl, Br, I, F, CHO, $C(O)R^{11}$, $C(N-OH)NH_2$, $OPO_3R^{10}$, $OPO_2(CH_2)_jCH_3$, $CH_2PO_3R^{10}$, $OSO_3R^{10}$, $OSO(CH_2)_jCH_3$, $CH_2SO_3R^{10}$, and CN, where j is an integer from 0 to 3; wherein, $R^6$, $R^7$, and $R^8$ can each, independently, be selected from the group consisting of H, $N_3$, $R^{11}$, $NO_2$, $NHC(=NH)N(R^{10})_2$, $NHC(O)R^{11}$, $C(O)R^{11}$, Cl, Br, I, F, $SR^{10}$, and $(CH_2)_xC(=NH)N(R^{10})_2$ where x is an integer from 0 to 3; wherein $R^9$ is: 1) $OR^{10}$ and $R^{10}$ is $C(CH_3)_3$, $CH(CH_3)_2$, $CH_2CH(CH_3)_2$, $CH(CH_3)(CH_2)_mCH_3$ where m is an integer from 0 to 3, or $(CH_2)_mCH_3$, where m is an integer from 0 to 3, or 2) $R^9$ is selected from the group consisting of $C(CH_3)_3$, $CH(CH_3)_2$, $CH_2CH(CH_3)_2$, $CH(CH_3)(CH_2)_mCH_3$ where m is an integer from 0 to 3, $CH_2CH_3$, $(CH_2)_2CH_3$, $(CH_2)_3CH_3$, $N(R^{10})_2$, $NO_2$, $NHC(=NH)N(R^{10})$, $NHC(O)R^{11}$, $C(O)R^{11}$, Cl, Br, I, F, $SR^{10}$, and $(CH_2)_xC(=NH)N(R^{10})_2$ where x is an integer from 0 to 3; wherein $R^{10}$=H, $C(CH_3)_3$, $CH(CH_3)_2$, $CH_2CH(CH_3)_2$, $CH(CH_3)(CH_2)_mCH_3$ where m is an integer from 0 to 3, or $(CH_2)_mCH_3$, where m is an integer from 0 to 3; wherein $R^{11}=R^{10}$, $OR^{10}$, or $N(R^{10})_2$; and wherein, $R^{12}$=H or $(CH_2)_n$; where n is an integer from 0 to 3.

2. A method for detecting or monitoring the presence of a sialidase in a human or animal, wherein said method comprises measuring sialidase activity by contacting a fluid sample from said human or animal with a chromogenic substrate compound or chromogenic sialidase substrate composition comprising a chromogenic sialidase substrate compound comprising General Structure I and salts of General Structure I, wherein General Structure I is defined as follows:

General Structure I

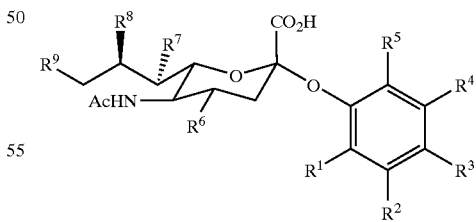

wherein, for General Structure I, $R^1$, $R^2$, $R^4$, and $R^5$ can each, independently, be selected from the group consisting of H, $R^{11}$, $OC(O)R^{11}$, $NO_2$, $NHC(O)R^{11}$, Cl, Br, I, F, CHO, $C(O)R^{11}$, $C(N-OH)NH_2$, $OPO_3R^{10}$, $OPO_2(CH_2)_jCH_3$, $CH_2PO_3R^{10}$, $OSO_3R^{10}$, $OSO_2(CH_2)_jCH_3$, $CH_2SO_3R^{10}$, and CN, where j is an integer from 0 to 3; wherein $R^3$=CHO, $(CR^{12}=CR^{12})_kCN$ or $(CR^{12}=CR^{12})_kNO_2$, where k is an integer from 1 to 3, or

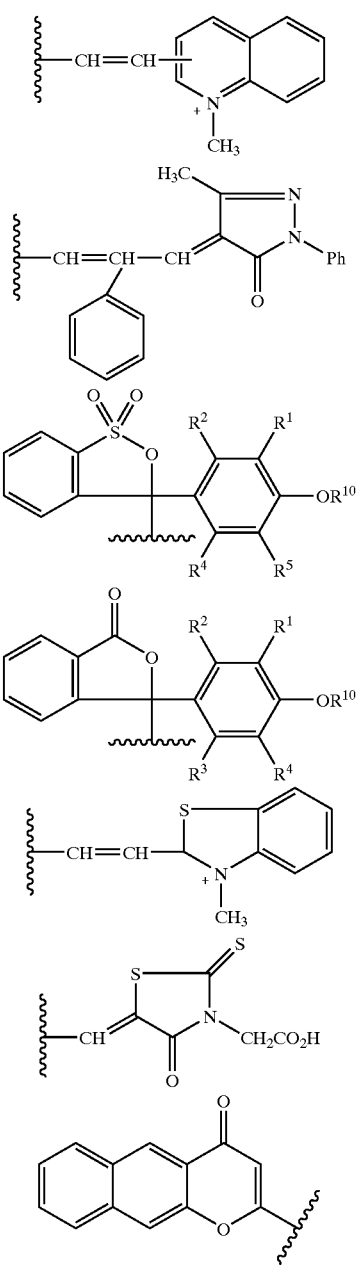

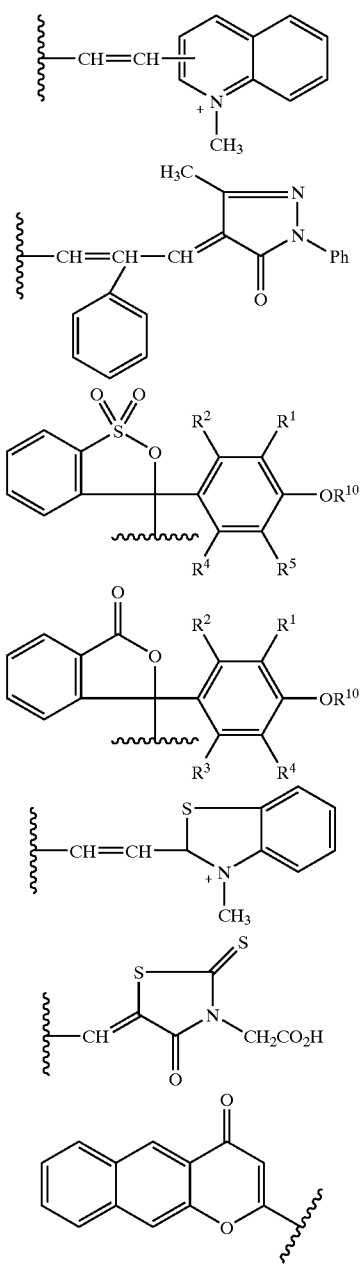

$R^{11}$, NHC(O)$R^{11}$, Cl, Br, I, F, CHO, C(O)$R^{11}$, C(N—OH)NH$_2$, OPO$_3R^{10}$, OPO$_2$(CH$_2$)$_j$CH$_3$, CH$_2$PO$_3R^{11}$, OSO$_3R^{10}$, OSO$_2$(CH$_2$)$_j$CH$_3$, CH$_2$SO$_3R^{10}$, or CN, where j is an integer from 0 to 3; $R^1$ and $R^5$ can each, independently, be selected from the group consisting of H, $R^{11}$, OC(O)$R^{11}$, NO$_2$, NHC(O)$R^{11}$, Cl, Br, I, F, CHO, C(O)$R^{11}$, C(N—OH)NH$_2$, OPO$_3R^{10}$, OPO$_2$(CH$_2$)$_j$CH$_3$, CH$_2$PO$_3R^{10}$, OSO$_3R^{10}$, OSO$_2$(CH$_2$)$_j$CH$_3$, CH$_2$SO$_3R^{10}$, or CN, where j is an integer from 0 to 3; wherein $R^2$ or $R^4$=H, $R^{11}$, OC(O)$R^{11}$, NO$_2$, NHC(O)$R^{11}$, Cl, Br, I, F, CHO, C(O)$R^{11}$, C(N—OH)NH$_2$, OPO$_3R^{10}$, OPO$_2$(CH$_2$)$_j$CH$_3$, CH$_2$PO$_3R^{10}$, OSO$_3R^{10}$, OSO$_2$(CH$_2$)$_j$CH$_3$, CH$_2$SO$_3R^{10}$, CN, where j is an integer from 0 to 3, (C$R^{12}$=C$R^{12}$)$_k$CN, and (C$R^{12}$=C$R^{12}$)$_k$NO$_2$, where k is an integer from 1 to 3 or wherein, $R^6$, $R^7$, and $R^8$ can each, independently, be selected from the group consisting of H, N$_3$, $R^{11}$, NO$_2$, NHC(=NH) N($R^{10}$)$_2$, NHC(O)$R^{11}$, C(O)$R^{11}$, Cl, Br, I, F, S$R^{10}$, and (CH$_2$)$_x$C(=NH)N($R^{10}$) where x is an integer from 0 to 3; wherein $R^9$ is: 1) O$R^{10}$ and $R^{10}$ is C(CH$_3$)$_3$, CH(CH$_3$)$_2$, CH$_2$CH(CH$_3$)$_2$, CH(CH$_3$)(CH$_2$)$_m$CH$_3$ where m is an integer from 0 to 3, or (CH$_2$)$_m$CH$_3$, where m is an integer from 0 to 3, or 2) $R^9$ is selected from the group consisting of C(CH$_3$)$_3$, CH(CH$_3$)$_2$, CH$_2$CH(CH$_3$)$_2$, CH(CH$_3$)(CH$_2$)$_m$CH$_3$ where m is an integer from 0 to 3, CH$_2$CH$_3$, (CH$_2$)$_2$CH$_3$, (CH$_2$)$_3$CH$_3$, N($R^{10}$)$_2$, NO$_2$, NHC(=NH)N$R^{10}{}_2$, NHC(O)$R^{11}$, C(O)$R^{11}$, Cl, Br, I, F, S$R^{10}$, and (CH$_2$)$_x$C(=NH)N($R^{10}$)$_2$ where x is an integer from 0 to 3; wherein $R^{10}$=H, C(CH$_3$)$_3$, CH(CH$_3$)$_2$, CH$_2$CH(CH$_3$)$_2$, CH(CH$_3$)(CH$_2$)$_m$CH$_3$ where m is a integer from 0 to 3, or (CH$_2$)$_m$CH$_3$, where m is an integer from 0 to 3; wherein $R^{11}$=$R^{10}$, O$R^{10}$, or N($R^{10}$)$_2$; wherein, $R^{12}$=H or (CH$_2$)$_n$; where n is an integer from 0 to 3;

or, also for General Structure I, wherein, $R^3$ can be selected from the group consisting of H, $R^{11}$, OC(O)

wherein, $R^6$, $R^7$, and $R^8$ can each independently be selected from the group consisting of H, N$_3$, $R^{11}$, NO$_2$, NHC(=NH)

$N(R^{10})_2$, $NHC(O)R^{11}$, Cl, Br, I, F, $SR^{10}$, and $(CH_2)_xC(=NH)N(R^{10})_2$ where x is an integer from 0 to 3; wherein $R^9$ is: 1) $OR^{10}$ and $R^{10}$ is $C(CH_3)_3$, $CH(CH_3)_2$, $CH_2CH(CH_3)_2$, $CH(CH_3)(CH_2)_mCH_3$ where m is an integer from 0 to 3, or $(CH_2)_mCH_3$, where m is an integer from 0 to 3, or 2) $R^9$ is selected from the group consisting of $C(CH_3)_3$, $CH(CH_3)_2$, $CH_2CH(CH_3)_2$, $CH(CH_3)(CH_2)_mCH_3$ where m is an integer from 0 to 3, $CH_2CH_3$, $(CH_2)_2CH_3$, $(CH_2)_3CH_3$, $N(R^{10})_2$, $NO_2$, $NHC(=NH)N(R^{10})_2$, $NHC(O)R^{11}$, $C(O)R^{11}$, Cl, Br, I, F, $SR^{10}$, and $(CH_2)_xC(=NH)N(R^{10})_2$ where x is an integer from 0 to 3; wherein $R^{10}$=H, $C(CH_3)_3$, $CH(CH_3)_2$, $CH_2CH(CH_3)_2$, $CH(CH_3)(CH_2)_mCH_3$ where m is an integer from 0 to 3, or $(CH_2)_mCH_3$, where m is an integer from 0 to 3; wherein $R^1=R^{10}$, $OR^{10}$, or $N(R^{10})_2$; wherein, $R^{12}$=H or $(CH_2)_n$; where n is an integer from 0 to 3;

or, also for General Structure I, wherein, $R^1$ or $R^5$=H, $R^{11}$, $OC(O)R^{11}$, $NO_2$, $NHC(O)R^{11}$, Cl, Br, I, F, CHO, $C(O)R^{11}$, $C(N-OH)NH_2$, $OPO_3R^{10}$, $OPO_2(CH_2)_jCH_3$, $CH_2PO_3R^{10}$, $OSO_3R^{11}$, $OSO_2(CH_2)_jCH_3$, $CH_2SO_3R^{10}$, CN, where j is an integer from 0 to 3, $(CR^{12}=CR^{12})_kCN$ and $(CR^{12}=CR^{12})_kNO_2$, where k is an integer from 1 to 3; wherein, $R^2$ and $R^4$ can each, independently, be selected from the group consisting of H, $R^{11}$, $OC(O)R^{11}$, $NO_2$, $NHC(O)R^{11}$, Cl, Br, I, F, CHO, $C(O)R^{11}$, $C(N-OH)NH_2$, $OPO_3R^{10}$, $OPO_2(CH_2)_jCH_3$, $CH_2PO_3R^{10}$, $OSO_3R^{10}$, $OSO_2(CH_2)_jCH_3$, $CH_2SO_3R^{10}$, and CN, where j is an integer from 0 to 3; wherein $R^3$ can be selected from the group consisting of H, $R^{11}$, $OC(O)R^{11}$, $NHC(O)R^{11}$, Cl, Br, I, F, CHO, $C(O)R^{11}$, $C(N-OH)NH_2$, $OPO_3R^{10}$, $OPO_2(CH_2)_jCH_3$, $CH_2PO_3R^{10}$, $OSO_3R^{10}$, $OSO_2(CH_2)_jCH_3$, $CH_2SO_3R^{10}$, and CN, where j is an integer from 0 to 3; wherein, $R^6$, $R^7$, and $R^8$ can each, independently, be selected from the group consisting of H, $N_3$, $R^{11}$, $NO_2$, $NHC(=NH)N(R^{10})_2$, $NHC(O)R^{11}$, $C(O)R^{11}$, Cl, Br, I, F, $SR^{10}$, and $(CH_2)_xC(=NH)N(R^{10})_2$ where x is an integer from 0 to 3; wherein $R^9$ is: 1) $OR^{10}$ and $R^{10}$ is $C(CH_3)_3$, $CH(CH_3)_2$, $CH_2CH(CH_3)_2$, $CH(CH_3)(CH_2)_mCH_3$ where m is an integer from 0 to 3, or $(CH_2)_mCH_3$, where m is an integer from 0 to 3, or 2) $R^9$ is selected from the group consisting of $C(CH_3)_3$, $CH(CH_3)_2$, $CH_2CH(CH_3)_2$, $CH(CH_3)(CH_2)_mCH_3$ where m is an integer from 0 to 3, $CH_2CH_3$, $(CH_2)_2CH_3$, $(CH_2)_3CH_3$, $N(R^{10})_2$, $NO_2$, $NHC(=NH)N(R^{10})_2$, $NHC(O)R^{11}$, $C(O)R^{11}$, Cl, Br, I, F, $SR^{10}$, and $(CH_2)_xC(=NH)N(R^{10})_2$ where x is an integer from 0 to 3; wherein $R^{10}$=H, $C(CH_3)_3$, $CH(CH_3)_2$, $CH_2CH(CH_3)_2$, $CH(CH_3)(CH_2)_mCH_3$ where m is an integer from 0 to 3, or $(CH_2)_mCH_3$, where m is an integer from 0 to 3; wherein $R^{10}$=H, $C(CH_3)_3$, $CH(CH_3)_2$, $CH_2CH(CH_3)_2$, $CH(CH_3)(CH_2)_mCH_3$ where m is an integer from 0 to 3, or $(CH_2)_mCH_3$, where m is an integer from 0 to 3; wherein $R^{11}=R^{10}$, $OR^{10}$, or $N(R^{10})_2$; and wherein, $R^{12}$=H or $(CH_2)_n$; where n is an integer from 0 to 3.

3. The method, according to claim 2, wherein said sialidase is bacterial sialidase in bacterial vaginosis.

4. The method, according to claim 2, wherein said sialidase is bacterial sialidase in periodontal diseases.

5. The method, according to claim 2, wherein said sialidase is bacterial sialidase in *Pseudomonas aeruginosa* infection.

6. The method, according to claim 2, wherein said sialidase is viral sialidase in influenza virus infection.

7. The method, according to claim 2, wherein said sialidase is human sialidase.

8. The method, according to claim 2, wherein said sialidase is trans-sialidase in *Trypanosoma cruzi* infection.

* * * * *

UNITED STATES PATENT AND TRADEMARK OFFICE
CERTIFICATE OF CORRECTION

PATENT NO.   : 6,667,161 B1
DATED        : December 23, 2003
INVENTOR(S)  : Stephen C. Johnson, Ming Luo and Shija Yan It is certified that error appears in the above-identified patent and that said Letters Patent is hereby corrected as shown below:

Column 1,
Line 10, "continuation-in-part of U.S. patent" should read
-- continuation-in-part of co-pending U.S. patent --.
Line 52, "Kienk" should read -- Klenk --.
Line 57, "silaidases" should read -- sialidases --.

Column 2,
Lines 62-63, "2-O-([4-(4-nitrophenylazo)resocinyl]-4-deoxy-N-acetylneuraminic acid-alpha-ketoside," should read -- 2-O-([4-(4-nitrophenylazo)resorcinyl]-4-deoxy-N-acetylneuraminic acid-alpha ketoside, --.

Column 3,
Lines 60-61, "2-O-[4-(4-nitropheynazo)resorcinyl]-4-ethoxy-N-acetylneuraminic acid-alpha-ketoside," should read -- 2-O-[4-(4-nitrophenylazo)resorcinyl]-4-ethoxy-N-acetylneuraminic acid-alpha-ketoside, --.

Column 4,
Lines 18-19,"2-O-[4-(4-nitropheynazo)resorcinyl]-4-fluoro-N-acetylneuraminic acid-alpha-ketoside," should read -- 2-O-[4-(4-nitrophenylazo)resorcinyl]-4-fluoro-N-acetylneuraminic acid-alpha-ketoside, --.

Column 5,
Line 50,

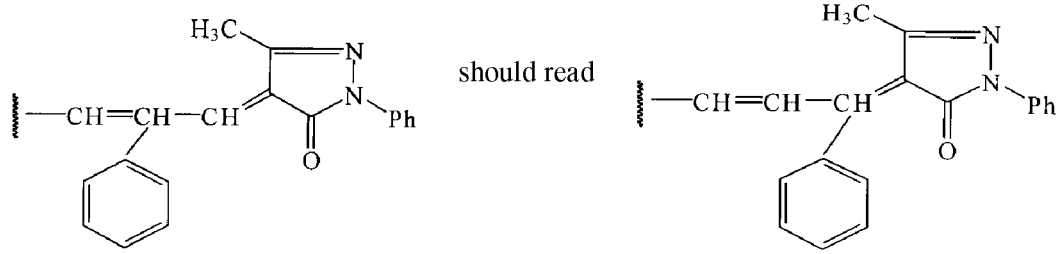

Column 6
Line 52, "$OSO(CH_2)_jCH_3$," should read -- $OSO_2(CH_2)_jCH_3$, --.

UNITED STATES PATENT AND TRADEMARK OFFICE
CERTIFICATE OF CORRECTION

PATENT NO.    : 6,667,161 B1                                         Page 2 of 4
DATED         : December 23, 2003
INVENTOR(S)   : Stephen C. Johnson, Ming Luo and Shija Yan It is certified that error appears in the above-identified patent and that said Letters Patent is hereby corrected as shown below:

Column 7,
Line 10,

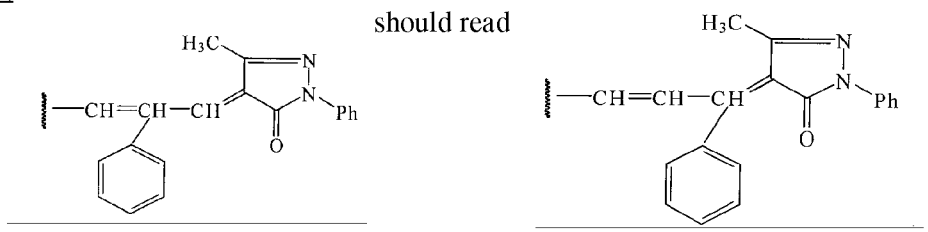

Column 8,
Line 57, "$OSO_3R^7$, $OSO_2SO_3R^7$, or" should read -- $OSO_3R^7$, $OSO_2(CH_2)_jCH_3$, $CH_2SO_3R^7$, or --.
Line 66, "where m is an in" should read -- where $m$ is an integer --.

Column 9.
Line 54, "$CH_2SO_3R^{12}$, and where j" should read -- $CH_2SO_3R^{12}$, and CN, where j --.
Line 59, "$R^2$=H" should read -- $R^{12}$=H --.
Line 61, "integer form 0 to 3" should read -- integer from 0 to 3 --.

Column 10
Line 14, "H, $R^3$" should read -- H, $R^{13}$ --.
Line 24, "integer form 0 to 3;" should read -- integer from 0 to 3;--

Column 14,
Line 67, "NeuSAc" should read -- Neu5Ac --.

Column 17,
Table 1, Column $R_7$,    " $NH_2$         should read    -----$NH_2$
                            $NH_2$                         ---$NH_2$
                            $NH_2$                         ---$NH_2$
                            $NH_2$                         ---$NH_2$
                            $OCH_3$                        ---$OCH_3$
                            $OCH_3$                        ---$OCH_3$
                            ---$OCH_3$                     ---$OCH_3$
                            $OCH_3$                        ---$OCH_3$
                            ---OH                          ---OH
                            ---OH"                         ---OH--.

Column 23.
Line 6, "glycdsyl chloride" should read -- glycosyl chloride --.

UNITED STATES PATENT AND TRADEMARK OFFICE
CERTIFICATE OF CORRECTION

PATENT NO.   : 6,667,161 B1
DATED        : December 23, 2003
INVENTOR(S)  : Stephen C. Johnson, Ming Luo and Shija Yan It is certified that error appears in the above-identified patent and that said Letters Patent is hereby corrected as shown below:

Column 27,
Line 33, "2-methyl-2-thiosetidourea" should read -- 2-methyl-2-thiopseudourea --.

Column 28,
Lines 49 and 52, "would provides" should read -- would provide --.

Column 35,
Line 55,

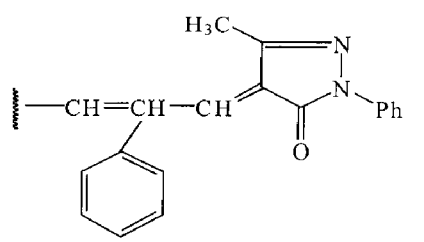 should read 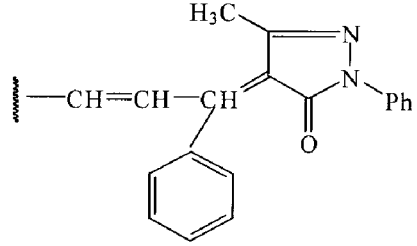

Column 36,
Lines 66-67, "$(CR^{12}=CR^{12})\ NO^2$ where k" should read -- $(CR^{12}=CR^{12})_k NO_2$, where *k* --.

Column 37,
Line 10,

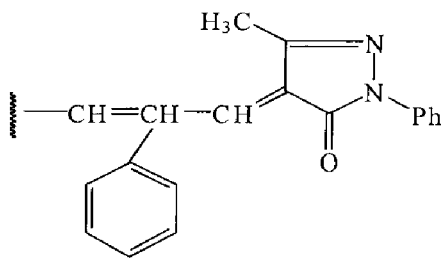 should read 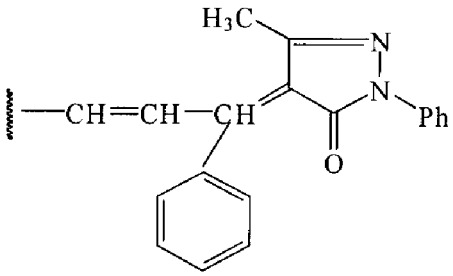

Line 60, "$N(R^{10}_2, NO_2, NHC(=N)N(R^{10})_2,$" should read -- $N(R^{10})_2, NO_2, NHC(=NH)N(R^{10})_2,$ --.

UNITED STATES PATENT AND TRADEMARK OFFICE
CERTIFICATE OF CORRECTION

PATENT NO. : 6,667,161 B1
DATED : December 23, 2003
INVENTOR(S) : Stephen C. Johnson, Ming Luo and Shija Yan It is certified that error appears in the above-identified patent and that said Letters Patent is hereby corrected as shown below:

Column 39,
Line 10, 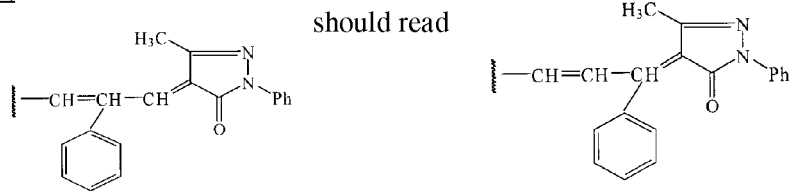

Line 53, "$(CH_2)_xC(=NH)N(R^{10})$" should read -- $(CH_2)_xC(=NH)N(R^{10})_2$ --.

Column 40,
Line 2, "$CH_2PO_3R^{11}$," should read -- $CH_2PO_3R^{10}$, --.
Line 25,

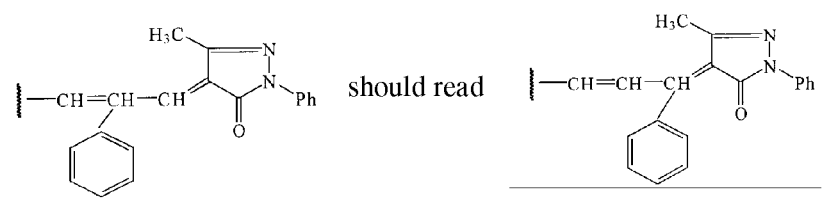

Column 41,
Line 14, "wherein $R^1=R^{10}$," should read -- "wherein $R^{11}=R^{10}$, --.
Line 19, "$OSO_3R^{11}$" should read -- $OSO_3R^{10}$ --.

Signed and Sealed this

Sixteenth Day of November, 2004

JON W. DUDAS
*Director of the United States Patent and Trademark Office*